(12) United States Patent
Wang et al.

(10) Patent No.: US 11,710,541 B2
(45) Date of Patent: Jul. 25, 2023

(54) CHEMICAL PATTERN RECOGNITION METHOD FOR EVALUATING QUALITY OF TRADITIONAL CHINESE MEDICINE BASED ON MEDICINE EFFECT INFORMATION

(71) Applicant: SHENZHEN INSTITUTE FOR DRUG CONTROL (SHENZHEN TESTING CENTER OF MEDICAL DEVICES), Shenzhen (CN)

(72) Inventors: Tiejie Wang, Shenzhen (CN); Yi Lu, Shenzhen (CN); Lijun Wang, Shenzhen (CN); Kun Jiang, Shenzhen (CN); Yang Wang, Shenzhen (CN); Jue Wang, Shenzhen (CN); Guo Yin, Shenzhen (CN); Yang Huang, Shenzhen (CN); Yibao Jin, Shenzhen (CN)

(73) Assignee: SHENZHEN INSTITUTE FOR DRUG CONTROL (SHENZHEN TESTING CENTER OF MEDICAL DEVICES), Shenzhen (CN)

( * ) Notice: Subject to any disclaimer, the term of this patent is extended or adjusted under 35 U.S.C. 154(b) by 0 days.

(21) Appl. No.: 17/779,835

(22) PCT Filed: Dec. 2, 2019

(86) PCT No.: PCT/CN2019/122425
§ 371 (c)(1),
(2) Date: May 25, 2022

(87) PCT Pub. No.: WO2021/056814
PCT Pub. Date: Apr. 1, 2021

(65) Prior Publication Data
US 2023/0017825 A1 Jan. 19, 2023

(30) Foreign Application Priority Data
Sep. 25, 2019 (CN) .......................... 201910913203.2

(51) Int. Cl.
*G16C 20/20* (2019.01)
*G01N 30/86* (2006.01)
(Continued)

(52) U.S. Cl.
CPC ......... *G16C 20/20* (2019.02); *G01N 30/8631* (2013.01); *G16C 20/70* (2019.02); *G01N 2030/027* (2013.01)

(58) Field of Classification Search
CPC ........................... G16C 20/20; G01N 30/8631
(Continued)

(56) References Cited

U.S. PATENT DOCUMENTS

2003/0068828 A1* 4/2003 Dadala ................ F02M 27/042
702/27
2007/0288217 A1* 12/2007 Dadala ............... G01N 30/8651
703/12
(Continued)

FOREIGN PATENT DOCUMENTS

CN 105138861 A 12/2015
CN 106290643 A 1/2017
(Continued)

OTHER PUBLICATIONS

Fan, X.-H. et al, Analytica Chimica Acta 2006, 555, 217-224.*
(Continued)

*Primary Examiner* — Arlen Soderquist
(74) *Attorney, Agent, or Firm* — Kathleen D. Rigaut; Howson & Howson, LLP

(57) ABSTRACT

A chemical pattern recognition method for evaluating the quality of a traditional Chinese medicine based on medicine effect information, comprising: collecting chemical information of a traditional Chinese medicine sample, obtaining medicine effect information reflecting a clinical therapeutic effect thereof, performing spectrum-effect relationship
(Continued)

analysis on the chemical information and the medicine effect information, and obtaining an index significantly related to the medicine effect as a feature chemical index; dividing the traditional Chinese medicine sample into a training set and a test set; using a pattern recognition method to extract a feature variable from samples of the training set by taking the feature chemical index as an input variable; building a pattern recognition model using the feature variable; and substituting feature variable values of samples of the test set into the model, and completing chemical pattern recognition evaluation of the quality of the traditional Chinese medicine. According to the method, chemical reference substances are not needed, the chemical pattern recognition model is built on the basis of the feature chemical index reflecting the medicine effect, the one-sidedness and the subjectivity of the existing standards are overcome, and a traditional Chinese medicine quality evaluation system capable of reflecting both the clinical therapeutic effect and overall chemical composition information is finally formed.

2 Claims, 12 Drawing Sheets

(51) Int. Cl.
  *G16C 20/70* (2019.01)
  *G01N 30/02* (2006.01)

(58) Field of Classification Search
  USPC ............................................. 436/161
  See application file for complete search history.

(56) References Cited

U.S. PATENT DOCUMENTS

| | | | | |
|---|---|---|---|---|
| 2008/0169926 | A1* | 7/2008 | Reep | G06K 19/07749 340/572.1 |
| 2018/0209900 | A1* | 7/2018 | Salmon | G01N 33/15 |
| 2021/0208063 | A1* | 7/2021 | Green | G01N 21/63 |

FOREIGN PATENT DOCUMENTS

| | | |
|---|---|---|
| CN | 107132194 A | 9/2017 |
| CN | 108195989 A | 6/2018 |
| CN | 108509997 A | 9/2018 |
| CN | 108732126 A | 11/2018 |
| CN | 109507123 A | 3/2019 |
| CN | 109856265 A | 6/2019 |
| CN | 110110789 A | 8/2019 |
| CN | 110187020 A | 8/2019 |
| CN | 110514611 A | 11/2019 |
| KR | 20090062323 A | 6/2009 |

OTHER PUBLICATIONS

Li, S et al., Chinese Medicine 2008, 3, paper 7, 16 pages.*
Li, Y.-G. etal, Journal of Chromatogaphy A 2009, 1216, 1941-1953.*
Han, B.-X. et al, Pharmacognosy Magazine 2009, 5, 279-286.*
Jiang, Y. et al, Analytica Chimica Acta 2010, 6657, 9-18.*
Liang, Y. et al, Journal of Separation Science 2010, 33, 410-421.*
Chen, C. et al, Chemical Biology & Drug Design 2013, 81, 688-694.*
Liang, X. et al, Pharmacognosy Magazine 2013, 9, 238-243.*
Yang, H. et al, Journal of Pharmaceutical and Biomedical Analysis 2015, 115, 10-19.*
Huang, Y. et al, Journal of Chromatography B 2016, 1026, 27-35.*
Liang, Z. et al, BMC Medical Genomics 2016, 9 (Supplement 2), 195-204.*
Jiang, J. et al, Transactions of Tianjin University 2017, 23, 237-244.*
Zhang, Y. et al, Journal of Separation Science 2017, 40, 4511-4520.*
Chen, Z. et al, Chinese Medicine 2018, 13, paper 12, 11 pages.*
Xin, W. et al, Phytomedicine 2018, 44, 103-108.*
Zhang, C. et al, Journal of Pharmaceutical and Biomedical Analysis 2018, 159, 296-304.*
Li, Y. et al, Revista Brasileira de Farmacognosia 2018, 28, 533-541.*
Wang, Y. et al, Analytical Letters 2018, 51, 2173-2191.*
Written Opinion of the International Searching Authority, dated May 27, 2020, issued in corresponding International Application No. PCT/CN2019/122425, filed Dec. 2, 2019.
Second Office Action, dated Jun. 6, 2022, issued in corresponding Chinese Application No. 201910913203.2.
Li, Lei et al., "Development of HPLC fingerprint bar code technique for authentication and quality assessment of Radix Salvia Miltiorrhiza," Chinese Traditional and Herbal Drugs, vol. 34, Jul. 2003, pp. 650-653.
Wei, Liang et al., "Research on the application of grey system theory in the pattern recognition for chromatographic fingerprints of traditional Chinese medicine," Chinese Journal of Chromatography, vol. 31, No. 2, Feb. 2013, pp. 127-132.
Extended European Search Report, dated Jan. 18, 2023, issued in corresponding European Application No. 19946314.2.
Wang, Fei et al., "From chemical consistency to effective consistency in precise quality discrimination of Sophora flower-bud and Sophora flower: Discovering efficacy-associated markers by fingerprint-activity relationship modeling," Journal of Pharmaceutical and Biomedical Analysis, vol. 132, Sep. 2016, pp. 7-16.

* cited by examiner

CHEMICAL PATTERN RECOGNITION METHOD FOR EVALUATING QUALITY OF TRADITIONAL CHINESE MEDICINE BASED ON MEDICINE EFFECT INFORMATION

CROSS REFERENCE TO RELATED APPLICATIONS

This application is a §371 of International Application No. PCT/CN2019/122425, filed Dec. 2, 2019, which claims priority to Chinese Patent Application No. 201910913203.2 filed Sep. 25, 2019, the entire contents of each being incorporated by reference as though set forth in full.

TECHNICAL FIELD

The present invention belongs to the field of traditional Chinese medicine quality evaluation, and relates to a method for establishing chemical pattern recognition for evaluating traditional Chinese medicine quality based on pharmacodynamics information.

BACKGROUND

China has the richest resources of traditional Chinese medicines (TCMs) in the world, which accounts for almost 70% of the global market. With the globalization of economy and the outstanding performance in clinical application, the traditional Chinese medicines have greatly developed. However, some issues emerged with the development of TCMs, such as: for various valuable traditional Chinese medicines, some counterfeits or even adulterated products are disguised for sale as quality ones; the quality of traditional Chinese medicines varies greatly due to many factors such as producing area, climate, soil conditions, location and harvesting season; and some valuable wild traditional Chinese medicines have been endangered due to excessive exploitation, and thus new medicinal parts and alternative species are urgently required. Traditional Chinese medicines are complex and huge mixed system and usually contain multi-components, multi-targets and multi-effects, which to some extent increases the difficulty to evaluate their quality. At present, the quality evaluation of traditional Chinese medicines at domestic or international is mainly to analyze a few chemical components as quality index while the methods developed by scholars were not often based on their, medicinal effect. The lack of comprehensive and reliable quality evaluation system for traditional Chinese medicines not only increases the health risks for users, but also affects the international reputation, competitiveness and influence for the traditional Chinese medicine.

CN108509997A discloses a near-infrared spectroscopy-based method for chemical pattern recognition of authenticity of a traditional Chinese medicine, Chinese honeylocust spine (also known as Zaojiaoci or Spina *gleditsiae*). The method combines a near-infrared spectrum collection method, a first derivative pre-treatment method, a successive projections algorithm, a Kennard-Stone algorithm, and a stepwise algorithm to perform the chemical pattern recognition on the authenticity of the Spina *gleditsiae*. The results of the pattern recognition method are therefore accurate and reliable, and the Spina *gleditsiae* and counterfeits thereof can be accurately discriminated. However, the characteristic wave number points were obtained only based on the collection of chemical information and the chemical processing method, but not all of the characteristic wave number points are correlated with the pharmacodynamics of drugs. The excess uncorrelated wave number points result in a more complicated discriminant model.

For modernization and internationalization of the traditional Chinese medicine, it is urgent to establish a quality evaluation method for the traditional Chinese medicine, which can fully reflect the chemical information of traditional Chinese medicine not only based on the theory of the traditional Chinese medicine, but also under the guidance of modern scientific pharmacodynamics experiments.

SUMMARY

In view of the deficiencies in the prior art, an object of the present invention is to provide a method for establishing chemical pattern recognition for evaluating traditional Chinese medicine quality based on pharmacodynamics information. The method provided in the invention can present the chemical information of traditional Chinese medicine in full scale without using reference chemicals. The chemical pattern recognition model is established based on pharmacodynamics information and the discriminant model is thus more accurate. Furthermore, the present invention overcomes the subjectivity in the discrimination, and makes the results of the discrimination accurate and reliable.

To achieve the object, the present invention adopts the technical route described below.

The present invention provides a method for establishing chemical pattern recognition for evaluating traditional Chinese medicine quality based on pharmacodynamics information. The developed method includes the following steps:
(1) collecting the whole chemical information capable of representing internal quality of traditional Chinese medicine samples; obtaining pharmacodynamics information representing clinical efficacy of the traditional Chinese medicine samples; performing spectrum-effect relationship analysis on the chemical information and the pharmacodynamics information; and obtaining indexes significantly correlated with the medicinal effect as characteristic chemical indexes;
(2) classifying the traditional Chinese medicine samples into a training set and a testing set, and extracting characteristic variables from the samples in the training set by using the characteristic chemical indexes obtained in step (1) as input variables by a supervised pattern recognition method;
(3) establishing a pattern recognition model by using the characteristic variables extracted in step (2); and
(4) bringing characteristic variable values of the samples in the testing set into the pattern recognition model, and completing chemical pattern recognition evaluation of the traditional Chinese medicine quality.

In the present invention, the pattern recognition model is built by obtaining indexes significantly correlated with the medicinal effect as characteristic chemical indexes and extracting valid characteristic variables. Since these characteristic variables are all significantly correlated with the medicinal effect, the interference of uncorrelated variables and the resulted complication of the pattern recognition model are avoided. Therefore, a more accurate pattern recognition model can be obtained, by which the authenticity discrimination and quality grading for traditional Chinese medicines are simpler and more direct. The results are thus accurate and reliable. Furthermore, the method in the present invention are also useful to find alternatives to precious traditional Chinese medicines.

In the present invention, the traditional Chinese medicine includes Exocarpium *citri grandis* (Huajuhong), *Salviae* miltiorrhizae radix et rhizoma (Danshen), Spina *gleditsiae* (Zaojiaoci), amomi fructus (Sharen), Mahoniae caulis (Gonglaomu) or *Notoginseng* radix et rhizoma (Sanqi).

In the present invention, the collection of the chemical information refers to obtain chemical characteristic information of a traditional Chinese medicine according to a recognition goal of this traditional Chinese medicine. For example, if the goal is to discriminate the authenticity of a traditional Chinese medicine, the collection of the chemical information refers to obtain the whole chemical information capable of representing internal quality of samples of the traditional Chinese medicine and counterfeits thereof; if the goal is to perform quality grading for a traditional Chinese medicine, the collection of the chemical information refers to obtain the whole chemical information of internal quality of each grade of the traditional Chinese medicine, where the collected chemical information is capable of representing the respective quality grades.

In the present invention, the pharmacodynamics information representing clinical efficacy of the traditional Chinese medicines was obtained by using the conventional means in the pharmacodynamics study of the traditional Chinese medicine.

Preferably, after the chemical information capable of representing the internal quality of the traditional Chinese medicine samples is collected in step (1), the collected data was converted into a m×n matrix, wherein n is the number of the traditional Chinese medicine samples, and m is the number of chemical information collected for each traditional Chinese medicine sample.

In the present invention, the method for collecting the chemical information of the traditional Chinese medicine samples is a spectrum collection method, a chromatography collection method, a mass spectrum collection method or a nuclear magnetic resonance method.

Preferably, the spectrum collection method is for any one of ultraviolet spectrometry, Infrared Spectrometry, Near-Infrared Spectrometry, Raman Spectrometry or Fluorescence Spectrometry.

Preferably, the chromatography collection method is high performance liquid chromatography(HPLC) or ultra-high performance liquid chromatography(UPLC).

In the present invention, the collection of the chemical information refers to collecting a characteristic chemical signal capable of representing the internal quality of a traditional Chinese medicine. For example, if the chemical information is collected by ultraviolet spectrometry, the collection of the chemical information refers to collecting ultraviolet characteristic absorption peaks of the traditional Chinese medicine; if the chemical information is collected by high performance liquid chromatography, the collection of the chemical information refers to collecting all of the significant peaks of the traditional Chinese medicine in the high-performance liquid chromatography.

In the present invention, the medicinal effect correlation analysis on the chemical information refers to analysis the correlation between the collected chemical information and the medicinal effect, selecting chemical information significantly correlated with the medicinal effect as pharmacodynamic indexes, and removing chemical information uncorrelated with the medicinal effect.

In the present invention, a method for the spectrum-effect relationship analysis in step (1) may be a method for bivariate correlation analysis, regression analysis, gray relational analysis, a partial least squares method or principal component analysis.

In the present invention, the supervised pattern recognition method in step (2) is discriminant analysis of principle components, stepwise discriminant analysis, a partial least squares discriminant method, a support vector machine or an artificial neural network algorithm.

Preferably, when the characteristic variables are extracted in step (2), k pieces of uncorrelated chemical information are removed to obtain an (m−k)×n matrix, where n is the number of the traditional Chinese medicine samples, and m is the quantity of chemical information collected for each traditional Chinese medicine sample.

In the present invention, the flowchart of the method for establishing chemical pattern recognition for evaluating traditional Chinese medicine quality based on pharmacodynamics information is shown in FIG. 1, which reflects the overall process of the method and completes the pattern recognition under the guidance of the medicinal effect (i.e. pharmacological activity), so as to evaluate the quality of the traditional Chinese medicine and predict and analyze unknown samples.

Preferably, the method for establishing chemical pattern recognition for evaluating traditional Chinese medicine quality based on pharmacodynamics information includes chemical pattern recognition on authenticity of the traditional Chinese medicine, *Salviae* miltiorrhizae radix et rhizoma, chemical pattern distinction for discriminating *Citrus grandis* 'Tomentosa' from *Citrus grandis* (L.) Osbeck in Exocarpium *citri grandis*, or chemical pattern recognition on authenticity of Spina *gleditsiae*.

Preferably, the method for chemical pattern recognition on authenticity of the traditional Chinese medicine, *Salviae* miltiorrhizae radix et rhizoma, or for chemical pattern distinction for discriminating *Citrus grandis* 'Tomentosa' from *Citrus grandis* (L.) Osbeck in Exocarpium *citri grandis* includes the following steps:

A. Collecting chemical information of *Salviae* miltiorrhizae radix et rhizoma and counterfeits thereof or collecting chemical information of *Citrus grandis* 'Tomentosa' and *Citrus grandis* (L.) Osbeck in Exocarpium *citri grandis* by high performance liquid chromatography (HPLC), performing data normalization on specific absorption peaks selected from HPLC chromatograms by a Z-normalization method, performing bivariate spectrum-effect correlation analysis on the normalized data, obtaining HPLC fingerprint data significantly correlated with pharmacodynamic activity of *Salviae* miltiorrhizae radix et rhizoma and counterfeits thereof or HPLC fingerprint data significantly correlated with pharmacodynamic activity of *Citrus grandis* 'Tomentosa' and *Citrus grandis* (L.) Osbeck in Exocarpium *citri grandis*, and using the HPLC fingerprint data as characteristic chemical indexes representing the medicinal effect;

B. Classifying the samples of *Salviae* miltiorrhizae radix et rhizoma and its counterfeits or the samples of Exocarpium *citri grandis* randomly into a training set and a testing set, using the characteristic chemical indexes obtained in step A as input variables to screen characteristic chemical indexes of the samples in the training set with stepwise discriminant analysis, thereby removing uncorrelated variables, and screening out characteristic variables;

C. Establishing the pattern recognition model for *Salviae* miltiorrhizae radix et rhizoma and its counterfeits or for the samples of Exocarpium *citri grandis* by using the characteristic variables obtained in step B; and D. Bringing characteristic variable values of the samples in the testing set into the pattern recognition model to determine the accuracy rate for discriminating *Salviae miltiorrhizae radix et rhizoma* and counterfeits thereof or for discriminating *Citrus grandis* 'Tomentosa' from *Citrus grandis* (L.) Osbeck in Exocarpium *citri grandis*.

Preferably, the principle for selecting the specific absorption peaks of *Salviae* miltiorrhizae radix et rhizoma and counterfeits thereof in step A is to select peaks satisfying at least one of following conditions: (I) peaks common to *Salviae* miltiorrhizae radix et rhizoma, radix et rhizoma of *Salvia przewalskii* Maxim. (*Salvia przewalskii* Maxim.) and radix et rhizoma of *Salvia yunnanensis* C. H. Wright (*Salvia yunnanensis* C. H. Wright); (11) peaks respectively specific to *Salviae* miltiorrhizae radix et rhizoma, *Salvia przewalskii* Maxim. and *Salvia yunnanensis* C. H. Wright; and (III) peaks with high content of components.

Preferably, the principle for selecting the specific absorption peaks of *Citrus grandis* 'Tomentosa' and *Citrus grandis* (L.) Osbeck in Exocarpium *citri grandis* in step A is to select peaks common to *Citrus grandis* 'Tomentosa' and *Citrus grandis* (L.) Osbeck.

In the present invention, these selected specific absorption peaks represent main chemical information of the three traditional Chinese medicines, namely, *Salviae* miltiorrhizae radix et rhizoma. *Salvia przewalskii* Maxim. and *Salvia yunnanensis* C. H. Wright.

Preferably, the method in step B for the randomly classifying the samples into a training set and a testing set is random classification by using a random algorithm.

Preferably, the training set of *Salviae* miltiorrhizae radix et rhizoma and counterfeits thereof in step B includes 20 batches of samples, wherein 12 batches are of *Salviae* miltiorrhizae radix et rhizoma, 4 batches are of *Salvia przewalskii* Maxim. and 4 batches are of *Salvia yunnanensis* C. H. Wright, and the testing set includes 29 batches of samples, wherein 26 batches are of *Salviae* miltiorrhizae radix et rhizoma, 2 batches are of *Salvia przewalskii* Maxim. and 1 batch is of *Salvia yunnanensis* C. H. Wright. In the present invention, the training set and the testing set are randomly classified leading to the training set and the testing set are actually not limited to the training set and the testing set with the specific number of batches of samples described above.

Preferably, the training set of samples of Exocarpium *citri grandis* in step B includes 22 batches of samples, wherein 10 batches are of *Citrus grandis* 'Tomentosa' and 12 batches are of *Citrus grandis* (L.) Osbeck, and the testing set includes 9 batches of samples, wherein 5 batches are of samples of *Citrus grandis* 'Tomentosa' and 4 batches are of *Citrus grandis* (L.) Osbeck.

Preferably, the characteristic variables screened in step B are $X_6$, $X_7$ and $X_{13}$; that is, only 3 characteristic variables correlated with the classification are screened out by the stepwise discriminant analysis, even plenty of HPLC fingerprint data significantly correlated with pharmacodynamic activity are obtained by the method provided in the present invention, which thereby greatly simplifies the model function.

Preferably, functions of the pattern recognition model in step C are as follows.

$$F_1=0.492X_6+8.762X_7-1.249X_{13}-1.869$$

$$F_2=-2.571X_6+4.521X_7+3.277X_{13}+1.288$$

Preferably, the screened characteristic variables for the samples of Exocarpium *citri grandis* in step B are $X_7$, $X_8$ and $X_{20}$.

Preferably, the established function of the pattern recognition model for the samples of Exocarpium *citri grandis* in step C is as follows.

$$F_1=0.828X_7+0.767X_8-1.303X_{20}-0.099$$

Preferably, the method for chemical pattern recognition on authenticity of Spina *gleditsiae*. in the present invention includes the following steps:

I. Collecting chemical information of Spina *gleditsiae*. and counterfeits thereof by near-infrared spectrometry, obtaining pharmacodynamics information representing clinical efficacy of the traditional Chinese medicine, performing spectrum-effect relationship analysis on the chemical information and the pharmacodynamics information, and thereby obtaining characteristic peaks significantly correlated with the medicinal effect as characteristic chemical indexes;

II. Randomly classifying Spina *gleditsiae*. and counterfeits thereof into a training set and a testing set, screening characteristic chemical indexes of the samples in the training set by stepwise discriminant analysis using the characteristic chemical indexes obtained in step I as input variables, thereby removing uncorrelated variables, and screening out characteristic variables;

III. Establishing a pattern recognition model by using the characteristic variables obtained in step II; and IV. Bringing characteristic variable values of the samples in the testing set into the pattern recognition model to determine the accuracy for discriminating Spina *gleditsiae*. and counterfeits thereof.

Preferably, after the collection of chemical information of Spina *gleditsiae*. and counterfeits thereof by the near-infrared spectrometry in step I, the method further includes pre-treatment of the spectral data of the chemical information: removing interference peaks and water peaks in the original spectrum to obtain peaks within spectral bands of 11800-7500 $cm^{-1}$, 6500-5500 $cm^{-1}$, and 5000-4200 $cm^{-1}$, selecting the peaks within the spectral band of 5000-4200 $cm^{-1}$ as model analysis peaks, pre-treating the peaks within the spectral band of 5000-4200 $cm^{-1}$ by using a first derivative ($1^{st}$ D) pre-treatment method, and extracting characteristic peaks by using a successive projections algorithm (SPA).

Preferably, the interference peaks are peaks within spectral bands of 12000-11800 $cm^{-1}$, 4200-4000 $cm^{-1}$, 7500-6500 $cm^{-1}$, and 5500-5000 $cm^{-1}$, and the water peaks are peaks within spectral bands of 7500-6500 $cm^{-1}$ and 5500-5000 $cm^{-1}$.

Preferably, the training set in step II includes 32 batches of samples, wherein 24 batches are of Spina *gleditsiae*., 3 batches are of *Gleditsia japonica* Miq., 2 batches are of *Gleditsia microphylla* Gordon ex Y. T. Lee and 3 batches are of *Rubus cochinchinensis* Tratt., and the testing set includes 11 batches of samples, wherein 8 batches are of Spina *gleditsiae*., 1 batch is of *Gleditsia japonica* Miq., 1 batch is of *Gleditsia microphylla* Gordon ex YT Lee and 1 batch is of *Rubus cochinchinensis* Tratt.

Preferably, the screened characteristic variables in step II are $X_8$, $X_{10}$, $X_{14}$, and $X_{21}$.

Preferably, functions of the pattern recognition model in step III are as follows.

$$F_1=49050.801X_8+8875.62X_{10}-2798.314X_{14}+21876.983X_{21}+2.356$$

$$F_2=-27730.331X_8+34288.661X_{10}-29368.865X_{14}+10924.346X_{21}+4.075$$

Compared with the prior art, the present invention has beneficial effects described below.

The method provided in the invention can present the chemical information of traditional Chinese medicine in full scale without using reference materials. The chemical pattern recognition model is established based on pharmacodynamics information, which makes the relationship between the discriminant model and the medicinal effect closer. Also, the produced chemical pattern recognition model function is simpler, meanwhile, the discriminant accuracy can be ensured. It overcomes the one-sidedness and subjectivity of the current standards for evaluating the quality of traditional Chinese medicine with the content of only one or a few ingredients. Finally, a quality evaluation system of traditional Chinese medicine based on clinical efficacy and the information of chemical components is formed, and the results of the discrimination are proved to be accurate and reliable. With the method of the present invention, the authenticity discrimination and quality grading for traditional Chinese medicines can be performed in a simpler and more direct way and the results obtained are accurate and reliable; and the method in the present invention also helps to find alternatives for traditional Chinese medicines with high price. The method can further realize the prediction for the unknown samples. Therefore, a traditional Chinese medicine quality evaluation system is established based on the method of the present invention.

DETAILED DESCRIPTION

The technical solutions of the present invention are further described below through specific examples. Those skilled in the art should clarify that the examples described herein are used for a better understanding of the present invention and should not be construed as specific limitations to the present invention.

Figure 1:
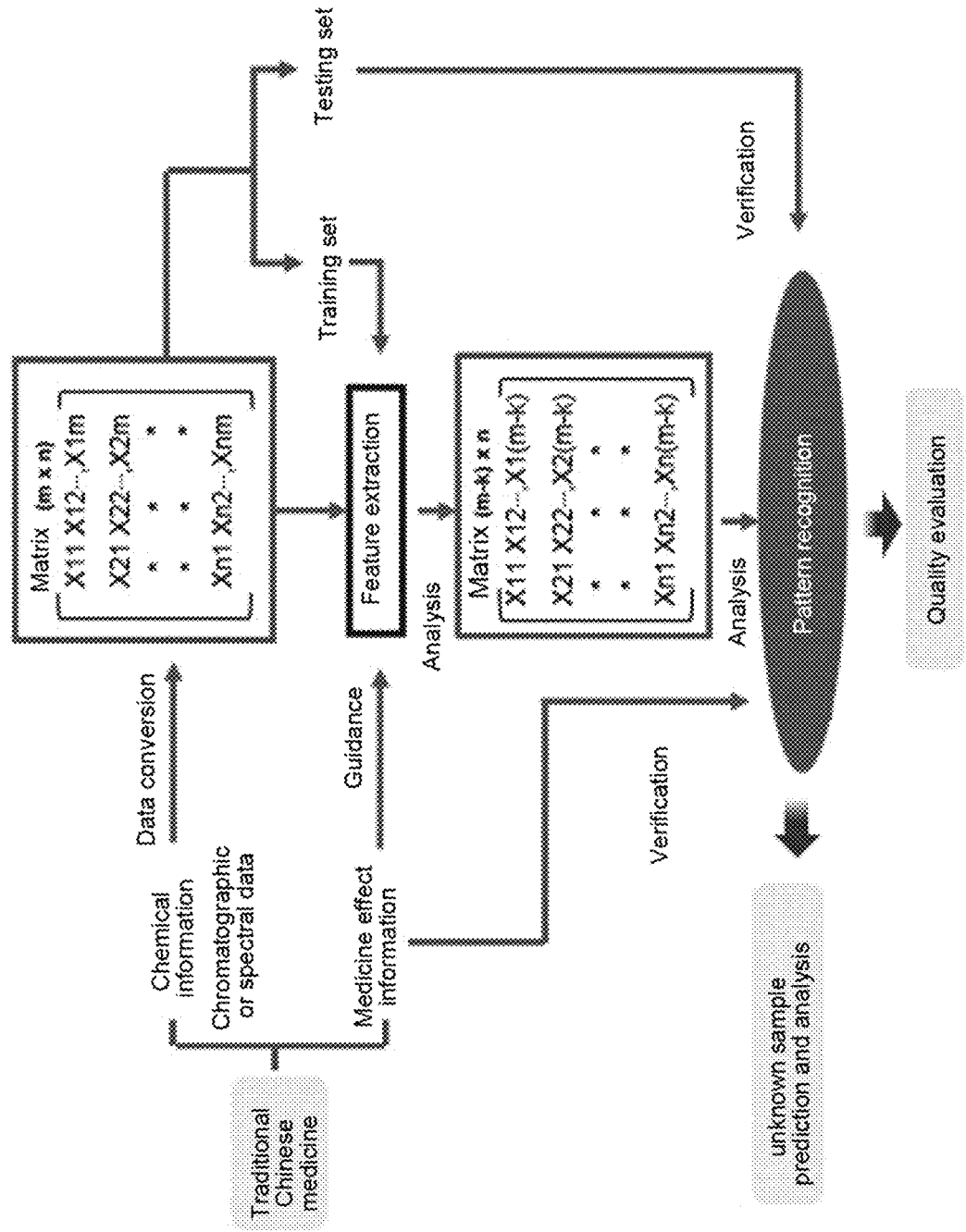
FIG. 1 is an overall flowchart showing the method for establishing chemical pattern recognition for evaluating traditional Chinese medicine quality based on pharmacodynamics information.

In the present invention, the overall flowchart of the method for establishing chemical pattern recognition for evaluating traditional Chinese medicine quality based on pharmacodynamics information is shown in FIG. 1. As shown in FIG. 1, the method includes the following steps: collecting typical, representative traditional Chinese medicines, collecting the whole chemical information capable of representing internal quality of traditional Chinese medicine samples, obtaining pharmacodynamics information capable of representing clinical efficacy of the traditional Chinese medicine samples, and extracting the characteristic chemical information under the guide of the pharmacodynamics information to obtain characteristic chemical indexes capable of representing the medicinal effect, that is, performing medicinal effect correlation analysis on the chemical information and the pharmacodynamics information to obtain chemical information indexes significantly correlated with the medicinal effect as characteristic indexes; classifying the traditional Chinese medicine samples into a training set and a testing set; extracting characteristic variables from the samples in the training set with the characteristic chemical indexes capable of representing the clinical efficacy as input variables by a supervised pattern recognition method; establishing a pattern recognition model with the extracted characteristic variables; bringing characteristic variable values of the samples in the testing set into the pattern recognition model; and completing chemical pattern recognition evaluation of the traditional Chinese medicine quality under the guide of the pharmacodynamics information (i.e. pharmacological activity).

Example 1

In this example, the instruments and software used are as follows.

High performance liquid chromatography: chromatographic column: Zobax SB-aq (250 mm×4.6 mm, 5 μm, manufactured by Agilent Technologies Inc.); mobile phase: acetonitrile (A), water containing 0.03% (v/v) phosphoric acid (B), gradient elution, elution procedure see Table 1; detection wavelength: 280 nm, flow rate: 0.8 mL min$^{-1}$, column temperature: 30° C., injection volume: 20 μL.

TABLE 1

Gradient elution procedure

| Time (min) | Flow rate (mL · min$^{-1}$) | Mobile phase A (%) | Mobile phase B (%) |
|---|---|---|---|
| 0 | 0.8 | 10 | 90 |
| 60 | 0.8 | 68 | 32 |
| 70 | 0.8 | 80 | 20 |

The random algorithm was processed by the SPSS software (developed by IBM, USA).

In this example, the samples used herein are as follows.

A total of 49 batches of samples of *Salviae milliorrhiza* Bunge (referred to as *Salviae* miltiorrhizae radix et rhizoma, i.e., DS1-DS38) and other 2 congeneric plants thereof: radix et rhizoma of *Salvia przewalskii* (referred to as *Salvia przewalskii* Maxim., i.e., GS39-GS44) and radix et rhizoma of *Salvia yunnanensis* (referred to as *Salvia yunnanensis* C. H. Wright., i.e., YN45-YN49), were collected from different regions, and all of the samples were authenticated by Zhang Ji, chief pharmacist of Beijing University of Chinese Medicine. The origin of the above samples is shown in Table 2.

TABLE 2

Sample information

| No. | Species | Origin | Characteristic |
|---|---|---|---|
| DS 1 | Salviae miltiorrhiza Bunge | Shandong | Medical material |
| DS 2 | Salviae miltiorrhiza Bunge | Shandong | Medical material |
| DS 3 | Salviae miltiorrhiza Bunge | Shandong | Medical material |
| DS 4 | Salviae miltiorrhiza Bunge | Shandong | Medical material |
| DS 5 | Salviae miltiorrhiza Bunge | Shandong | Medical material |
| DS 6 | Salviae miltiorrhiza Bunge | Shandong | Medical material |
| DS 7 | Salviae miltiorrhiza Bunge | Shandong | Medical material |
| DS 8 | Salviae miltiorrhiza Bunge | Sichuan | Medical material |
| DS 9 | Salviae miltiorrhiza Bunge | Sichuan | Medical material |
| DS 10 | Salviae miltiorrhiza Bunge | Sichuan | Medical material |
| DS 11 | Salviae miltiorrhiza Bunge | Sichuan | Medical material |
| DS 12 | Salviae miltiorrhiza Bunge | Sichuan | Medical material |
| DS 13 | Salviae miltiorrhiza Bunge | Shanxi | Medical material |
| DS 14 | Salviae miltiorrhiza Bunge | Shanxi | Medical material |
| DS 15 | Salviae miltiorrhiza Bunge | Shanxi | Medical material |
| DS 16 | Salviae miltiorrhiza Bunge | Shanxi | Medical material |
| DS 17 | Salviae miltiorrhiza Bunge | Henan | Medical material |
| DS 18 | Salviae miltiorrhiza Bunge | Henan | Medical material |
| DS 19 | Salviae miltiorrhiza Bunge | Henan | Medical material |
| DS 20 | Salviae miltiorrhiza Bunge | Henan | Medical material |
| DS 21 | Salviae miltiorrhiza Bunge | Henan | Medical material |
| DS 22 | Salviae miltiorrhiza Bunge | Henan | Medical material |
| DS 23 | Salviae miltiorrhiza Bunge | Henan | Medical material |
| DS 24 | Salviae miltiorrhiza Bunge | Hubei | Medical material |
| DS 25 | Salviae miltiorrhiza Bunge | Hubei | Medical material |
| DS 26 | Salviae miltiorrhiza Bunge | Hubei | Medical material |
| DS 27 | Salviae miltiorrhiza Bunge | Hubei | Medical material |
| DS 28 | Salviae miltiorrhiza Bunge | Hubei | Medical material |
| DS 29 | Salviae miltiorrhiza Bunge | Hebei | Medical material |
| DS 30 | Salviae miltiorrhiza Bunge | Hebei | Medical material |
| DS 31 | Salviae miltiorrhiza Bunge | Hebei | Medical material |
| DS 32 | Salviae miltiorrhiza Bunge | Anhui | Medical material |
| DS 33 | Salviae miltiorrhiza Bunge | Anhui | Medical material |
| DS 34 | Salviae miltiorrhiza Bunge | Anhui | Medical material |
| DS 35 | Salviae miltiorrhiza Bunge | Anhui | Medical material |
| DS 36 | Salviae miltiorrhiza Bunge | Anhui | Medical material |
| DS 37 | Salviae miltiorrhiza Bunge | Yunnan | Medical material |
| DS 38 | Salviae miltiorrhiza Bunge | Yunnan | Medical material |
| GX 39 | Salvia przewalskii Maxim. | Gansu | Medical material |
| GX 40 | Salvia przewalskii Maxim. | Gansu | Medical material |
| GX 41 | Salvia przewalskii Maxim. | Gansu | Medical material |
| GX 42 | Salvia przewalskii Maxim. | Gansu | Medical material |
| GX 43 | Salvia przewalskii Maxim. | Gansu | Medical material |
| GX 44 | Salvia przewalskii Maxim. | Gansu | Medical material |
| YN 45 | Salvia yunnanensis C. H. Wright | Yunnan | Medical material |
| YN 46 | Salvia yunnanensis C. H. Wright | Yunnan | Medical material |
| YN 47 | Salvia yunnanensis C. H. Wright | Yunnan | Medical material |
| YN 48 | Salvia yunnanensis C. H. Wright | Yunnan | Medical material |
| YN 49 | Salvia yunnanensis C. H. Wright | Yunnan | Medical material |

A method for chemical pattern recognition on authenticity of a traditional Chinese medicine, *Salviae* miltiorrhizae radix et rhizoma, specifically includes steps described below.

1. Collection of Chemical Information

Figure 2:
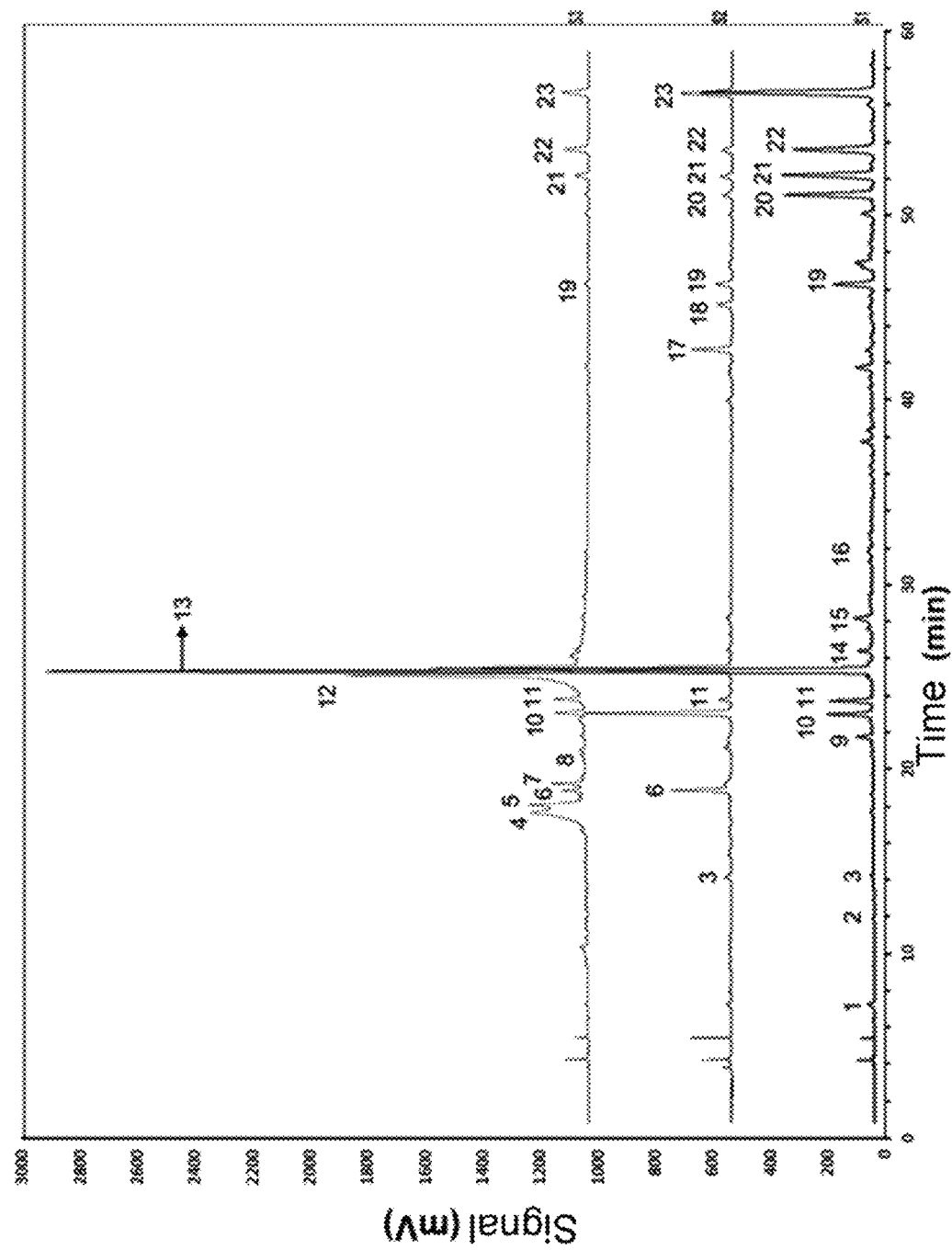
FIG. 2 is an HPLC diagram showing the results collected from Salviae miltiorrhizae radix et rhizoma, Salvia przewalskii Maxim. and Salvia yunnanensis C. H. Wright, wherein S1, S2 and S3 are HPLC results respectively for the samples of Salviae miltiorrhizae radix et rhizoma (DS3), Salvia przewalskii Maxim. (GX 39), and Salvia yunnanensis C. H. Wright (YN 45)

The 49 batches of samples were analyzed by HPLC under the conditions described above. The chromatograms were recorded and 23 peaks were selected as variable indexes. The selection principle was that any peak meeting at least one of following conditions were selected as the variable index: (I) peaks common to *Salviae* miltiorrhiizae radix et rhizoma, *Salvia przewalskii* Maxim. and *Salvia yunnanensis* C. H. Wright. (II) peaks respectively specific to *Salviae* miltiorrhizae radix et rhizoma, *Salvia przewalskii* Maxim. and *Salvia yunnanensis* C. H. Wright, and (III) peaks with high content of components. Therefore, the 23 peak variables represented the main chemical information of these three medicinal materials were selected. The selected chromatographic peaks were shown in FIG. 2, wherein S1, S2 and S3 are HPLC chromatograms collected respectively from sample DS3 (a sample of *Salviae* miltiorrhizae radix et rhizoma), sample GX 39 (a sample of *Salvia przewalskii* Maxim.), and sample YN 45 (a sample of *Salvia yunnanensis* C. H. Wright). The corresponding numbers of the selected peaks were marked in the HPLC chromatograms of the three samples.

The results of the 23 peak areas from the 49 batches of samples are shown in Table 3-1 and Table 3-2.

TABLE 3-1

|  | A1 | A2 | A3 | A4 | A5 | A6 | A7 | A8 | A9 | A10 | A11 | A12 |
| --- | --- | --- | --- | --- | --- | --- | --- | --- | --- | --- | --- | --- |
| DS 1 | 154 | 45 | 135 | 42 | 0 | 0 | 0 | 0 | 0 | 1546 | 1456 | 244 |
| DS 2 | 211 | 31 | 130 | 52 | 0 | 0 | 0 | 0 | 0 | 1781 | 1440 | 211 |
| DS 3 | 190 | 40 | 102 | 62 | 0 | 150 | 0 | 18 | 0 | 2886 | 1547 | 173 |
| DS 4 | 199 | 36 | 144 | 0 | 0 | 0 | 0 | 18 | 0 | 1412 | 1312 | 197 |
| DS 5 | 92 | 20 | 131 | 0 | 0 | 0 | 0 | 0 | 55 | 2376 | 1215 | 100 |
| DS 6 | 66 | 9 | 43 | 0 | 0 | 0 | 16 | 0 | 0 | 2401 | 902 | 171 |
| DS 7 | 297 | 126 | 70 | 0 | 0 | 223 | 0 | 50 | 150 | 2446 | 745 | 153 |
| DS 8 | 152 | 31 | 154 | 0 | 21 | 12 | 12 | 0 | 0 | 2451 | 1205 | 233 |
| DS 9 | 194 | 53 | 145 | 0 | 0 | 0 | 0 | 0 | 0 | 2755 | 2483 | 444 |
| DS 10 | 203 | 51 | 138 | 0 | 49 | 0 | 0 | 26 | 47 | 2184 | 1812 | 199 |
| DS 11 | 214 | 39 | 69 | 30 | 0 | 133 | 0 | 33 | 0 | 1768 | 1774 | 242 |
| DS 12 | 132 | 56 | 104 | 21 | 32 | 0 | 0 | 0 | 0 | 2451 | 2113 | 234 |
| DS 13 | 251 | 77 | 135 | 0 | 101 | 0 | 0 | 52 | 203 | 4049 | 3704 | 221 |
| DS 14 | 172 | 53 | 90 | 0 | 0 | 256 | 0 | 18 | 63 | 2141 | 2344 | 100 |
| DS 15 | 156 | 65 | 81 | 0 | 0 | 0 | 0 | 0 | 0 | 2354 | 2251 | 214 |
| DS 16 | 165 | 19 | 35 | 0 | 0 | 0 | 33 | 0 | 0 | 4169 | 2508 | 291 |
| DS 17 | 154 | 25 | 65 | 0 | 0 | 0 | 0 | 0 | 0 | 1254 | 1658 | 152 |
| DS 18 | 89 | 54 | 85 | 0 | 0 | 0 | 0 | 0 | 0 | 1564 | 1782 | 104 |
| DS 19 | 132 | 15 | 65 | 0 | 0 | 0 | 0 | 0 | 0 | 2543 | 1962 | 106 |
| DS 20 | 154 | 46 | 58 | 0 | 0 | 0 | 0 | 0 | 78 | 2354 | 2104 | 132 |
| DS 21 | 154 | 54 | 89 | 0 | 0 | 0 | 0 | 0 | 0 | 1245 | 1547 | 174 |
| DS 22 | 78 | 25 | 65 | 0 | 0 | 0 | 0 | 0 | 0 | 1350 | 952 | 168 |
| DS 23 | 68 | 14 | 42 | 0 | 0 | 0 | 24 | 0 | 0 | 1237 | 853 | 155 |
| DS 24 | 124 | 15 | 85 | 0 | 0 | 0 | 0 | 0 | 0 | 1546 | 1025 | 145 |
| DS 25 | 154 | 64 | 38 | 0 | 0 | 0 | 0 | 0 | 0 | 2145 | 1542 | 151 |
| DS 26 | 147 | 52 | 48 | 0 | 23 | 0 | 0 | 0 | 0 | 2354 | 2157 | 105 |
| DS 27 | 85 | 26 | 25 | 0 | 0 | 0 | 0 | 0 | 24 | 1564 | 1059 | 178 |
| DS 28 | 95 | 35 | 66 | 0 | 0 | 0 | 0 | 0 | 0 | 1254 | 1586 | 264 |
| DS 29 | 126 | 45 | 97 | 0 | 0 | 12 | 0 | 0 | 0 | 1256 | 1746 | 284 |
| DS 30 | 145 | 51 | 67 | 0 | 0 | 0 | 0 | 0 | 0 | 2549 | 1358 | 247 |
| DS 31 | 258 | 44 | 97 | 0 | 0 | 0 | 0 | 51 | 0 | 2035 | 1052 | 254 |
| DS 32 | 165 | 55 | 79 | 0 | 0 | 0 | 0 | 0 | 0 | 2147 | 1486 | 245 |
| DS 33 | 184 | 67 | 89 | 0 | 0 | 0 | 0 | 0 | 0 | 1541 | 2464 | 285 |
| DS 34 | 156 | 15 | 59 | 0 | 0 | 0 | 56 | 0 | 0 | 1264 | 2654 | 246 |
| DS 35 | 135 | 64 | 98 | 0 | 0 | 0 | 0 | 0 | 0 | 1567 | 2215 | 215 |
| DS 36 | 146 | 84 | 95 | 0 | 0 | 0 | 0 | 0 | 0 | 1458 | 2054 | 106 |
| DS 37 | 182 | 15 | 154 | 0 | 0 | 0 | 0 | 0 | 0 | 1564 | 2150 | 154 |
| DS 38 | 125 | 14 | 102 | 0 | 0 | 0 | 0 | 0 | 0 | 2514 | 2651 | 105 |
| GX 39 | 133 | 22 | 236 | 0 | 123 | 2213 | 0 | 20 | 0 | 5325 | 481 | 59 |
| GX 40 | 238 | 47 | 524 | 63 | 0 | 3467 | 0 | 0 | 0 | 11222 | 174 | 32 |
| GX 41 | 160 | 17 | 483 | 0 | 0 | 3628 | 0 | 0 | 0 | 11314 | 105 | 22 |
| GX 42 | 112 | 29 | 214 | 0 | 0 | 2123 | 0 | 0 | 0 | 3584 | 84 | 11 |
| GX 43 | 124 | 10 | 319 | 0 | 0 | 1892 | 0 | 0 | 0 | 3877 | 66 | 10 |
| GX 44 | 73 | 73 | 310 | 0 | 0 | 3188 | 0 | 4 | 0 | 11665 | 403 | 24 |
| YN 45 | 190 | 215 | 0 | 6575 | 5218 | 2639 | 3456 | 0 | 4212 | 2405 | 2941 | 18224 |
| YN 46 | 116 | 61 | 0 | 2668 | 1932 | 1359 | 1513 | 0 | 656 | 720 | 919 | 5404 |
| YN 47 | 129 | 67 | 0 | 5453 | 3392 | 1157 | 1145 | 0 | 1457 | 1295 | 1484 | 11620 |
| YN 48 | 177 | 83 | 0 | 13843 | 1246 | 3450 | 1407 | 0 | 4872 | 4064 | 3095 | 21644 |
| YN 49 | 84 | 93 | 0 | 9153 | 5871 | 1853 | 1306 | 0 | 951 | 1411 | 2067 | 20459 |

TABLE 3-2

|  | A13 | A14 | A15 | A16 | A17 | A18 | A19 | A20 | A21 | A22 | A23 |
| --- | --- | --- | --- | --- | --- | --- | --- | --- | --- | --- | --- |
| DS 1 | 26487 | 654 | 0 | 156 | 0 | 0 | 1567 | 1546 | 1564 | 1564 | 5641 |
| DS 2 | 29602 | 541 | 0 | 238 | 0 | 0 | 1993 | 4444 | 4535 | 4178 | 8596 |
| DS 3 | 36433 | 942 | 14 | 105 | 0 | 0 | 1137 | 2091 | 2110 | 2104 | 5308 |
| DS 4 | 25327 | 546 | 0 | 157 | 0 | 0 | 1058 | 2277 | 2877 | 2907 | 5733 |
| DS 5 | 30971 | 930 | 0 | 135 | 0 | 0 | 610 | 1078 | 1306 | 1669 | 3129 |
| DS 6 | 31423 | 658 | 0 | 83 | 0 | 0 | 288 | 782 | 436 | 910 | 366 |
| DS 7 | 28441 | 1238 | 0 | 116 | 0 | 0 | 485 | 1041 | 1029 | 1058 | 1373 |
| DS 8 | 24872 | 456 | 0 | 45 | 0 | 0 | 526 | 954 | 784 | 1051 | 1230 |
| DS 9 | 34688 | 1404 | 0 | 179 | 0 | 0 | 404 | 718 | 612 | 861 | 2266 |
| DS 10 | 31413 | 784 | 0 | 78 | 0 | 0 | 427 | 784 | 550 | 848 | 3789 |
| DS 11 | 31081 | 882 | 0 | 64 | 0 | 0 | 104 | 229 | 292 | 535 | 1737 |
| DS 12 | 31546 | 1045 | 0 | 51 | 0 | 0 | 326 | 524 | 654 | 2564 | 5123 |
| DS 13 | 30814 | 1628 | 0 | 160 | 0 | 0 | 1504 | 1901 | 2265 | 1756 | 4112 |
| DS 14 | 19267 | 1137 | 35 | 218 | 24 | 0 | 407 | 2251 | 465 | 4561 | 1546 |
| DS 15 | 30154 | 1024 | 0 | 215 | 0 | 0 | 526 | 2141 | 489 | 3244 | 1525 |

TABLE 3-2-continued

|       | A13   | A14  | A15 | A16 | A17 | A18  | A19  | A20  | A21  | A22  | A23  |
|-------|-------|------|-----|-----|-----|------|------|------|------|------|------|
| DS 16 | 32949 | 1324 | 0   | 126 | 0   | 0    | 1347 | 1793 | 2008 | 3071 | 4699 |
| DS 17 | 32514 | 841  | 0   | 152 | 0   | 0    | 654  | 1076 | 625  | 2154 | 1931 |
| DS 18 | 30658 | 524  | 0   | 65  | 0   | 0    | 631  | 915  | 454  | 2605 | 1496 |
| DS 19 | 30154 | 545  | 0   | 45  | 0   | 56   | 562  | 485  | 457  | 2604 | 2959 |
| DS 20 | 31524 | 641  | 0   | 54  | 0   | 0    | 456  | 174  | 587  | 3025 | 986  |
| DS 21 | 34587 | 125  | 0   | 105 | 0   | 0    | 487  | 1152 | 954  | 2648 | 3643 |
| DS 22 | 36258 | 215  | 0   | 104 | 0   | 0    | 457  | 3278 | 654  | 2615 | 3009 |
| DS 23 | 29663 | 669  | 0   | 125 | 0   | 0    | 471  | 127  | 699  | 4518 | 791  |
| DS 24 | 32501 | 545  | 0   | 134 | 0   | 0    | 425  | 94   | 356  | 6548 | 594  |
| DS 25 | 31650 | 658  | 0   | 154 | 0   | 0    | 461  | 86   | 265  | 1562 | 695  |
| DS 26 | 35462 | 784  | 0   | 210 | 0   | 0    | 514  | 461  | 568  | 4862 | 1505 |
| DS 27 | 32548 | 584  | 0   | 215 | 0   | 0    | 523  | 269  | 569  | 1546 | 1366 |
| DS 28 | 36254 | 854  | 0   | 203 | 0   | 0    | 568  | 197  | 956  | 2658 | 664  |
| DS 29 | 35021 | 658  | 0   | 215 | 0   | 0    | 578  | 155  | 786  | 2467 | 806  |
| DS 30 | 34210 | 1045 | 0   | 247 | 0   | 0    | 804  | 322  | 487  | 2316 | 1558 |
| DS 31 | 32016 | 1026 | 0   | 86  | 0   | 0    | 651  | 2067 | 982  | 2851 | 4524 |
| DS 32 | 31542 | 852  | 0   | 59  | 0   | 0    | 425  | 811  | 869  | 3116 | 4126 |
| DS 33 | 31541 | 862  | 0   | 84  | 0   | 0    | 653  | 1584 | 873  | 1968 | 7149 |
| DS 34 | 29858 | 954  | 0   | 116 | 0   | 0    | 542  | 277  | 958  | 2416 | 1600 |
| DS 35 | 28514 | 854  | 0   | 85  | 0   | 0    | 457  | 463  | 645  | 2561 | 997  |
| DS 36 | 26584 | 786  | 0   | 64  | 0   | 0    | 523  | 532  | 798  | 2391 | 2109 |
| DS 37 | 25841 | 729  | 0   | 75  | 0   | 0    | 546  | 804  | 659  | 2860 | 2784 |
| DS 38 | 26547 | 831  | 0   | 98  | 0   | 0    | 526  | 641  | 815  | 4502 | 2037 |
| GX 39 | 8650  | 34   | 29  | 23  | 226 | 754  | 759  | 479  | 541  | 456  | 2562 |
| GX 40 | 2503  | 47   | 60  | 37  | 950 | 2047 | 641  | 922  | 1303 | 675  | 5770 |
| GX 41 | 2022  | 32   | 0   | 45  | 468 | 1842 | 454  | 973  | 970  | 756  | 6142 |
| GX 42 | 1095  | 50   | 0   | 0   | 767 | 1196 | 468  | 604  | 683  | 412  | 1289 |
| GX 43 | 815   | 18   | 0   | 10  | 196 | 325  | 179  | 204  | 251  | 158  | 672  |
| GX 44 | 6649  | 181  | 61  | 129 | 0   | 3651 | 532  | 1614 | 1274 | 1562 | 6663 |
| YN 45 | 9006  | 0    | 0   | 0   | 0   | 18   | 114  | 123  | 489  | 1310 | 1013 |
| YN 46 | 3782  | 0    | 0   | 0   | 0   | 0    | 70   | 48   | 197  | 329  | 447  |
| YN 47 | 5314  | 0    | 0   | 0   | 0   | 0    | 164  | 116  | 626  | 1214 | 1352 |
| YN 48 | 17404 | 0    | 0   | 0   | 13  | 76   | 220  | 102  | 718  | 1556 | 1142 |
| YN 49 | 7691  | 0    | 0   | 0   | 0   | 0    | 150  | 56   | 294  | 426  | 291  |

2. Normalization of the Data

In the process of multivariate statistical analysis, data of different dimensions often need to be collected, and variables are different in the order of magnitude and unit of measure, which makes the variables unable to be comprehensively investigated. The multivariate statistical analysis has special requirements for variables, for example, it requires that variables are in normal distribution or are comparable with each other. In this case, the value of each variable needs to be normalized by using a certain method. When the original data is normally distributed, they need to be dimensionlessly processed by using the Z-normalized method, which is one of the most widely used methods for the multivariable comprehensive analysis.

Since the values of different peak areas in the measurement results of this experiment are quite different from each other, the Z-normalized method is used for calculation. The calculation method is shown in the following formula. The normalized data are shown in Table 4-1 and Table 4-2.

$$\text{normalized data} = \frac{\text{original data} - \text{mean value}}{\text{standard deviation}}$$

TABLE 4-1

|       | A1   | A2   | A3   | A4   | A5   | A6   | A7   | A8   | A9   | A10  | A11  | A12  |
|-------|------|------|------|------|------|------|------|------|------|------|------|------|
| DS 1  | 0.0  | −0.1 | 0.2  | −0.3 | −0.3 | −0.5 | −0.3 | −0.4 | −0.3 | −0.5 | −0.2 | −0.3 |
| DS 2  | 1.2  | −0.5 | 0.2  | −0.3 | −0.3 | −0.5 | −0.3 | −0.4 | −0.3 | −0.4 | −0.2 | −0.3 |
| DS 3  | 0.8  | −0.2 | −0.1 | −0.3 | −0.3 | −0.4 | −0.3 | 0.9  | −0.3 | 0.1  | −0.1 | −0.3 |
| DS 4  | 0.9  | −0.3 | 0.3  | −0.3 | −0.3 | −0.5 | −0.3 | 0.9  | −0.3 | −0.6 | −0.4 | −0.3 |
| DS 5  | −1.2 | −0.8 | 0.2  | −0.3 | −0.3 | −0.5 | −0.3 | −0.4 | −0.2 | −0.2 | −0.5 | −0.3 |
| DS 6  | −1.7 | −1.1 | −0.6 | −0.3 | −0.3 | −0.5 | −0.3 | −0.4 | −0.3 | −0.1 | −0.9 | −0.3 |
| DS 7  | 2.9  | 2.3  | −0.4 | −0.3 | −0.3 | −0.3 | −0.3 | 3.2  | −0.1 | −0.1 | −1.1 | −0.3 |
| DS 8  | 0.0  | −0.5 | 0.4  | −0.3 | −0.3 | −0.5 | −0.3 | −0.4 | −0.3 | −0.1 | −0.5 | −0.3 |
| DS 9  | 0.8  | 0.2  | 0.3  | −0.3 | −0.3 | −0.5 | −0.3 | −0.4 | −0.3 | 0.0  | 1.1  | −0.3 |
| DS 10 | 1.0  | 0.1  | 0.3  | −0.3 | −0.3 | −0.5 | −0.3 | 1.5  | −0.2 | −0.2 | 0.3  | −0.3 |
| DS 11 | 1.2  | −0.3 | −0.4 | −0.3 | −0.3 | −0.4 | −0.3 | 2.0  | −0.3 | −0.4 | 0.2  | −0.3 |
| DS 12 | −0.4 | 0.2  | −0.1 | −0.3 | −0.3 | −0.5 | −0.3 | −0.4 | −0.3 | −0.1 | 0.6  | −0.3 |
| DS 13 | 2.0  | 0.8  | 0.2  | −0.3 | −0.2 | −0.5 | −0.3 | 3.3  | −0.1 | 0.5  | 2.6  | −0.3 |
| DS 14 | 0.4  | 0.2  | −0.2 | −0.3 | −0.3 | −0.5 | −0.3 | 0.9  | −0.2 | −0.3 | 0.9  | −0.3 |
| DS 15 | 0.1  | 0.5  | −0.3 | −0.3 | −0.3 | −0.5 | −0.3 | −0.4 | −0.3 | −0.2 | 0.8  | −0.3 |
| DS 16 | 0.3  | −0.8 | −0.7 | −0.3 | −0.3 | −0.5 | −0.3 | −0.4 | −0.3 | 0.6  | 1.1  | −0.3 |
| DS 17 | 0.0  | −0.7 | −0.4 | −0.3 | −0.3 | −0.5 | −0.3 | −0.4 | −0.3 | −0.6 | 0.1  | −0.3 |
| DS 18 | −1.2 | 0.2  | −0.3 | −0.3 | −0.3 | −0.5 | −0.3 | −0.4 | −0.3 | −0.5 | 0.2  | −0.3 |
| DS 19 | −0.4 | −1.0 | −0.4 | −0.3 | −0.3 | −0.5 | −0.3 | −0.4 | −0.3 | −0.1 | 0.4  | −0.3 |
| DS 20 | 0.0  | −0.1 | −0.5 | −0.3 | −0.3 | −0.5 | −0.3 | −0.4 | −0.2 | −0.2 | 0.6  | −0.3 |

TABLE 4-1-continued

|       | A1   | A2   | A3   | A4   | A5   | A6   | A7   | A8   | A9   | A10  | A11  | A12  |
|-------|------|------|------|------|------|------|------|------|------|------|------|------|
| DS 21 | 0.0  | 0.2  | −0.2 | −0.3 | −0.3 | −0.5 | −0.3 | −0.4 | −0.3 | −0.6 | −0.1 | −0.3 |
| DS 22 | −1.5 | −0.7 | −0.4 | −0.3 | −0.3 | −0.5 | −0.3 | −0.4 | −0.3 | −0.6 | −0.8 | −0.3 |
| DS 23 | −1.7 | −1.0 | −0.7 | −0.3 | −0.3 | −0.5 | −0.3 | −0.4 | −0.3 | −0.6 | −0.9 | −0.3 |
| DS 24 | −0.6 | −1.0 | −0.3 | −0.3 | −0.3 | −0.5 | −0.3 | −0.4 | −0.3 | −0.5 | −0.7 | −0.3 |
| DS 25 | 0.0  | 0.5  | −0.7 | −0.3 | −0.3 | −0.5 | −0.3 | −0.4 | −0.3 | −0.3 | −0.1 | −0.3 |
| DS 26 | −0.1 | 0.1  | −0.6 | −0.3 | −0.3 | −0.5 | −0.3 | −0.4 | −0.3 | −0.2 | 0.7  | −0.3 |
| DS 27 | −1.3 | −0.6 | −0.8 | −0.3 | −0.3 | −0.5 | −0.3 | −0.4 | −0.3 | −0.5 | −0.7 | −0.3 |
| DS 28 | −1.1 | −0.4 | −0.4 | −0.3 | −0.3 | −0.5 | −0.3 | −0.4 | −0.3 | −0.6 | 0.0  | −0.3 |
| DS 29 | −0.5 | −0.1 | −0.1 | −0.3 | −0.3 | −0.5 | −0.3 | −0.4 | −0.3 | −0.6 | 0.2  | −0.3 |
| DS 30 | −0.1 | 0.1  | −0.4 | −0.3 | −0.3 | −0.5 | −0.3 | −0.4 | −0.3 | −0.1 | −0.3 | −0.3 |
| DS 31 | 2.1  | −0.1 | −0.1 | −0.3 | −0.3 | −0.5 | −0.3 | 3.3  | −0.3 | −0.3 | −0.7 | −0.3 |
| DS 32 | 0.3  | 0.2  | −0.3 | −0.3 | −0.3 | −0.5 | −0.3 | −0.4 | −0.3 | −0.3 | −0.2 | −0.3 |
| DS 33 | 0.6  | 0.6  | −0.2 | −0.3 | −0.3 | −0.5 | −0.3 | −0.4 | −0.3 | −0.5 | 1.1  | −0.3 |
| DS 34 | 0.1  | −1.0 | −0.5 | −0.3 | −0.3 | −0.5 | −0.2 | −0.4 | −0.3 | −0.6 | 1.3  | −0.3 |
| DS 35 | −0.3 | 0.5  | −0.1 | −0.3 | −0.3 | −0.5 | −0.3 | −0.4 | −0.3 | −0.5 | 0.8  | −0.3 |
| DS 36 | −0.1 | 1.0  | −0.2 | −0.3 | −0.3 | −0.5 | −0.3 | −0.4 | −0.3 | −0.5 | 0.6  | −0.3 |
| DS 37 | 0.6  | −1.0 | 0.4  | −0.3 | −0.3 | −0.5 | −0.3 | −0.4 | −0.3 | −0.5 | 0.7  | −0.3 |
| DS 38 | −0.5 | −1.0 | −0.1 | −0.3 | −0.3 | −0.5 | −0.3 | −0.4 | −0.3 | −0.1 | 1.3  | −0.3 |
| GX 39 | −0.4 | −0.8 | 1.2  | −0.3 | −0.2 | 1.5  | −0.3 | 1.0  | −0.3 | 1.1  | −1.4 | −0.3 |
| GX 40 | 1.7  | 0.0  | 3.9  | −0.3 | −0.3 | 2.6  | −0.3 | −0.4 | −0.3 | 3.5  | −1.8 | −0.3 |
| GX 41 | 0.2  | −0.9 | 3.5  | −0.3 | −0.3 | 2.8  | −0.3 | −0.4 | −0.3 | 3.6  | −1.8 | −0.3 |
| GX 42 | −0.8 | −0.5 | 1.0  | −0.3 | −0.3 | 1.4  | −0.3 | −0.4 | −0.3 | 0.4  | −1.9 | −0.3 |
| GX 43 | −0.6 | −1.1 | 2.0  | −0.3 | −0.3 | 1.2  | −0.3 | −0.4 | −0.3 | 0.5  | −1.9 | −0.3 |
| GX 44 | −1.6 | 0.7  | 1.9  | −0.3 | −0.3 | 2.4  | −0.3 | −0.1 | −0.3 | 3.7  | −1.5 | −0.3 |
| YN 45 | 0.8  | 4.8  | −1.1 | 2.2  | 4.0  | 1.9  | 5.4  | −0.4 | 4.2  | −0.1 | 1.6  | 3.3  |
| YN 46 | −0.7 | 0.4  | −1.1 | 0.7  | 1.3  | 0.7  | 2.2  | −0.4 | 0.4  | −0.8 | −0.8 | 0.7  |
| YN 47 | −0.5 | 0.6  | −1.1 | 1.8  | 2.5  | 0.5  | 1.6  | −0.4 | 1.3  | −0.6 | −0.2 | 2.0  |
| YN 48 | 0.5  | 1.0  | −1.1 | 5.0  | 0.7  | 2.6  | 2.0  | −0.4 | 5.0  | 0.6  | 1.8  | 3.9  |
| YN 49 | −1.3 | 1.3  | −1.1 | 3.2  | 4.5  | 1.2  | 1.9  | −0.4 | 0.7  | −0.6 | 0.6  | 3.7  |

TABLE 4-2

|       | A13  | A14  | A15  | A16  | A17  | A18  | A19  | A20  | A21  | A22  | A23  |
|-------|------|------|------|------|------|------|------|------|------|------|------|
| DS 1  | 0.1  | 0.0  | −0.3 | 0.7  | −0.3 | −0.3 | 2.6  | 0.7  | 0.9  | −0.5 | 1.4  |
| DS 2  | 0.4  | −0.2 | −0.3 | 1.9  | −0.3 | −0.3 | 3.8  | 3.9  | 4.8  | 1.5  | 2.9  |
| DS 3  | 1.0  | 0.7  | 0.7  | 0.0  | −0.3 | −0.3 | 1.5  | 1.3  | 1.6  | −0.1 | 1.3  |
| DS 4  | 0.0  | −0.2 | −0.3 | 0.8  | −0.3 | −0.3 | 1.3  | 1.5  | 2.6  | 0.5  | 1.5  |
| DS 5  | 0.5  | 0.7  | −0.3 | 0.5  | −0.3 | −0.3 | 0.1  | 0.2  | 0.5  | −0.4 | 0.2  |
| DS 6  | 0.6  | 0.1  | −0.3 | −0.3 | −0.3 | −0.3 | −0.8 | −0.2 | −0.6 | −0.9 | −1.1 |
| DS 7  | 0.3  | 1.4  | −0.3 | 0.2  | −0.3 | −0.3 | −0.3 | 0.1  | 0.2  | −0.8 | −0.6 |
| DS 8  | 0.0  | −0.4 | −0.3 | −0.8 | −0.3 | −0.3 | −0.1 | 0.0  | −0.2 | −0.8 | −0.7 |
| DS 9  | 0.9  | 1.8  | −0.3 | 1.1  | −0.3 | −0.3 | −0.5 | −0.2 | −0.4 | −1.0 | −0.2 |
| DS 10 | 0.6  | 0.4  | −0.3 | −0.4 | −0.3 | −0.3 | −0.4 | −0.2 | −0.5 | −1.0 | 0.5  |
| DS 11 | 0.5  | 0.6  | −0.3 | −0.6 | −0.3 | −0.3 | −1.3 | −0.8 | −0.8 | −1.2 | −0.5 |
| DS 12 | 0.6  | 1.0  | −0.3 | −0.7 | −0.3 | −0.3 | −0.7 | −0.5 | −0.3 | 0.3  | 1.2  |
| DS 13 | 0.5  | 2.4  | −0.3 | 0.8  | −0.3 | −0.3 | 2.5  | 1.1  | 1.8  | −0.3 | 0.7  |
| DS 14 | −0.5 | 1.2  | 2.3  | 1.6  | −0.2 | −0.3 | −0.5 | 1.5  | −0.6 | 1.8  | −0.5 |
| DS 15 | 0.4  | 0.9  | −0.3 | 1.6  | −0.3 | −0.3 | −0.1 | 1.3  | −0.6 | 0.8  | −0.6 |
| DS 16 | 0.7  | 1.6  | −0.3 | 0.3  | −0.3 | −0.3 | 2.0  | 1.0  | 1.5  | 0.7  | 1.0  |
| DS 17 | 0.7  | 0.5  | −0.3 | 0.7  | −0.3 | −0.3 | 0.2  | 0.2  | −0.4 | 0.0  | −0.4 |
| DS 18 | 0.5  | −0.3 | −0.3 | −0.5 | −0.3 | −0.3 | 0.1  | 0.0  | −0.6 | 0.3  | −0.6 |
| DS 19 | 0.4  | −0.2 | −0.3 | −0.8 | −0.3 | −0.2 | −0.1 | −0.5 | −0.6 | 0.3  | 0.1  |
| DS 20 | 0.6  | 0.0  | −0.3 | −0.7 | −0.3 | −0.3 | −0.3 | −0.8 | −0.4 | 0.6  | −0.8 |
| DS 21 | 0.8  | −1.2 | −0.3 | 0.0  | −0.3 | −0.3 | −0.2 | 0.2  | 0.1  | 0.4  | 0.5  |
| DS 22 | 1.0  | −1.0 | −0.3 | 0.0  | −0.3 | −0.3 | −0.3 | 2.6  | −0.3 | 0.3  | 0.2  |
| DS 23 | 0.4  | 0.1  | −0.3 | 0.3  | −0.3 | −0.3 | −0.3 | −0.9 | −0.3 | 1.7  | −0.9 |
| DS 24 | 0.7  | −0.2 | −0.3 | 0.4  | −0.3 | −0.3 | −0.4 | −0.9 | −0.7 | 3.2  | −1.0 |
| DS 25 | 0.6  | 0.1  | −0.3 | 0.7  | −0.3 | −0.3 | −0.3 | −0.9 | −0.9 | −0.5 | −1.0 |
| DS 26 | 0.9  | 0.4  | −0.3 | 1.5  | −0.3 | −0.3 | −0.2 | −0.5 | −0.5 | 2.0  | −0.6 |
| DS 27 | 0.7  | −0.1 | −0.3 | 1.6  | −0.3 | −0.3 | −0.2 | −0.7 | −0.4 | −0.5 | −0.6 |
| DS 28 | 1.0  | 0.5  | −0.3 | 1.4  | −0.3 | −0.3 | 0.0  | −0.8 | 0.1  | 0.4  | −1.0 |
| DS 29 | 0.9  | 0.1  | −0.3 | 1.6  | −0.3 | −0.3 | 0.0  | −0.9 | −0.2 | 0.2  | −0.9 |
| DS 30 | 0.8  | 1.0  | −0.3 | 2.0  | −0.3 | −0.3 | 0.6  | −0.7 | −0.6 | 0.1  | −0.5 |
| DS 31 | 0.6  | 0.9  | −0.3 | −0.2 | −0.3 | −0.3 | 0.2  | 1.3  | 0.1  | 0.5  | 0.9  |
| DS 32 | 0.6  | 0.5  | −0.3 | −0.6 | −0.3 | −0.3 | −0.4 | −0.1 | −0.1 | 0.7  | 0.7  |
| DS 33 | 0.6  | 0.5  | −0.3 | −0.3 | −0.3 | −0.3 | 0.2  | 0.7  | 0.0  | −0.2 | 2.2  |
| DS 34 | 0.4  | 0.8  | −0.3 | 0.2  | −0.3 | −0.3 | −0.1 | −0.7 | 0.1  | 0.2  | −0.5 |
| DS 35 | 0.3  | 0.5  | −0.3 | −0.3 | −0.3 | −0.3 | −0.3 | −0.5 | −0.3 | 0.3  | −0.8 |
| DS 36 | 0.1  | 0.4  | −0.3 | −0.6 | −0.3 | −0.3 | −0.2 | −0.4 | −0.1 | 0.2  | −0.3 |
| DS 37 | 0.1  | 0.2  | −0.3 | −0.4 | −0.3 | −0.3 | −0.1 | −0.1 | −0.3 | 0.5  | 0.1  |
| DS 38 | 0.1  | 0.5  | −0.3 | −0.1 | −0.3 | −0.3 | −0.1 | −0.3 | −0.1 | 1.7  | −0.3 |
| GX 39 | −1.5 | −1.4 | 1.8  | −1.1 | 0.9  | 0.8  | 0.5  | −0.5 | −0.5 | −1.3 | −0.1 |
| GX 40 | −2.0 | −1.4 | 4.1  | −0.9 | 4.8  | 2.8  | 0.2  | 0.0  | 0.5  | −1.1 | 1.5  |

TABLE 4-2-continued

| | A13 | A14 | A15 | A16 | A17 | A18 | A19 | A20 | A21 | A22 | A23 |
|---|---|---|---|---|---|---|---|---|---|---|---|
| GX 41 | −2.1 | −1.4 | −0.3 | −0.8 | 2.2 | 2.5 | −0.3 | 0.0 | 0.1 | −1.0 | 1.7 |
| GX 42 | −2.2 | −1.4 | −0.3 | −1.5 | 3.8 | 1.5 | −0.3 | −0.4 | −0.3 | −1.3 | −0.7 |
| GX 43 | −2.2 | −1.5 | −0.3 | −1.3 | 0.8 | 0.2 | −1.1 | −0.8 | −0.9 | −1.5 | −1.0 |
| GX 44 | −1.7 | −1.1 | 4.2 | 0.4 | −0.3 | 5.2 | −0.1 | 0.8 | 0.5 | −0.5 | 1.9 |
| YN 45 | −1.5 | −1.5 | −0.3 | −1.5 | −0.3 | −0.3 | −1.2 | −0.9 | −0.6 | −0.6 | −0.8 |
| YN 46 | −1.9 | −1.5 | −0.3 | −1.5 | −0.3 | −0.3 | −1.4 | −1.0 | −0.9 | −1.4 | −1.1 |
| YN 47 | −1.8 | −1.5 | −0.3 | −1.5 | −0.3 | −0.3 | −1.1 | −0.9 | −0.4 | −0.7 | −0.6 |
| YN 48 | −0.7 | −1.5 | −0.3 | −1.5 | −0.2 | −0.2 | −1.0 | −0.9 | −0.3 | −0.5 | −0.7 |
| YN 49 | −1.6 | −1.5 | −0.3 | −1.5 | −0.3 | −0.3 | −1.1 | −1.0 | −0.8 | −1.3 | −1.1 |

3. Assay of Anti-Myocardial Ischemia Efficacy of *Salviae* Miltiorrhiizae Radix Et Rhizoma and its Counterfeits The anti-myocardial ischemia effect of 75% methanol extracts of *Salviae* miltiorrhizae radix et rhizoma were compared with that of two counterfeits with a rat myocardial cell hypoxia-reoxygenation injury model. The survival rate, lactate dehydrogenase (LDH) activity, reactive oxygen species (ROS) level, and intracellular concentration of calcium ion were measured. The results are shown in Table 5.

TABLE 5

The results of anti-myocardial ischemia efficacy of Salviae miltiorrhizae radix et rhizoma and its counterfeits

| Sample | LDH (U/L) | ROS level | Calcium ion concentration (nmol/L) |
|---|---|---|---|
| DS 1 | 33.1 | 20.4 | 146.5 |
| DS 2 | 32 | 31.3 | 129.5 |
| DS 3 | 37.7 | 20.2 | 136.5 |
| DS 4 | 36.5 | 22.4 | 135.1 |
| DS 5 | 35.2 | 32.1 | 174.2 |
| DS 6 | 38.5 | 27.9 | 152.2 |
| DS 7 | 36.5 | 23.3 | 167.2 |
| DS 8 | 33.6 | 31.2 | 152.4 |
| DS 9 | 34.5 | 30.5 | 178.1 |
| DS 10 | 36.2 | 22.4 | 152.4 |
| DS 11 | 36.6 | 19.6 | 145.7 |
| DS 12 | 37.9 | 21.4 | 142.5 |
| DS 13 | 36.2 | 24 | 158.4 |
| DS 14 | 36.5 | 29.3 | 147.5 |
| DS 15 | 35.2 | 26.4 | 134 |
| DS 16 | 35.4 | 29.4 | 171.4 |
| DS 17 | 35.3 | 26.9 | 124.8 |
| DS 18 | 35.2 | 28.6 | 142.1 |
| DS 19 | 34.5 | 29.1 | 157.8 |
| DS 20 | 40.2 | 19.5 | 130.5 |
| DS 21 | 44.6 | 19.8 | 152.3 |
| DS 22 | 42.8 | 21.5 | 154.2 |
| DS 23 | 44.7 | 22.4 | 165.2 |
| DS 24 | 44.1 | 23.4 | 159.2 |
| DS 25 | 42 | 28.1 | 184.2 |
| DS 26 | 44.5 | 33.4 | 194.1 |
| DS 27 | 41.2 | 32.5 | 175.2 |
| DS 28 | 40 | 22.2 | 176.8 |
| DS 29 | 41 | 31.9 | 160.8 |
| DS 30 | 44.3 | 19.2 | 167.2 |
| DS 31 | 44.8 | 18.9 | 187.4 |
| DS 32 | 32.7 | 19.2 | 146.2 |
| DS 33 | 33.2 | 19.2 | 158.9 |
| DS 34 | 33.2 | 21.1 | 154.2 |
| DS 35 | 34.3 | 24.5 | 140.5 |
| DS 36 | 34.2 | 26.4 | 162.7 |
| DS 37 | 30.4 | 24.2 | 154.2 |
| DS 38 | 33.9 | 31.5 | 195.5 |
| GX 39 | 44.8 | 28 | 184.2 |
| GX 40 | 43.4 | 35.6 | 178.2 |
| GX 41 | 32.6 | 27.4 | 181.3 |
| GX 42 | 34.7 | 26.7 | 191.4 |
| GX 43 | 35.3 | 28.6 | 185.1 |
| GX 44 | 33.6 | 30.4 | 179.2 |

TABLE 5-continued

The results of anti-myocardial ischemia efficacy of Salviae miltiorrhizae radix et rhizoma and its counterfeits

| Sample | LDH (U/L) | ROS level | Calcium ion concentration (nmol/L) |
|---|---|---|---|
| YN 45 | 36.3 | 33.5 | 192.2 |
| YN 46 | 32.6 | 32.5 | 186.5 |
| YN 47 | 34.1 | 32.9 | 185.2 |
| YN 48 | 42.6 | 29 | 175.4 |
| YN 49 | 34.5 | 26.9 | 158.2 |

4. Spectrum-Effect Correlation Analysis

The study of the spectrum-effect relationship of the traditional Chinese medicine refers to that the chemical components (i.e., spectrum) is combined with the pharmacological effect (i.e., effect), to generally study the relationship between the effective chemical components of traditional Chinese medicine and the chemical effect thereof. The correlation between the pharmacodynamics information and HPLC fingerprint data of the 49 batches of traditional Chinese medicines was investigated by the bivariate correlation analysis. The results are shown in Table 6.

TABLE 6

The results of the correlation analysis of medicinal effects and fingerprint data

| | Pearson correlation | | |
|---|---|---|---|
| No. | LDH (UZL) | ROS fluorescence intensity | Concentration of Calcium ion (nmol/L) |
| A1 | −0.062 | −0.19 | −0.103 |
| A2 | −0.062 | 0.112 | 0.147 |
| A3 | −0.081 | 0.167 | 0.173 |
| A4 | 0.022 | 0.238 | 0.216 |
| A5 | −0.138 | 0.281 | 0.241 |
| A6 | −0.002 | 0.403** | 0.484** |
| A7 | −0.088 | 0.331* | 0.316 |
| A8 | 0.124 | −0.323* | −0.022 |
| A9 | 0.059 | 0.264 | 0.265 |
| A10 | 0 | 0.294* | 0.327 |
| A11 | −0.184 | −0.07 | −0.219 |
| A12 | −0.022 | 0.265 | 0.238 |
| A13 | 0.234 | −0.443** | −0.475** |
| A14 | −0.075 | −0.335* | −0.312 |
| A15 | 0.121 | 0.283* | 0.136 |
| A16 | 0.196 | −0.052 | −0.236 |
| A17 | 0.08 | 0.249 | 0.322 |
| A18 | −0.058 | 0.257 | 0.305 |
| A19 | −0.098 | −0.122 | −0.326 |
| A20 | −0.162 | −0.114 | −0.397** |

TABLE 6-continued

The results of the correlation analysis
of medicinal effects and fingerprint data

| No. | Pearson correlation | | |
|---|---|---|---|
| | LDH (UZL) | ROS fluorescence intensity | Concentration of Calcium ion (nmol/L) |
| A21 | −0.204 | −0.028 | −0.3 |
| A22 | 0.228 | −0.152 | −0.25 |
| A23 | −0.225 | −0.168 | −0.212 |

**Significance level is 0.01.
*Significance level is 0.05.

It can be seen from Table 6 that the HPLC fingerprint data A6, A7, A8, A10, A13, A14, A17, A18, A19, A20, and A21, were significantly correlated with the pharmacodynamic activities of *Salviae* miltiorrhizae radix et rhizoma, *Salvia przewalskii* Maxim. and *Salvia yunnanensis* C. H. Wright.

5. Classification of Training Set and Testing Set 49 batches of samples were randomly classified into a training set and a testing set by random algorithm, and the results are shown below.

Samples of the training set were No. DS 2, DS 3, DS 4, DS 6, DS 7, DS 13, DS 15, DS 16, DS 18, DS 20, DS 22, DS 35, GX 39, GX 42, GX 43, GX 44, YN 46, YN 47, YN 48, and YN 49.

Samples of the testing set were No. DS 1, DS 5, DS 8. DS 9, DS 10, DS 11, DS 12, DS 14, DS 17, DS 19, DS 21, DS 23. DS 24, DS 25, DS 26. DS 27, DS 28, DS 29, DS 30, DS 31, DS 32, DS 33, DS 34. DS 36, DS 37, DS 38, GX 40, GX 41, and YN 45.

6. Characteristic Extraction Under Guide of the Pharmacodynamics Information

Variables significantly correlated with the medicinal effect in the results of spectrum-effect correlation analysis (i.e., variables A6, A7, A8, A10, A10, A13, A14. A17, A18, A19, A20, and A21), were screened by stepwise discriminant analysis to perform characteristic extraction. The screening was performed stepwise through F-test. In each step, the most significant variables that meet a specified level were selected, and originally introduced variables were removed which are insignificant due to the introduction of new variables, until no variable could be introduced or removed. *Salviae* miltiorrhizae radix et rhizoma, *Salvia przewalskii* Maxim. and *Salvia yunnanensis* C. H. Wright were simultaneously compared by stepwise discriminant analysis, and representative peak variables of the characteristics were screened. The dimension reduction results (i.e., the screened characteristic variables) are shown in Table 7.

TABLE 7

Groups and characteristic peaks of samples

| Group | Peak |
|---|---|
| Salviae miltiorrhizae radix et rhizoma vs. *Salvia przewalskii* Maxim. vs. *Salvia yunnanensis* C. H. Wright (three peaks) | A6, A7, A13 |

7. Establishment of Discriminant Functions of a Pattern Recognition Model

The characteristic variables selected by stepwise discriminant analysis and discriminant coefficients are shown in Table 8, and two established discriminant functions are shown below.

TABLE 8

Typical discriminant function coefficient

| | Function | |
|---|---|---|
| | 1 | 9 |
| A6 | 0.492 | −2.571 |
| A7 | 8.762 | 4.521 |
| A13 | −1.249 | 3.277 |
| Constant | −1.869 | 1.288 |

$F_1 = 0.492X_6 + 8.762X_7 - 1.249X_{13} - 1.869$
$F_2 = -2.571X_6 + 4.521X_7 + 3.277X_{13} + 1.288$

8. Model Validation (1) Internal validation of the model. The model was validated by Leave-one-out internal cross-validation. Results demonstrate that in the model established as above, the accuracy of the discrimination with the leave-one-out internal cross-validation was 100%.

(2) The testing set was used for the external validation of the model, and the characteristic peaks of the samples in the testing set were brought into the discriminant function, to obtain discriminant scores and discriminant classification results of the samples. The results are shown in Table 9. The discriminant results of the model were consistent with the results of the character identification, and the accuracy of the discrimination is 100%.

TABLE 9

The discriminant results of the samples in the testing set

| Sample No. | F1 | F2 | Results | True or False |
|---|---|---|---|---|
| DS1 | −4.87 | 1.54 | *Salviae miltiorrhiza* Bunge | True |
| DS5 | −5.37 | 2.85 | *Salviae miltiorrhiza* Bunge | True |
| DS8 | −4.74 | 1.22 | *Salviae miltiorrhiza* Bunge | True |
| DS9 | −5.87 | 4.16 | *Salviae miltiorrhiza* Bunge | True |
| DS10 | −5.49 | 3.18 | *Salviae miltiorrhiza* Bunge | True |
| DS11 | −5.32 | 2.60 | *Salviae miltiorrhiza* Bunge | True |
| DS12 | −5.49 | 3.18 | *Salviae miltiorrhiza* Bunge | True |
| DS14 | −4.02 | −0.94 | *Salviae miltiorrhiza* Bunge | True |
| DS17 | −5.62 | 3.51 | *Salviae miltiorrhiza* Bunge | True |
| DS19 | −5.24 | 2.53 | *Salviae miltiorrhiza* Bunge | True |
| DS21 | −5.74 | 3.84 | *Salviae miltiorrhiza* Bunge | True |
| DS23 | −5.24 | 2.53 | *Salviae miltiorrhiza* Bunge | True |
| DS24 | −5.62 | 3.51 | *Salviae miltiorrhiza* Bunge | True |
| DS25 | −5.49 | 3.18 | *Salviae miltiorrhiza* Bunge | True |
| DS26 | −5.87 | 4.16 | *Salviae miltiorrhiza* Bunge | True |
| DS27 | −5.62 | 3.51 | *Salviae miltiorrhiza* Bunge | True |
| DS28 | −5.99 | 4.49 | *Salviae miltiorrhiza* Bunge | True |
| DS29 | −5.87 | 4.16 | *Salviae miltiorrhiza* Bunge | True |
| DS30 | −5.74 | 3.84 | *Salviae miltiorrhiza* Bunge | True |
| DS31 | −5.49 | 3.18 | *Salviae miltiorrhiza* Bunge | True |
| DS32 | −5.49 | 3.18 | *Salviae miltiorrhiza* Bunge | True |

TABLE 9-continued

The discriminant results of the samples in the testing set

| Sample No. | F1 | F2 | Results | True or False |
|---|---|---|---|---|
| DS33 | −5.49 | 3.18 | Salviae miltiorrhiza Bunge | True |
| DS34 | −4.37 | 2.98 | Salviae miltiorrhiza Bunge | True |
| DS36 | −4.87 | 1.54 | Salviae miltiorrhiza Bunge | True |
| DS37 | −4.87 | 1.54 | Salviae miltiorrhiza Bunge | True |
| DS38 | −4.87 | 1.54 | Salviae miltiorrhiza Bunge | True |
| GX40 | −0.72 | −13.31 | Salvia przewalskii Maxim. | True |
| GX41 | −0.50 | −14.15 | Salvia przewalskii Maxim. | True |
| YN45 | 48.25 | 15.90 | Salvia yunnanensis C. H. Wright | True |

8. Visualization of the Results

Figure 3:
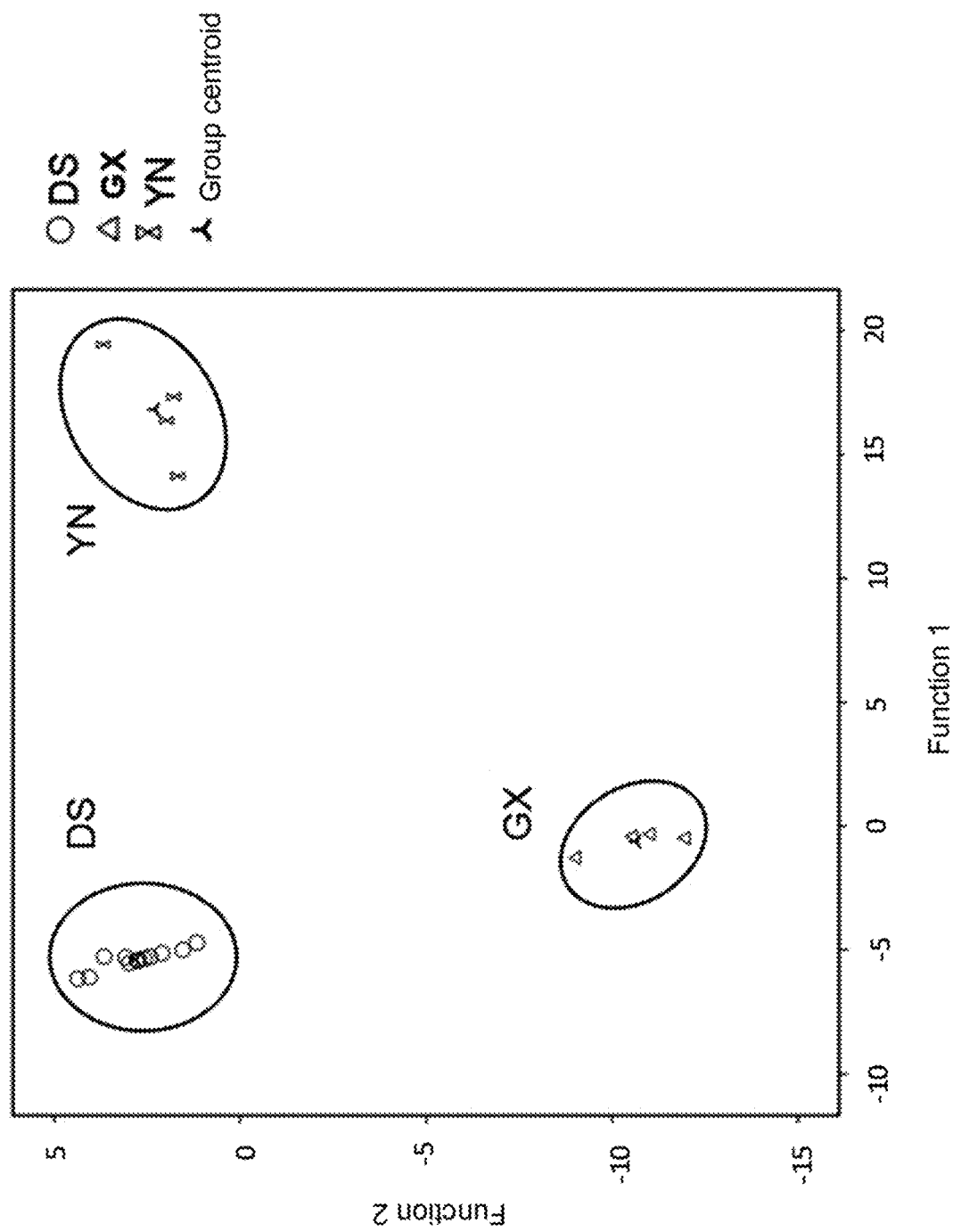
FIG. 3 is a diagram showing the distribution of samples in the training set of Salviae miltiorrhizae radix et rhizoma and counterfeits thereof, with values of discnminant functions (values of $F_1$ and $F_2$, namely, function 1 and function 2) as horizontal and vertical coordinates.
Figure 4:
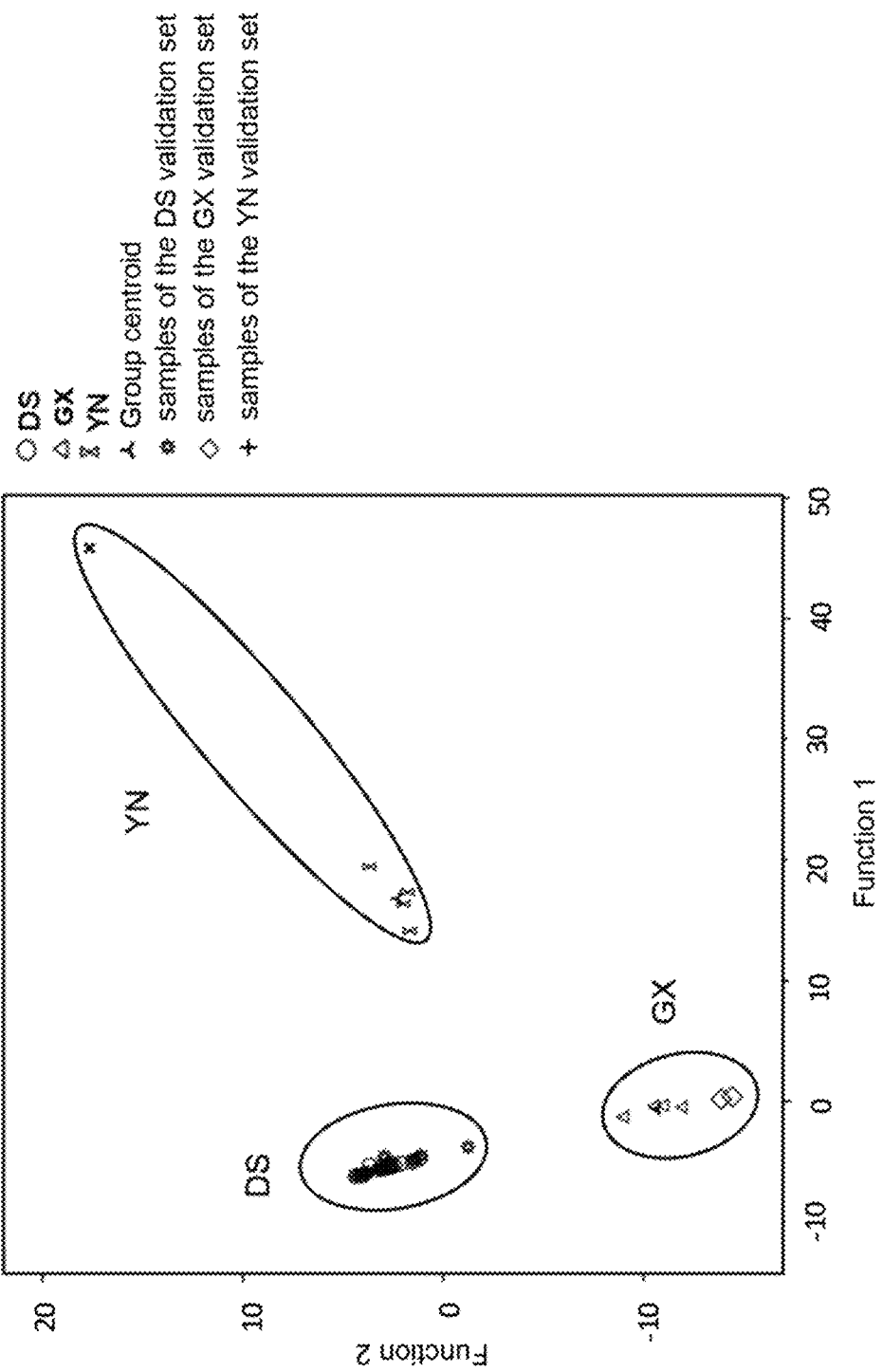
FIG. 4 is a diagram showing the distribution of samples in the training set and the testing set of Salviae miltiorrhizae radix et rhizoma and counterfeits thereof, with values of discriminant functions (values of $F_1$ and $F_2$, namely, Function 1 and Function 2) as horizontal and vertical coordinates.

Based on discriminant function values, distribution diagrams of samples in the training set and the testing set were obtained. F1 and F2 are the horizontal and vertical coordinates of the samples in the distribution diagram, respectively. The results of the distribution diagrams are shown in FIG. 3 (training set) and FIG. 4 (training set and testing set). In FIG. 3 and FIG. 4, Salviae miltiorrhizae radix et rhizoma (DS), Salvia przewalskii Maxim. (GX) and Salvia yunnanensis C. H. Wright (YN) in the samples in the training set and the testing set can be effectively discriminated.

Therefore, according to the method described above, the characteristic extraction was carried out with stepwise discriminant analysis under the guide of the pharmacodynamics information, so that three characteristic values were obtained and two discriminant functions were established, through which Salviae miltiorrhizae radix et rhizoma, Salvia przewalskii Maxim. and Salvia yunnanensis C. H. Wright can be effectively discriminated.

Example 2

In this example, the instruments used herein are as follows.

High performance liquid chromatography: chromatographic column: Shiseido Capcell Pak C18 (250 mm×4.6 mm, 5 μm, manufactured by Shiseido Co.,)

Mobile phase: methanol (A)—water containing 0.5% (v/v) acetic acid (B)

Gradient elution: using a binary gradient elution system, solvent A, methanol-solvent B water (0.5% (v/v) acetic acid), detection wavelength: 320 nm, flow rate: 0.8 mL·min$^{-1}$, column temperature: 30° C., injection volume: 20 μL The gradient elution procedure is shown in Table 10.

TABLE 10

| Time (min) | Mobile phase A (%) | Mobile phase B (%) |
|---|---|---|
| 0 | 10 | 90 |
| 10 | 20 | 80 |
| 20 | 22 | 78 |
| 30 | 40 | 60 |
| 55 | 43 | 57 |
| 70 | 44 | 56 |
| 85 | 49 | 51 |
| 105 | 90 | 10 |
| 120 | 90 | 10 |

In this example, the samples used herein are as follows.

In this experiment, a total of 31 batches of samples of Exocarpium citri grandis were collected, among which samples No. 7~16 and 15 were samples of Citrus grandis 'Tomentosa', and samples No. 16~18 and 20~31 were samples of Citrus grandis (L.) Osbeck. The detailed information of the samples is shown in Table 11 (samples No. 6 and 19 were abnormal samples and thus removed).

TABLE 11

Information of Exocarpium citri grandis samples

| Sample No. | Origins | Purchased from: | Name |
|---|---|---|---|
| 1 | Huazhou | Qingping Medicinal Material Marke, Guangzhout | Citrus grandis |
| 2 | Huazhou | Qingping Medicinal Material Marke, Guangzhout | 'Tomentosa' |
| 3 | Zhejiang | Jinhua Jianfeng Pharmacy | |
| 4 | Pingding, Huazhou | Zhongmao Specialty Co., Ltd., Huazhou | |
| 5 | Pingding, Huazhou | Zhongmao Specialty Co., Ltd., Huazhou | |
| 7 | Pingding, Huazhou | Lai's Citrus Grandis Cooperative, Huazhou | |
| 8 | Pingding, Huazhou | Lai's Citrus Grandis Cooperative, Huazhou | |
| 9 | Pingding, Huazhou | Lai's Citrus Grandis Cooperative, Huazhou | |
| 10 | Pingding, Huazhou | Lai's Citrus Grandis Cooperative, Huazhou | |
| 11 | Pingding, Huazhou | Pingding Pharmacy, Huazhou | |
| 12 | Pingding, Huazhou | Zhongguang Citrus Grandis Cooperative, Huazhou, Guangdong | |
| 13 | Pingding, Huazhou | Zhongguang Citrus Grandis Cooperative, Huazhou, Guangdong | |
| 14 | Pingding, Huazhou | Zhongguang Citrus Grandis Cooperative, Huazhou, Guangdong | |
| 15 | Pingding, Huazhou | Zhongguang Citrus Grandis Cooperative, Huazhou, Guangdong | |
| 16 | Pingding, Huazhou | farmers | |
| 17 | Sichuan | Tianyitang Pharmacy, Shenyang | Citrus grandis (L.) Osbeck |
| 18 | Sichuan | Yizhi Pharmacy, Shenyang | |
| 20 | Guangxi | Chengdafangyuan Pharmacy, Liaoning | |
| 21 | Hebei | Shenrong Wholesale Market, Shenyang | |
| 22 | Guangdong | Sifangyao Pharmacy, Shenyang | |
| 23 | Guangdong | Qingping Material Market, Guangzhou | |
| 24 | Hunan | Longgang, Shenzhen | |
| 25 | Guangdong | Ronghua TCM Hospital, Tanggu, Binhai New District, Tianjin | |
| 26 | Zhejiang | Jianmin Pharmacy, Tianjin | |
| 27 | Guangxi | Tongrentang Chain Pharmacy, Beijing | |
| 28 | Guangdong | Anguo Medicinal Material Market, Henan | |
| 29 | Guangdong | Huahui Pharmaceutical Ltd. | |
| 30 | Guilin, Guangxi | Medicine Company, Yangshuo, Guilin, Guangxi | |

TABLE 11-continued

Information of Exocarpium *citri grandis* samples

| Sample No. | Origins | Purchased from: | Name |
|---|---|---|---|
| 31 | Guangdong | Tongrentang Pharmacy, Beijing | |
| 32 | Guangdong | Tianpuren Pharmacy, Beijing | |
| 33 | Guangdong | Yongantang, Beijing | |

The specific method for pattern recognition on Exocarpium *citri grandis* includes steps described below.

1. Collection of Chemical Information

Figure 5:
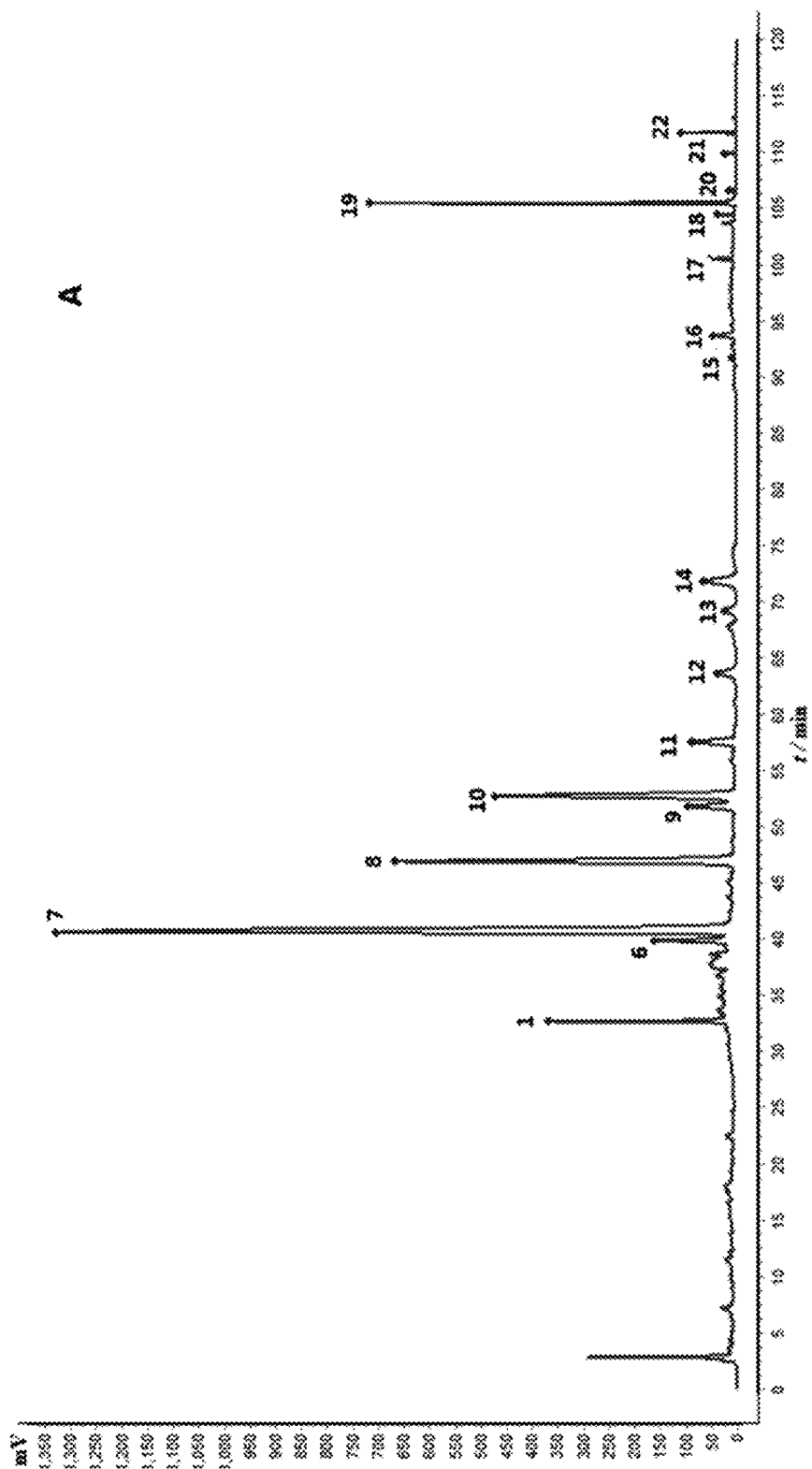
FIG. 5 is a HPLC diagram of Citrus grandis 'Tomentosa' samples.
Figure 6:
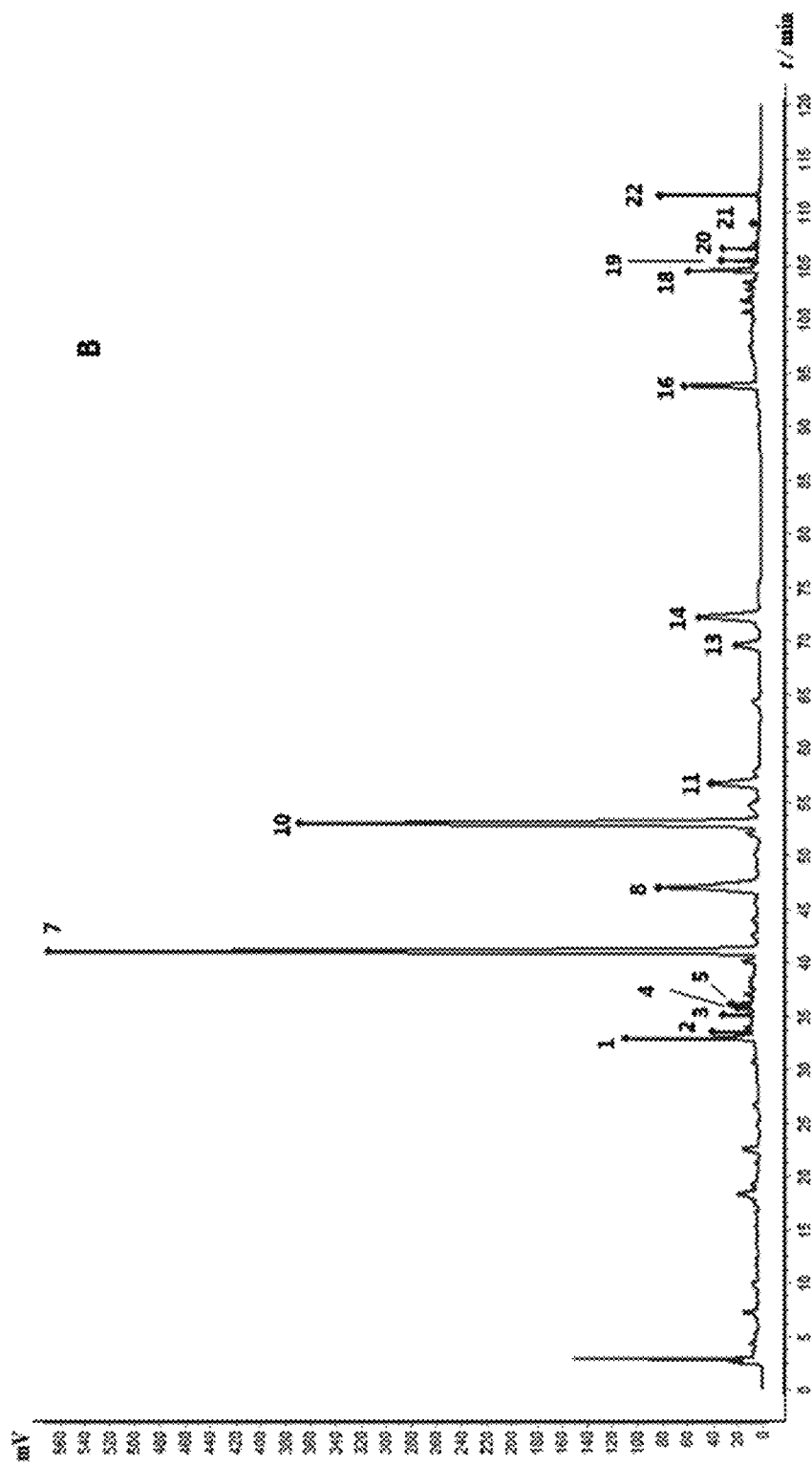
FIG. 6 is a HPLC diagram of Citrus grandis (L.) Osbeck samples.

Each of the 31 batches of medicinal materials was analyzed with HPLC, and all chromatographic peak data were obtained. The results for samples of *Citrus grandis* 'Tomentosa' and *Citrus grandis* (L.) Osbeck are shown respectively in FIG. 5 and FIG. 6.

2. Conversion of Fingerprint Data

Data of peaks common to samples of Exocarpium *citri grandis* were obtained. Because of the great difference among individuals of the data and the problem that some data are even not in the same order of magnitude, the statistical analysis is seriously affected. Therefore, it is necessary to convert the data into dimensionless data and establish a unified standard for the analysis. Through the normalization, the obtained test results are shown in Table 12.

TABLE 12

| Sample No. | Peak No. | | | | | |
|---|---|---|---|---|---|---|
| | 1 | 7 | 8 | 10 | 11 | 13 |
| 1 | 0.77542 | 1.03231 | 1.098 | −0.31984 | 0.32501 | −0.3161 |
| 2 | −0.47706 | 2.28813 | 0.18966 | −0.54969 | 1.42308 | −0.73492 |
| 3 | −0.38828 | 0.00309 | −0.48302 | 0.16561 | −1.35305 | −1.56266 |
| 4 | 0.64256 | 1.69249 | 0.22036 | 0.46572 | 0.83836 | 0.51833 |
| 5 | 0.75215 | 0.78701 | 0.69314 | 1.56093 | −0.4455 | 1.28936 |
| 7 | 0.39557 | −0.33952 | 0.11329 | −0.44861 | −1.16217 | −0.65271 |
| 8 | 0.20441 | 0.7027 | −0.07397 | 0.35434 | −0.00872 | −0.14915 |
| 9 | 0.25851 | 1.64956 | 0.59955 | −0.44601 | 0.34637 | −0.74918 |
| 10 | 2.21886 | 0.97939 | 2.50892 | −0.36144 | 0.21921 | −0.82297 |
| 11 | 1.53 | 0.87842 | 2.00127 | 2.97665 | 3.44834 | 2.94106 |
| 12 | 0.57022 | 0.62751 | 0.31081 | 1.18083 | 1.18604 | 0.47546 |
| 13 | 0.47128 | 0.69721 | 0.82808 | 0.89383 | 1.28086 | 0.06468 |
| 14 | 2.33788 | 1.23091 | 2.18913 | 0.9118 | 0.86903 | 0.29643 |
| 15 | 2.35442 | 1.26587 | 1.83603 | 0.05332 | 0.62255 | −0.53515 |
| 16 | 0.90824 | 0.42081 | 0.90002 | 0.64714 | 1.32642 | 0.51526 |
| 17 | −1.07264 | −1.02742 | −0.79849 | 0.25235 | −0.56444 | −0.02941 |
| 18 | −1.08759 | −0.97969 | −0.74436 | 0.26731 | −0.58212 | 0.07827 |
| 20 | −0.80042 | −0.86049 | −0.80729 | −1.06481 | −0.4687 | −0.82993 |
| 21 | −0.61334 | −0.70645 | −0.69898 | −2.23676 | −0.19692 | 1.36166 |
| 22 | −0.71142 | −0.68743 | −0.75799 | −0.32085 | −0.27239 | 0.28346 |
| 23 | −0.43057 | 0.42154 | −0.55504 | 1.91863 | −0.04743 | 1.96015 |
| 24 | −0.94254 | −1.13338 | −0.85498 | −1.49779 | −1.08809 | −1.74989 |
| 25 | −0.64021 | −0.88941 | −0.74381 | −0.40188 | −0.93923 | −0.34401 |
| 26 | −0.30112 | −0.4574 | −0.63694 | −0.2892 | −0.92035 | 0.0346 |
| 27 | −0.97043 | −1.08703 | −0.87473 | −1.4437 | −0.84566 | −0.78272 |
| 28 | −0.54593 | −0.83529 | −0.69223 | −0.04871 | −0.35481 | 0.1177 |
| 29 | −0.55601 | −0.61966 | −0.70215 | −0.07849 | −0.30322 | −0.0297 |
| 30 | −0.68132 | −0.84426 | −0.63508 | −0.04363 | −0.43421 | 1.38364 |
| 31 | −0.71985 | −0.94277 | −0.67874 | 0.12877 | −0.55916 | 0.80286 |
| 32 | −0.83835 | −0.93854 | −0.843 | −0.37329 | −0.56346 | 0.08094 |
| 33 | −0.83335 | −0.96875 | −0.79264 | −0.52692 | −0.85133 | −0.71368 |

| Sample No. | Peak No. | | | | | | |
|---|---|---|---|---|---|---|---|
| | 14 | 16 | 18 | 19 | 20 | 21 | 22 |
| 1 | 0.44569 | −0.54962 | 0.47992 | 0.96427 | −0.44687 | −0.07227 | −0.4304 |
| 2 | −0.23576 | −0.37727 | −0.69837 | 0.14831 | −1.28961 | −0.40428 | −0.65443 |
| 3 | −1.53446 | −0.27731 | −0.6237 | −0.64041 | −0.69542 | 2.09673 | −1.18693 |
| 4 | 1.18434 | −0.48197 | −0.53028 | 0.32363 | −1.16251 | −0.22635 | −0.84283 |
| 5 | 1.9903 | 0.80241 | −0.8497 | −0.02283 | −1.08218 | −0.2339 | 2.05939 |
| 7 | −0.24917 | −0.56734 | −0.91585 | −0.22224 | −1.35872 | 4.91268 | 0.19491 |
| 8 | 1.02487 | −0.40196 | −0.2296 | 0.14847 | −0.85398 | 0.19806 | −0.0233 |
| 9 | 0.02239 | −0.21216 | −0.53282 | −0.03351 | −1.12625 | −0.49295 | 0.15457 |
| 10 | −0.48195 | −0.38823 | 0.66275 | 1.07538 | −0.68241 | −0.23859 | −0.3122 |
| 11 | 2.09761 | −0.39437 | −0.17719 | 2.71287 | 0.40968 | 0.36605 | −0.50159 |
| 12 | 1.74061 | −0.45501 | −0.57139 | 0.98848 | −0.95633 | −0.34603 | −0.65966 |
| 13 | 1.51145 | −0.46104 | 0.12657 | 1.42013 | −0.63636 | −0.16303 | −0.42772 |
| 14 | 0.84603 | −0.24984 | −0.25222 | 1.57698 | −0.82572 | 0.15709 | 0.32687 |
| 15 | 0.13189 | −0.35896 | −0.36523 | 1.3054 | −1.0099 | −0.09806 | 0.13821 |
| 16 | 0.67316 | −0.21732 | −0.58506 | −0.32029 | −0.79064 | 0.39346 | 0.55249 |
| 17 | −0.32719 | −0.14399 | −0.81924 | −0.74023 | −0.65587 | −0.52997 | −0.87786 |
| 18 | 0.05887 | −0.11264 | −0.88464 | −0.67141 | 0.45801 | −0.36133 | −0.43594 |
| 20 | −1.03748 | −0.13468 | −0.38507 | −0.70749 | 0.46677 | −0.36303 | −0.30862 |
| 21 | 0.8836 | 0.20292 | 1.27508 | −0.67849 | 1.56476 | −0.22551 | 0.23541 |
| 22 | −0.4887 | −0.01455 | −0.15319 | −0.69773 | 0.22366 | −0.34275 | −0.05531 |
| 23 | 0.39637 | 0.6731 | 1.10273 | −0.66404 | 1.36091 | −0.31178 | 1.04068 |

TABLE 12-continued

| | | | | | | | |
|---|---|---|---|---|---|---|---|
| 24 | −1.52016 | −0.33866 | −0.23038 | −0.73935 | 0.50459 | −0.41322 | −0.62838 |
| 25 | −0.74702 | −0.10606 | −0.40189 | −0.68694 | −0.1951 | −0.48298 | −0.35446 |
| 26 | −0.37949 | 0.16403 | 0.30378 | −0.62392 | 0.69417 | −0.34968 | 1.0515 |
| 27 | −1.43029 | −0.21058 | 0.60485 | −0.71904 | 1.38928 | −0.18873 | −0.06867 |
| 28 | −0.67147 | −0.01568 | −0.35489 | −0.71323 | 0.06839 | −0.42108 | −0.42259 |
| 29 | −0.49586 | −0.06629 | −0.38195 | −0.69788 | 0.44945 | −0.36072 | −0.32845 |
| 30 | −0.99932 | −0.20395 | 0.23732 | −0.71291 | 1.59671 | −0.30956 | −0.18432 |
| 31 | 0.32524 | −0.06055 | 1.18871 | −0.71062 | 1.55139 | −0.2307 | −0.07547 |
| 32 | 0.0184 | −0.17019 | 0.66061 | −0.70945 | 1.36565 | −0.32048 | −0.28049 |
| 33 | −1.04151 | −0.21092 | −0.70315 | −0.73419 | −0.37716 | −0.48625 | −0.68321 |

3. Obtaining the Pharmacodynamics Information

According to the clinical application, 31 batches of medicinal materials were tested for cough relieving, expectorant action and anti-inflammation, respectively. The pharmacodynamics indexes were incubation period (the shorter the better), cough frequency (the less the better), phenol red excretion (the more the better), and extent of ear swelling (the lower the better). The obtained pharmacodynamics experiment data of Exocarpium citri grandis are shown in Table 13.

TABLE 13

Experiment data of Exocarpium citri grandis pharmacodynamics

| Batch | Incubation period (s) | Cough frequency | Phenol red excretion (μg/mL) | Swelling extent (%) |
|---|---|---|---|---|
| 1 | 43.4 | 40.7 | 1.2479 | 36.66 |
| 2 | 40 | 42.5 | 1.3566 | 33.98 |
| 3 | 41.1 | 47.7 | 1.2742 | 43.91 |
| 4 | 45.8 | 32.6 | 1.8128 | 26.61 |
| 5 | 44.8 | 34.7 | 1.7278 | 29.97 |
| 6 | 46.8 | 43.3 | 1.4959 | 35.48 |
| 7 | 45.8 | 34 | 1.3589 | 36.65 |
| 8 | 45.9 | 36.4 | 1.6343 | 22.06 |
| 9 | 46.6 | 38.5 | 1.1516 | 25.48 |
| 10 | 48.9 | 32.9 | 1.4156 | 29.9 |
| 11 | 46.2 | 34.2 | 1.4697 | 32.08 |
| 12 | 45.4 | 33.9 | 1.6948 | 37.46 |
| 13 | 42.4 | 34.4 | 1.32.4 | 29.23 |
| 14 | 46.4 | 32.6 | 1.5745 | 34.2 |
| 15 | 47.1 | 34.4 | 1.3726 | 32.63 |
| 16 | 44.9 | 31.5 | 1.7051 | 33.45 |
| 17 | 39.3 | 47.6 | 0.9078 | 36.25 |
| 18 | 40.8 | 45.2 | 1.153 | 45.43 |
| 19 | 41.7 | 50.9 | 0.894 | 42.59 |
| 20 | 40.8 | 51.7 | 0.942 | 46.51 |
| 21 | 41.2 | 54.5 | 1.0155 | 49.55 |
| 22 | 38.1 | 48 | 1.1858 | 41.99 |
| 23 | 42.9 | 43 | 1.08 | 38.19 |
| 24 | 40.4 | 47.2 | 1.2969 | 45.03 |
| 25 | 38.8 | 54.8 | 1.0366 | 61.26 |
| 26 | 41.4 | 49.9 | 1.3882 | 42.35 |
| 27 | 40.2 | 44.3 | 1.2069 | 47.08 |
| 28 | 42.6 | 39.3 | 1.1857 | 52.83 |
| 29 | 43.5 | 48.9 | 1.065 | 35.02 |
| 30 | 42.9 | 49.9 | 1.1313 | 43.24 |
| 31 | 41.1 | 47.3 | 1.0073 | 49.25 |
| 32 | 39.8 | 50.7 | 1.072 | 38.71 |
| 33 | 40.1 | 36 | 0.9092 | 39.24 |

Normalization of the Pharmacodynamics Data

Since units of measure and orders of magnitude are different for the values of various pharmacodynamics indexes, the statistical analysis cannot be carried out at the same time. All of the data were converted into dimensionless data and analyzed correspondingly following the normalization of the data. The normalized data are shown in Table 14.

TABLE 14

| Incubation period | Cough frequency | Phenol red excretion | Swelling extent | Group |
|---|---|---|---|---|
| 0.19014 | −0.16348 | −0.1292 | −0.22264 | 1 |
| −1.00279 | 0.07913 | 0.29818 | −0.53226 | 1 |
| −0.61684 | 0.77999 | −0.0258 | 0.61496 | 1 |
| 1.03221 | −1.2552 | 2.09187 | −1.38372 | 1 |
| 0.68135 | −0.97216 | 1.75767 | −0.99554 | 1 |
| 1.03221 | −1.06651 | 0.30723 | −0.22379 | 1 |
| 1.0673 | −0.74303 | 1.39004 | −1.90938 | 1 |
| 1.3129 | −0.45999 | −0.50784 | −1.51427 | 1 |
| 2.11989 | −1.21476 | 0.53016 | −1.00363 | 1 |
| 1.17256 | −1.03955 | 0.74287 | −0.75177 | 1 |
| 0.89187 | −1.07998 | 1.62792 | −0.13021 | 1 |
| −0.16072 | −1.01259 | 0.17001 | −1.08103 | 1 |
| 1.24273 | −1.2552 | 1.15492 | −0.50684 | 1 |
| 1.48834 | −1.01259 | 0.36109 | −0.68823 | 1 |
| 0.71644 | −1.40346 | 1.66842 | −0.59349 | 1 |
| −1.24839 | 0.76651 | −1.46641 | −0.27001 | 2 |
| −0.7221 | 0.44304 | −0.50233 | 0.79056 | 2 |
| −0.7221 | 1.31911 | −1.33194 | 0.91534 | 2 |
| −0.58175 | 1.6965 | −1.04295 | 1.26655 | 2 |
| −1.66943 | 0.82042 | −0.37337 | 0.39314 | 2 |
| 0.01471 | 0.14652 | −0.78935 | −0.04588 | 2 |
| −0.86244 | 0.7126 | 0.06345 | 0.74435 | 2 |
| −1.42382 | 1.73693 | −0.95999 | 2.61941 | 2 |
| −0.51158 | 1.07651 | 0.42243 | 0.43473 | 2 |
| −0.93262 | 0.32173 | −0.29041 | 0.98119 | 2 |
| −0.09055 | −0.35217 | −0.37376 | 1.64549 | 2 |
| 0.22523 | 0.94172 | −0.84833 | −0.41211 | 2 |
| 0.01471 | 1.07651 | −0.58765 | 0.53755 | 2 |
| −0.61684 | 0.72608 | −1.0752 | 1.23189 | 2 |
| −1.07296 | 1.18433 | −0.82081 | 0.0142 | 2 |
| −0.9677 | −0.79694 | −1.46091 | 0.07543 | 2 |

4. Analysis of Correlation Between Valid Peak Values and the Medicinal Effect

In order to determine the relationship between valid peak values and medicinal effects, it is necessary to determine firstly the correlation between each peak value and medicinal effects to obtain the characteristic chemical indexes which can reflect the medicinal effect. The results of the analysis are shown in Table 15.

TABLE 15

| | Pearson Correlation analysis | | | |
|---|---|---|---|---|
| | Incubation period | Cough frequency | Phenol red excretion | Swelling extent |
| Peak value 1 | .853** | −.753** | .653** | −.581** |
| Peak value 7 | .662** | −.663** | .646** | −.733** |
| Peak value 8 | .799** | −.742** | .585** | −.600** |
| Peak value 10 | .422* | −.522** | .456* | −.428* |
| Peak value 11 | .491** | −.565** | .490** | −.517** |
| Peak value 13 | .184 | −.095 | .152 | −.086 |
| Peak value 14 | .504** | −.538** | .590** | −.530** |
| Peak value 16 | −.236 | .316 | −.189 | .235 |
| Peak value 18 | −.092 | .328 | −.286 | .229 |
| Peak value 19 | .667** | −.676** | .548** | −.554** |
| Peak value 20 | −.475** | .674** | −.559** | .575** |

TABLE 15-continued

| | Pearson Correlation analysis | | | |
|---|---|---|---|---|
| | Incubation period | Cough frequency | Phenol red excretion | Swelling extent |
| Peak value 21 | .243 | −.235 | .182 | −.083 |
| Peak value 22 | .237 | −.119 | .249 | −.140 |

**Significance level is 0.01.;
*Significance level is 0.05.

It can be seen from the above table that the linear relationship between each medicinal effect and each peak value was linear with some peak values, but the correlation coefficients were small, most of which were only about 0.7, and eight peaks, $X_1$, $X_7$, $X_8$, $X_{10}$, $X_{11}$, $X_{14}$, $X_{19}$ and $X_{20}$, were significantly correlated with the medicinal effect.

5. Training Set and Testing Set Classification

The 31 batches of samples of Exocarpium *citri grandis* were classified into a training set and a testing set by using a random algorithm.

Samples of the training set were No. 2, 3.4, 7, 8, 10, 11, 13, 14, 15, 18, 20, 21, 23, 24, 26, 28, 29, 30, 31, 32, and 33.

Samples of the testing set were No. 1, 5, 9, 12, 16, 17, 22, 25, and 27.

6. Characteristic Extraction Under the Guide of the Pharmacodynamics Information Peaks contributed to the classification were screened by stepwise discriminant analysis based on a data matrix (8×31 data matrix) composed of index peaks significantly correlated with the medicinal effect. By the method of the stepwise discriminant analysis, using Wilks' Lambda as the evaluation index, peaks with the same probability within 0.05 were selected as main peaks and then retained, and peaks with the same probability greater than 0.1 were selected as undifferentiated peaks and then removed, so as to discriminate the classification of Exocarpium *citri grandis*.

The results of the characteristic extraction obtained by stepwise discriminant analysis on variables are shown in Table 16.

TABLE 16

| | Variables analyzed | | |
|---|---|---|---|
| | Tolerance | F significance to be input | Wilks' lambda |
| Selected variable | | | |
| $X_7$ | 0.950 | 0.004 | 0.183 |
| $X_{20}$ | 0.936 | 0.001 | 0.211 |
| $X_8$ | 0.892 | 0.006 | 0.179 |
| Removed variable | | | |
| $X_1$ | 0.174 | 0.711 | 0.134 |
| $X_{10}$ | 0.932 | 0.618 | 0.134 |
| $X_{11}$ | 0.623 | 0.970 | 0.135 |
| $X_{14}$ | 0.874 | 0.867 | 0.127 |
| $X_{19}$ | 0.424 | 0.342 | 0.130 |

It can be seen from the table above that the characteristic variables contributed to the classification of Exocarpium *citri grandis* were $X_7$, $X_8$ and $X_{20}$.

7. Establishment of the Pattern Recognition Model

The samples in the training set are used as a data set, and the characteristic variables $X_7$, $X_8$ and $X_{20}$ selected by stepwise discriminant analysis are used as input variables, as shown in Table 17. A discriminant function equation is established according to discriminant function coefficients.

TABLE 17

| Typical discriminant function coefficient | |
|---|---|
| Variable | Function 1 |
| $X_7$ | 0.828 |
| $X_8$ | 0.767 |
| $X_{20}$ | −1.303 |
| Constant | −0.099 |

The discriminant function equation was $F_1 = 0.828X_7 + 0.767X_8 - 1.303X_{20} - 0.099$.

When $F_1 > 0$, the sample is *Citrus grandis* 'Tomentosa',
When $F_1 < 0$, the sample is *Citrus grandis* (L.) Osbeck.

8. Model Validation (1) Internal validation of the model. The model was validated by Leave-one-out internal cross-validation. Results demonstrate that in the model established as above, the accuracy of the discrimination with the leave-one-out internal cross-validation is 100%.

(2) The testing set was used for the external validation of the model, and the characteristic peaks of the samples in the testing set were brought into the discriminant function, to obtain discriminant scores and discriminant classification results of the samples. The results are shown in Table 18. The discriminant results of the model were consistent with the results of the character identification, and the accuracy of the discrimination was 100%.

TABLE 18

| The discriminant results of the samples in the testing set | | | |
|---|---|---|---|
| Sample No. | F1 | Results | Whether the result is consistent with the actual classification result |
| 1 | 2.17959 | *Citrus grandis* 'Tomentosa' | Yes |
| 5 | 2.49396 | *Citrus grandis* 'Tomentosa' | Yes |
| 9 | 3.194 | *Citrus grandis* 'Tomentosa' | Yes |
| 12 | 1.90475 | *Citrus grandis* 'Tomentosa' | Yes |
| 16 | 1.96936 | *Citrus grandis* 'Tomentosa' | Yes |
| 17 | −0.70786 | *Citrus grandis* (L.) Osbeck | Yes |
| 22 | −1.54141 | *Citrus grandis* (L.) Osbeck | Yes |
| 25 | −1.1521 | *Citrus grandis* (L.) Osbeck | Yes |
| 27 | −3.48086 | *Citrus grandis* (L.) Osbeck | Yes |

9. Visualization of the Results

Figure 7:
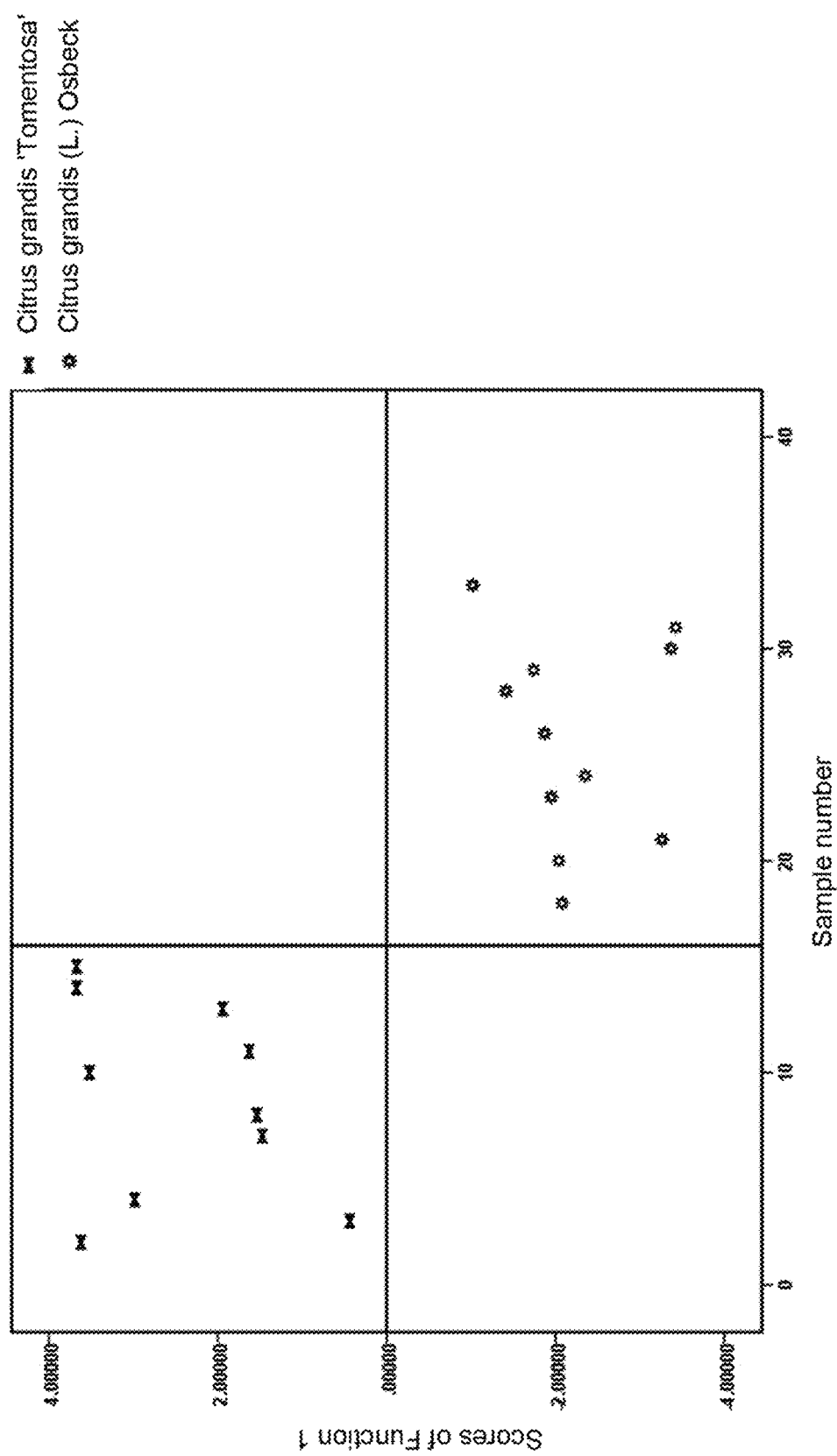
FIG. 7 is a diagram showing the distribution of samples in the training set of Exocarpium citri grandis, with sample numbers as horizontal coordinate and discriminant function values (values of $F_1$, namely, score of Function 1) as vertical coordinate.
Figure 8:
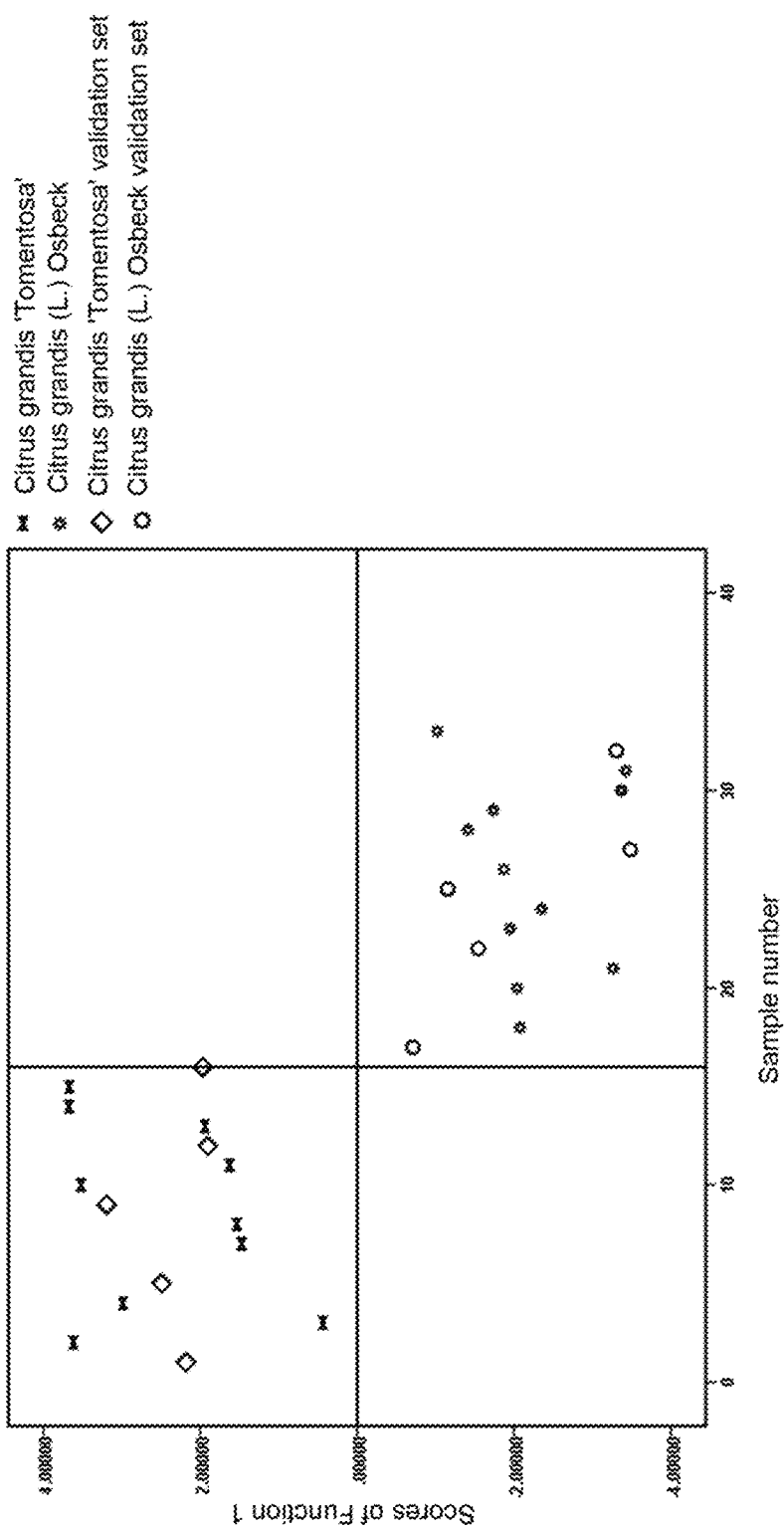
FIG. 8 is a diagram showing the distribution of samples in the training set and the testing set of Exocarpium citri grandis, with sample numbers as horizontal coordinate and discriminant function values (values of $F_1$, namely, score of Function 1) as vertical coordinate.

Based on discriminant function values and sample numbers, distribution diagrams of samples in the training set and the testing set were obtained. The discriminant function value $F_1$ and the sample number are the horizontal and vertical coordinates of the samples in the distribution diagram, respectively. The results of the distribution diagrams are shown in FIG. 7 (training set) and FIG. 8 (training set and testing set). In FIG. 7 and FIG. 8, *Citrus grandis* 'Tomentosa' and *Citrus grandis* (L.) Osbeck in the samples of the training set and the testing set can be effectively discriminated.

Therefore, according to the method described above, the characteristic extraction was carried out with stepwise discriminant analysis under the guide of the pharmacodynamics information, so that three characteristic values were obtained and one discriminant function, through which *Citrus grandis* 'Tomentosa' and *Citrus grandis* (L.) Osbeck can be effectively discriminated.

Example 3

In this example, the instruments and software used herein are shown in Table 19.

TABLE 19

| Instruments and software used herein | |
|---|---|
| VERTEX 70 Fourier transform near-infrared spectrometer | Broker Cooperation (Germany) |
| OPUS 6.5 Workstation | Broker Cooperation (Germany) |
| RT-04A high speed grinder | Hong Kong Hongquan Pharmaceutical Machinery Co., Ltd. |
| SPSS 21.0 software | IBM Cooperation (U.S.A) |
| Matlab R2014a software | Mathworks Cooperation (U.S.A) |

Sample Collection and Pre-Treatment

Sample Collection

In this example, 43 batches of typical, representative samples of Spina gleditsiae and counterfeits thereof were collected, wherein 32 batches were of Spina gleditsiae. (*G. sinensis*) (No. 1~32), 4 batches are of counterfeits Spina of *Gleditsia japonica* Miq. (*Gleditsia japonica* Miq., *G. japonica*) (No. 33~36), 3 batches were of counterfeits Spina of *Gleditsia microphylla* Gordon ex Ys T. Lee (*Gleditsia microphylla* Gordon ex Y T. Lee, *G. microphylla*) (No. 37~39) and 4 batches were of counterfeits Spina of *Rubus cochinchinensis* Tratt. (*R. cochinchinensis*) (No. 40~42). According to the authentication by Zhang Di, chief pharmacist of Beijing University of Chinese Medicine, all of the samples are quality products of traditional Chinese medicine, Spina gleditsiae and various typical counterfeits of Spina gleditsiae. The detailed information of the samples is shown in Table 20.

TABLE 20

| No. | Variety | Origins | Characteristic |
|---|---|---|---|
| 1 | G. sinensis | Zhashui, Shaanxi | Medical material |
| 2 | G. sinensis | Yuncheng, Shanxi | Medical material |
| 3 | G. sinensis | Zaozhuang, Shandong | Medical material |
| 4 | G. sinensis | Taian, Shandong | Medical material |
| 5 | G. sinensis | Shandong | Decoction pieces |
| 6 | G. sinensis | Shandong | Decoction pieces |
| 7 | G. sinensis | Shandong | Medical material |
| 8 | G. sinensis | Shandong | Medical material |
| 9 | G. sinensis | Xiangyang, Hubei | Medical material |
| 10 | G. sinensis | Wuhan, Hubei | Medical material |
| 11 | G. sinensis | Wuhan, Hubei | Medical material |
| 12 | G. sinensis | Luoyang, Henan | Medical material |
| 13 | G. sinensis | Luoyang, Henan | Medical material |
| 14 | G. sinensis | Luoyang, Henan | Medical material |
| 15 | G. sinensis | Luoyang, Henan | Medical material |
| 16 | G. sinensis | Henan | Decoction pieces |
| 17 | G. sinensis | Henan | Medical material |
| 18 | G. sinensis | Henan | Decoction pieces |
| 19 | G. sinensis | Henan | Medical material |
| 20 | G. sinensis | Henan | Decoction pieces |
| 21 | G. sinensis | Henan | Medical material |
| 22 | G. sinensis | Xinle, Hebei | Medical material |
| 23 | G. sinensis | Bozhou, Anhui | Medical material |
| 24 | G. sinensis | Guangxi | Medical material |
| 25 | G. sinensis | Beijing | Medical material |
| 26 | G. sinensis | Beijing | Medical material |
| 27 | G. sinensis | Beijing | Medical material |

TABLE 20-continued

| No. | Variety | Origins | Characteristic |
|---|---|---|---|
| 28 | G. sinensis | Beijing | Medical material |
| 29 | G. sinensis | Beijing | Medical material |
| 30 | G. sinensis | Beijing | Medical material |
| 31 | G. sinensis | Beijing | Medical material |
| 32 | G. sinensis | Beijing | Medical material |
| 33 | G. japonica | Dalian, Liaoning | Medical material |
| 34 | G. japonica | Wuhan, Hubei | Medical material |
| 35 | G. japonica | Changchun, Jilin | Decoction pieces |
| 36 | G. japonica | Taian, Shandong | Medical material |
| 37 | G. microphylla | Guangdong | Decoction pieces |
| 38 | G. microphylla | Shanxi | Decoction pieces |
| 39 | G. microphylla | Guangxi | Decoction pieces |
| 40 | R. cochinchinensis | Guangxi | Decoction pieces |
| 41 | R. cochinchinensis | Guangxi | Decoction pieces |
| 42 | R. cochinchinensis | Guangdong | Decoction pieces |
| 43 | R. cochinchinensis | Yunnan | Decoction pieces |

Sample Pre-Treatment

All samples were washed and cleaned to remove dust and debris, and then dried, pulverized and filtered through a 50-mesh sieve, and sealed at 25° C. for later use.

1. Collection of Near-Infrared Spectra

Figure 9:
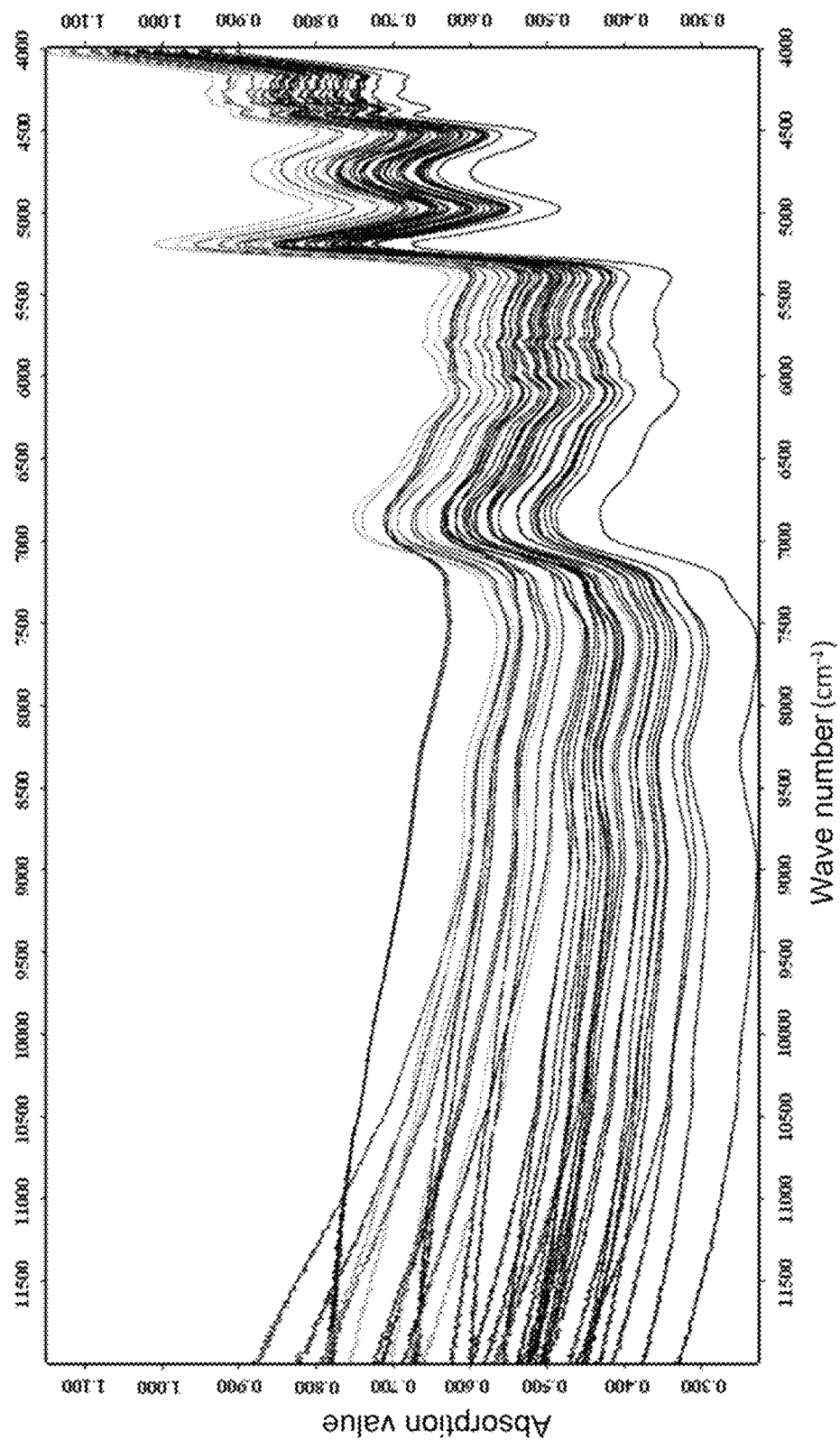
FIG. 9 is a diagram showing the original average near-infrared spectra of samples of Spina gleditsiae. and counterfeits thereof, collected by infrared spectrometry.

Near-infrared spectra of the samples were collected by using an optical fiber probe, wherein the collection interval was 12000-4000 $cm^{-1}$, the instrumental resolution was 4 $cm^{-1}$, and the number of scan was 32. The internal reference background was removed, and the spectra were collected at three different positions of each batch of samples, and the average spectra were obtained as the representative spectra. The average spectra were obtained by using OPUS 6.5 Workstation (Bruker, Germany). The experimental temperature was kept at 25° C. and the humidity was maintained at about 60%. The original average near-infrared spectra of Spina gleditsiae and counterfeits thereof are shown in FIG. 9.

Methods for Spectrum Data Pre-Treatment

Figure 10:
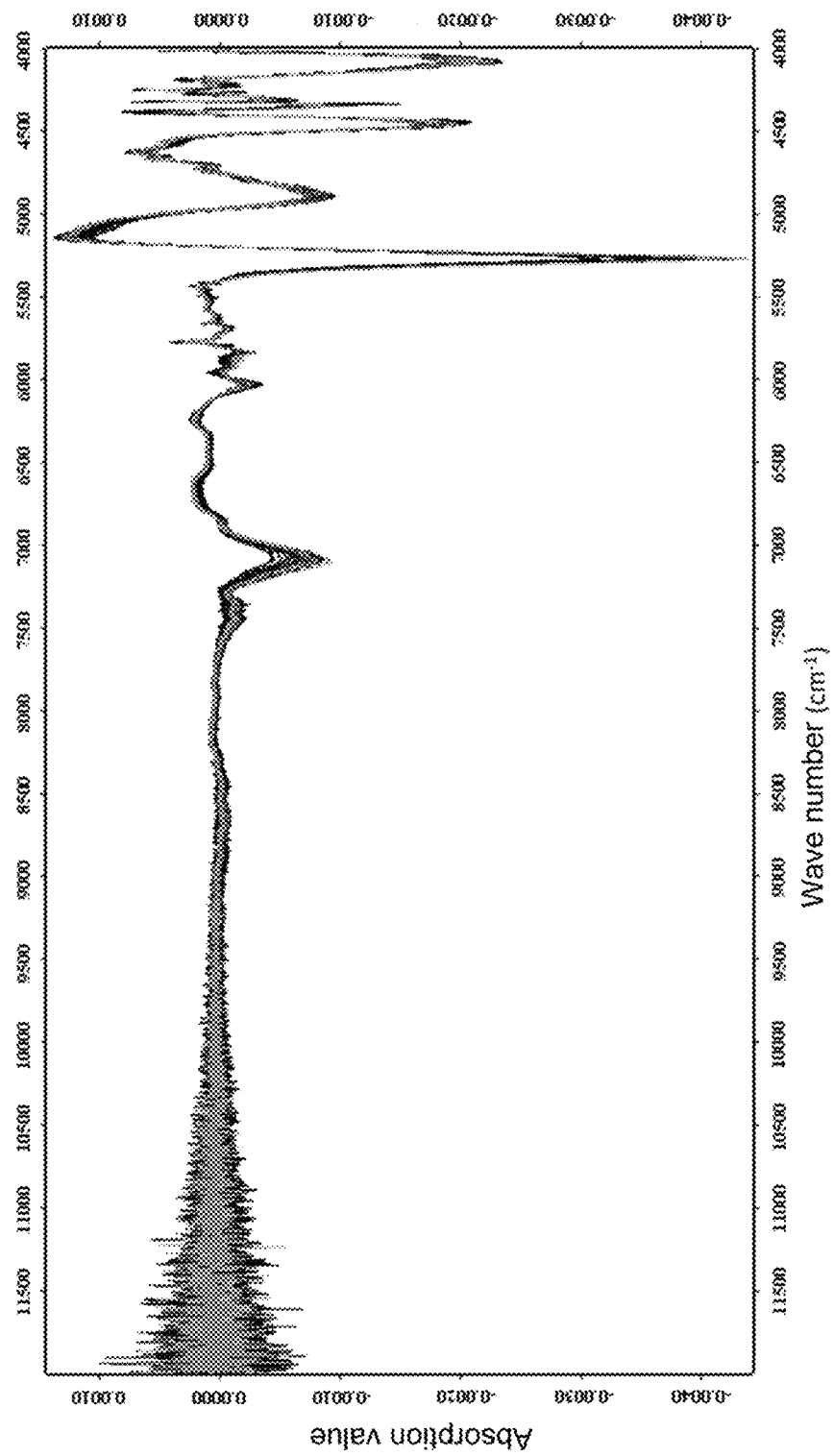
FIG. 10 is a near-infrared spectra diagram obtained from the pre-treatment on the original average near-infrared spectra by using a first derivative ($1^{st}$ D) method.

The spectra of the samples were pre-treated by Savitzky-Golay smoothing, vector normalization, min max normalization, a first derivative method, and a second derivative method. The effects on the modeling accuracy by different pre-treatment methods were investigated. The spectrum data pre-treatment was performed by using OPUS 6.5 Workstation (manufactured by Bruker Cooperation, Germany). FIG. 10 shows a near-infrared spectra diagram obtained after the original average near-infrared spectrum was pre-treated by using the first derivative ($1^{st}$ D) method.

Division of the Spectral Band

Noise interference peaks within intervals of 12000-11800 $cm^{-1}$ and 4200-4000 $cm^{-1}$, and water peaks within intervals of 7500-6500 $cm^{-1}$ and 5500-5000 $cm^{-1}$ were removed. After the noise interference peaks and water peaks were removed, the whole spectral band was divided into three intervals, that is, 11800-7500 $cm^{-1}$, 6500-5500 $cm^{-1}$ and 5000-4200 $cm^{-1}$.

Extraction of the Characteristic Wave Number

The SPA algorithm was used for extracting the characteristic wave numbers within the three spectral intervals under different pre-treatment conditions. The SPA algorithm was run on the software, Matlab R2014a, and the complexity of modeling was greatly reduced after characteristic variables were extracted.

It is found from preliminary study that the accuracy of the classification recognition was optimal when the spectra within the interval of 5000~4200 $cm^{-1}$ and treated by first-order derivative method were used for modeling. Therefore, in this example, the spectra within the interval of 5000~4200 $cm^{-1}$ and treated by first-order derivative method were used for extracting the characteristic data by SPA (see Tables 21-1, 21-2 and 21-3).

TABLE 21-1

| | $X_1$ | $X_2$ | $X_3$ | $X_4$ | $X_5$ | $X_6$ | $X_7$ | $X_8$ | $X_9$ | $X_{10}$ |
|---|---|---|---|---|---|---|---|---|---|---|
| 1 | 0.000516 | −0.000202 | −0.000661 | −0.000778 | −0.000728 | −0.000609 | 0.00008 | 0.000181 | 0.000394 | 0.000535 |
| 2 | 0.000547 | −0.00028 | −0.000776 | −0.000838 | −0.00078 | −0.000637 | 0.000092 | 0.000189 | 0.000432 | 0.000646 |
| 3 | 0.000496 | −0.000312 | −0.000781 | −0.000829 | −0.000794 | −0.000657 | 0.000113 | 0.000182 | 0.000445 | 0.000595 |
| 4 | 0.00059 | −0.000086 | −0.000578 | −0.000722 | −0.000698 | −0.000593 | 0.000033 | 0.000147 | 0.00037 | 0.000536 |
| 5 | 0.000538 | −0.000216 | −0.000678 | −0.000809 | −0.000745 | −0.00062 | 0.000085 | 0.000191 | 0.00044 | 0.00057 |
| 6 | 0.000531 | −0.000289 | −0.000747 | −0.000818 | −0.000754 | −0.000637 | 0.00012 | 0.000171 | 0.000457 | 0.000613 |
| 7 | 0.000539 | −0.00021 | −0.000678 | −0.000808 | −0.000772 | −0.000636 | 0.000043 | 0.000178 | 0.000406 | 0.000576 |
| 8 | 0.000629 | −0.000154 | −0.000652 | −0.00077 | −0.000742 | −0.00064 | 0.000072 | 0.000163 | 0.000405 | 0.000613 |
| 9 | 0.000554 | −0.000219 | −0.0007 | −0.000799 | −0.000744 | −0.000644 | 0.000067 | 0.000152 | 0.00041 | 0.000551 |
| 10 | 0.000613 | −0.000127 | −0.000563 | −0.000647 | −0.000594 | −0.000495 | 0.000146 | 0.000149 | 0.000407 | 0.000503 |
| 11 | 0.000594 | −0.000151 | −0.000633 | −0.00074 | −0.000706 | −0.000569 | 0.000076 | 0.000144 | 0.000398 | 0.000529 |
| 12 | 0.00056 | −0.000197 | −0.000663 | −0.00078 | −0.000767 | −0.000633 | 0.00007 | 0.000146 | 0.000412 | 0.000585 |
| 13 | 0.000536 | −0.000231 | −0.000767 | −0.000833 | −0.000808 | −0.000682 | 0.000051 | 0.000166 | 0.000416 | 0.0006 |
| 14 | 0.000551 | −0.000197 | −0.000667 | −0.000757 | −0.000729 | −0.000617 | 0.000081 | 0.000188 | 0.000409 | 0.000561 |
| 15 | 0.000555 | −0.000256 | −0.000739 | −0.000848 | −0.000787 | −0.000661 | 0.000043 | 0.000148 | 0.000409 | 0.000642 |
| 16 | 0.000483 | −0.000252 | −0.000725 | −0.000818 | −0.000761 | −0.000636 | 0.00009 | 0.000193 | 0.000403 | 0.000542 |
| 17 | 0.0006 | −0.00015 | −0.00068 | −0.000752 | −0.000717 | −0.000604 | 0.000079 | 0.000134 | 0.000382 | 0.000604 |
| 18 | 0.000604 | −0.000085 | −0.000559 | −0.000692 | −0.000663 | −0.000549 | 0.000059 | 0.000153 | 0.000387 | 0.000557 |
| 19 | 0.000636 | −0.000173 | −0.000688 | −0.000794 | −0.000778 | −0.000612 | 0.000106 | 0.000178 | 0.000436 | 0.00061 |
| 20 | 0.000565 | −0.000143 | −0.000622 | −0.000754 | −0.000727 | −0.000598 | 0.000059 | 0.000149 | 0.0004 | 0.000544 |
| 21 | 0.000626 | −0.000089 | −0.000553 | −0.000691 | −0.000661 | −0.000548 | 0.000082 | 0.000144 | 0.000379 | 0.000529 |
| 22 | 0.000635 | −0.000073 | −0.000533 | −0.000617 | −0.000581 | −0.000476 | 0.000104 | 0.000149 | 0.000368 | 0.000476 |
| 23 | 0.000602 | −0.000165 | −0.00067 | −0.000737 | −0.000716 | −0.00059 | 0.000075 | 0.000133 | 0.000418 | 0.000541 |
| 24 | 0.000584 | −0.000208 | −0.000696 | −0.000801 | −0.000762 | −0.000638 | 0.000103 | 0.000149 | 0.000427 | 0.000554 |
| 25 | 0.000537 | −0.000154 | −0.000622 | −0.00075 | −0.000712 | −0.000619 | 0.000064 | 0.00016 | 0.000397 | 0.000569 |
| 26 | 0.000531 | −0.000137 | −0.000606 | −0.000683 | −0.000682 | −0.000552 | 0.000044 | 0.000133 | 0.000357 | 0.000544 |
| 27 | 0.000477 | −0.000121 | −0.000531 | −0.00064 | −0.000613 | −0.00052 | 0.000089 | 0.000175 | 0.00037 | 0.000521 |
| 28 | 0.000508 | −0.000144 | −0.000578 | −0.000666 | −0.000643 | −0.000552 | 0.000054 | 0.00014 | 0.00036 | 0.000517 |
| 29 | 0.000479 | −0.000136 | −0.000541 | −0.000643 | −0.000613 | −0.000512 | 0.00009 | 0.000165 | 0.000354 | 0.000515 |
| 30 | 0.000468 | −0.000146 | −0.000548 | −0.000638 | −0.000637 | −0.000524 | 0.000096 | 0.000161 | 0.000365 | 0.000497 |
| 31 | 0.000521 | −0.000207 | −0.000665 | −0.000761 | −0.000728 | −0.00062 | 0.000074 | 0.00016 | 0.000387 | 0.00057 |
| 32 | 0.000499 | −0.000187 | −0.000641 | −0.000751 | −0.000722 | −0.000583 | 0.000096 | 0.000161 | 0.000396 | 0.00057 |
| 33 | 0.000643 | −0.000072 | −0.000513 | −0.000618 | −0.000595 | −0.000507 | 0.000001 | 0.000069 | 0.000279 | 0.000579 |
| 34 | 0.000651 | −0.0001 | −0.000552 | −0.00063 | −0.000582 | −0.000494 | −0.000029 | 0.000035 | 0.000286 | 0.000561 |
| 35 | 0.000582 | −0.000203 | −0.000711 | −0.000791 | −0.000757 | −0.000626 | 0.000031 | 0.000137 | 0.000389 | 0.000661 |
| 36 | 0.000627 | −0.000066 | −0.000536 | −0.000638 | −0.00062 | −0.000519 | −0.000017 | 0.00009 | 0.000285 | 0.000592 |
| 37 | 0.000598 | −0.000157 | −0.000641 | −0.000768 | −0.000691 | −0.000574 | 0.000091 | 0.000195 | 0.000413 | 0.000583 |
| 38 | 0.000555 | −0.000227 | −0.000762 | −0.000848 | −0.000785 | −0.000633 | 0.000104 | 0.000226 | 0.000432 | 0.00062 |
| 39 | 0.0006 | −0.000151 | −0.000636 | −0.000743 | −0.000707 | −0.000564 | 0.000048 | 0.00019 | 0.000405 | 0.000581 |
| 40 | 0.000636 | 0.000002 | −0.000474 | −0.00066 | −0.000618 | −0.000508 | −0.000028 | 0.000186 | 0.000335 | 0.000525 |
| 41 | 0.000595 | −0.000082 | −0.000537 | −0.000648 | −0.000645 | −0.000493 | 0.000081 | 0.00025 | 0.000449 | 0.000501 |
| 42 | 0.000663 | 0.000001 | −0.000464 | −0.000614 | −0.000579 | −0.000472 | −0.000008 | 0.000191 | 0.000392 | 0.000525 |
| 43 | 0.000671 | 0.000047 | −0.00043 | −0.000591 | −0.000554 | −0.000429 | 0.000013 | 0.000192 | 0.000374 | 0.000514 |

TABLE 21-2

| | $X_{11}$ | $X_{12}$ | $X_{13}$ | $X_{14}$ | $X_{15}$ | $X_{16}$ | $X_{17}$ | $X_{18}$ | $X_{19}$ | $X_{20}$ |
|---|---|---|---|---|---|---|---|---|---|---|
| 1 | 0.000644 | 0.000462 | 0.000397 | 0.000384 | −0.000062 | −0.000244 | −0.001777 | −0.001504 | −0.00079 | 0.000277 |
| 2 | 0.00077 | 0.000522 | 0.000469 | 0.000415 | −0.000075 | −0.000307 | −0.001869 | −0.001556 | −0.000795 | 0.000366 |
| 3 | 0.000741 | 0.00049 | 0.000435 | 0.000374 | −0.000118 | −0.000334 | −0.001893 | −0.001568 | −0.000747 | 0.000381 |
| 4 | 0.000647 | 0.000458 | 0.000393 | 0.000371 | −0.000036 | −0.000247 | −0.00172 | −0.001555 | −0.000777 | 0.000279 |
| 5 | 0.000699 | 0.000477 | 0.000419 | 0.000372 | −0.000109 | −0.000313 | −0.001837 | −0.001536 | −0.000767 | 0.000353 |
| 6 | 0.000743 | 0.000497 | 0.000441 | 0.000399 | −0.000095 | −0.000328 | −0.001962 | −0.001588 | −0.000779 | 0.000369 |
| 7 | 0.000662 | 0.000458 | 0.000424 | 0.0004 | −0.000061 | −0.000261 | −0.001787 | −0.001535 | −0.000794 | 0.000296 |
| 8 | 0.00074 | 0.000487 | 0.000488 | 0.000438 | −0.000041 | −0.000284 | −0.001923 | −0.001601 | −0.000879 | 0.00021 |
| 9 | 0.00075 | 0.0005 | 0.000429 | 0.000423 | −0.000045 | −0.000276 | −0.001889 | −0.001631 | −0.000804 | 0.000398 |
| 10 | 0.000655 | 0.000452 | 0.000388 | 0.000351 | −0.000045 | −0.000243 | −0.001727 | −0.001501 | −0.000702 | 0.000377 |
| 11 | 0.000725 | 0.000436 | 0.000379 | 0.000365 | −0.000094 | −0.000334 | −0.001875 | −0.001572 | −0.000722 | 0.000438 |
| 12 | 0.000752 | 0.000455 | 0.000412 | 0.000369 | −0.000118 | −0.00037 | −0.00181 | −0.001559 | −0.000733 | 0.000478 |
| 13 | 0.00079 | 0.000491 | 0.00042 | 0.000405 | −0.000045 | −0.000313 | −0.001889 | −0.001621 | −0.000737 | 0.00049 |
| 14 | 0.000724 | 0.000449 | 0.000421 | 0.000387 | −0.000102 | −0.000309 | −0.001749 | −0.001535 | −0.000751 | 0.000297 |
| 15 | 0.000802 | 0.000521 | 0.000471 | 0.000438 | −0.000034 | −0.00028 | −0.001874 | −0.00161 | −0.000816 | 0.000296 |
| 16 | 0.000683 | 0.000449 | 0.000441 | 0.000409 | −0.000051 | −0.000261 | −0.001831 | −0.001543 | −0.000807 | 0.000328 |
| 17 | 0.000704 | 0.000469 | 0.000417 | 0.00043 | −0.000066 | −0.000281 | −0.001864 | −0.001588 | −0.000818 | 0.000178 |
| 18 | 0.000658 | 0.000442 | 0.000392 | 0.0004 | −0.000078 | −0.000276 | −0.001729 | −0.001528 | −0.000761 | 0.000226 |
| 19 | 0.000755 | 0.000494 | 0.000453 | 0.000419 | −0.000087 | −0.000303 | −0.001957 | −0.001613 | −0.000804 | 0.000304 |
| 20 | 0.000658 | 0.000462 | 0.000411 | 0.000385 | −0.000034 | −0.000234 | −0.001732 | −0.00154 | −0.000832 | 0.00027 |
| 21 | 0.000648 | 0.000436 | 0.000412 | 0.000381 | −0.000046 | −0.000255 | −0.001722 | −0.001528 | −0.000755 | 0.00027 |
| 22 | 0.000668 | 0.000433 | 0.000411 | 0.000388 | −0.000029 | −0.000253 | −0.001739 | −0.00153 | −0.000693 | 0.000334 |
| 23 | 0.000733 | 0.000478 | 0.000423 | 0.000384 | −0.00009 | −0.000312 | −0.001895 | −0.001629 | −0.000719 | 0.000428 |
| 24 | 0.000749 | 0.000464 | 0.000414 | 0.000376 | −0.000106 | −0.000327 | −0.001868 | −0.001671 | −0.000805 | 0.000476 |
| 25 | 0.000675 | 0.000454 | 0.000373 | 0.000378 | −0.000099 | −0.000297 | −0.001771 | −0.001485 | −0.000706 | 0.000383 |
| 26 | 0.000651 | 0.000441 | 0.000401 | 0.000387 | −0.000056 | −0.000242 | −0.001743 | −0.001453 | −0.00075 | 0.0002.46 |

TABLE 21-2-continued

|    | $X_{11}$ | $X_{12}$ | $X_{13}$ | $X_{14}$ | $X_{15}$ | $X_{16}$ | $X_{17}$ | $X_{18}$ | $X_{19}$ | $X_{20}$ |
|----|----------|----------|----------|----------|----------|----------|----------|----------|----------|----------|
| 27 | 0.000618 | 0.000394 | 0.000363 | 0.000354 | −0.000063 | −0.000242 | −0.001569 | −0.001359 | −0.000629 | 0.000369 |
| 28 | 0.000613 | 0.000422 | 0.000391 | 0.000372 | −0.000037 | −0.000257 | −0.001655 | −0.001429 | −0.000719 | 0.000289 |
| 29 | 0.000614 | 0.000408 | 0.000352 | 0.000345 | −0.000067 | −0.00023 | −0.001603 | −0.001334 | −0.000688 | 0.000348 |
| 30 | 0.000629 | 0.000396 | 0.000327 | 0.000328 | −0.000084 | −0.000266 | −0.001582 | −0.001351 | −0.00062 | 0.000398 |
| 31 | 0.000686 | 0.000432 | 0.000375 | 0.000373 | −0.000081 | −0.000326 | −0.001808 | −0.0015 | −0.000745 | 0.000401 |
| 32 | 0.000692 | 0.000436 | 0.000383 | 0.000378 | −0.000077 | −0.000306 | −0.001771 | −0.001485 | −0.000715 | 0.000419 |
| 33 | 0.000676 | 0.000499 | 0.000455 | 0.00043 | 0.000048 | −0.000146 | −0.001588 | −0.001352 | −0.000735 | 0.000026 |
| 34 | 0.000671 | 0.000514 | 0.00049 | 0.000448 | 0.000061 | −0.000118 | −0.001586 | −0.00145 | −0.000849 | 0.00013 |
| 35 | 0.000757 | 0.000556 | 0.000487 | 0.000452 | 0.000004 | −0.000204 | −0.001814 | −0.001452 | −0.000782 | 0.000237 |
| 36 | 0.000659 | 0.000513 | 0.000489 | 0.000443 | 0.000077 | −0.000104 | −0.001644 | −0.001292 | −0.000766 | −0.000032 |
| 37 | 0.000712 | 0.000508 | 0.000457 | 0.000431 | −0.000029 | −0.000253 | −0.001866 | −0.001598 | −0.000964 | −0.000042 |
| 38 | 0.000727 | 0.000519 | 0.000489 | 0.000435 | −0.000059 | −0.000262 | −0.001936 | −0.001579 | −0.000955 | 0.000106 |
| 39 | 0.000656 | 0.000497 | 0.000458 | 0.000445 | −0.00004 | −0.000211 | −0.001868 | −0.001477 | −0.000882 | −0.000065 |
| 40 | 0.000524 | 0.000469 | 0.000467 | 0.000475 | 0.000135 | −0.000042 | −0.001564 | −0.001091 | −0.00068 | −0.000143 |
| 41 | 0.000538 | 0.000458 | 0.000454 | 0.000426 | 0.000033 | −0.000151 | −0.001793 | −0.001162 | −0.000565 | 0.000136 |
| 42 | 0.000548 | 0.000441 | 0.000464 | 0.000474 | 0.00011 | −0.000049 | −0.001633 | −0.001076 | −0.000596 | −0.000085 |
| 43 | 0.000529 | 0.000511 | 0.000487 | 0.000504 | 0.000169 | 0.000009 | −0.001575 | −0.001095 | −0.000667 | −0.000152 |

TABLE 21-3

|    | $X_{21}$ | $X_{22}$ | $X_{23}$ | $X_{24}$ | $X_{25}$ | $X_{26}$ |
|----|----------|----------|----------|----------|----------|----------|
| 1  | −0.000713 | −0.000427 | −0.000318 | −0.000218 | 0.00014 | 0.00018 |
| 2  | −0.000834 | −0.00044 | −0.000284 | −0.000198 | 0.000175 | 0.000199 |
| 3  | −0.000749 | −0.000445 | −0.000319 | −0.000203 | 0.000241 | 0.00018 |
| 4  | −0.000677 | −0.000433 | −0.000331 | −0.000212 | 0.000105 | 0.00017 |
| 5  | −0.000827 | −0.000451 | −0.00033 | −0.000204 | 0.000189 | 0.000194 |
| 6  | −0.000714 | −0.0005 | −0.000305 | −0.000196 | 0.000251 | 0.000187 |
| 7  | −0.000688 | −0.000403 | −0.000299 | −0.000202 | 0.000173 | 0.000161 |
| 8  | −0.000741 | −0.000423 | −0.000414 | −0.000294 | 0.000108 | 0.000172 |
| 9  | −0.000709 | −0.000492 | −0.000291 | −0.000169 | 0.000261 | 0.000168 |
| 10 | −0.000661 | −0.000493 | −0.00032 | −0.000222 | 0.00022 | 0.0001 |
| 11 | −0.000676 | −0.000501 | −0.00029 | −0.000181 | 0.000295 | 0.000142 |
| 12 | −0.000758 | −0.000497 | −0.000351 | −0.00023 | 0.00022 | 0.000104 |
| 13 | −0.000719 | −0.000512 | −0.00034 | −0.000214 | 0.000235 | 0.000154 |
| 14 | −0.000768 | −0.0005 | −0.00034 | −0.000227 | 0.000141 | 0.000135 |
| 15 | −0.000765 | −0.000462 | −0.000356 | −0.000236 | 0.00009 | 0.000253 |
| 16 | −0.000741 | −0.000475 | −0.000288 | −0.000198 | 0.000218 | 0.000199 |
| 17 | −0.000642 | −0.000449 | −0.000407 | −0.000309 | 0.000088 | 0.000175 |
| 18 | −0.000699 | −0.000456 | −0.000404 | −0.000304 | 0.000083 | 0.000134 |
| 19 | −0.000773 | −0.000517 | −0.000393 | −0.000288 | 0.000197 | 0.000189 |
| 20 | −0.000692 | −0.000443 | −0.000327 | −0.000223 | 0.000108 | 0.000192 |
| 21 | −0.000678 | −0.000489 | −0.000393 | −0.000245 | 0.000205 | 0.000125 |
| 22 | −0.000589 | −0.000501 | −0.000357 | −0.000248 | 0.000163 | 0.000142 |
| 23 | −0.000644 | −0.000497 | −0.000369 | −0.000235 | 0.000266 | 0.000119 |
| 24 | −0.000803 | −0.000572 | −0.000381 | −0.000235 | 0.000.309 | 0.000059 |
| 25 | −0.000787 | −0.000467 | −0.000325 | −0.00023 | 0.000213 | 0.000136 |
| 26 | −0.000695 | −0.00043 | −0.000317 | −0.000227 | 0.000121 | 0.000208 |
| 77 | −0.000706 | −0.000419 | −0.000264 | −0.000187 | 0.000247 | 0.000161 |
| 28 | −0.000688 | −0.000403 | −0.000315 | −0.000215 | 0.000149 | 0.000178 |
| 29 | −0.00065 | −0.000418 | −0.000259 | −0.000178 | 0.000223 | 0.000156 |
| 30 | −0.000704 | −0.000423 | −0.00025 | −0.000156 | 0.000231 | 0.000151 |
| 31 | −0.000777 | −0.00047 | −0.000329 | −0.00022 | 0.000237 | 0.000162 |
| 32 | −0.000755 | −0.000437 | −0.000313 | −0.000203 | 0.000193 | 0.000173 |
| 33 | −0.000419 | −0.0004 | −0.000357 | −0.000281 | 0.000071 | 0.000143 |
| 34 | −0.000414 | −0.000371 | −0.000401 | −0.000352 | 0.000023 | 0.000216 |
| 35 | −0.000575 | −0.000476 | −0.000286 | −0.000189 | 0.000162 | 0.000199 |
| 36 | −0.000454 | −0.000427 | −0.00035 | −0.000244 | −0.000006 | 0.000217 |
| 37 | −0.000332 | −0.000411 | −0.000379 | −0.000314 | −0.000047 | 0.000267 |
| 38 | −0.000514 | −0.000394 | −0.000313 | −0.000201 | 0.000063 | 0.000286 |
| 39 | −0.000311 | −0.000381 | −0.000322 | −0.000238 | −0.000035 | 0.000234 |
| 40 | −0.000218 | −0.000325 | −0.000273 | −0.000204 | −0.000126 | 0.000201 |
| 41 | −0.000469 | −0.000332 | −0.000256 | −0.000154 | 0.00014 | 0.000209 |
| 42 | −0.000304 | −0.000382 | −0.000226 | −0.000172 | −0.00001 | 0.000209 |
| 43 | −0.000256 | −0.000319 | −0.000208 | −0.000196 | −0.000098 | 0.000224 |

|    | $X_{27}$ | $X_{28}$ | $X_{29}$ | $X_{30}$ |
|----|----------|----------|----------|----------|
| 1 | 0.000088 | −0.000012 | −0.000011 | 0.000012 |
| 2 | 0.000048 | −0.000088 | −0.000025 | −0.00003 |
| 3 | 0.000068 | −0.000046 | −0.000004 | 0.000015 |
| 4 | −0.000003 | −0.000053 | −0.000079 | −0.000073 |
| 5 | 0.000086 | −0.000085 | −0.000005 | −0.000035 |
| 6 | 0.000091 | −0.000092 | 0.000028 | 0.000037 |
| 7 | 0.000063 | −0.000073 | 0.000005 | 0.000004 |

TABLE 21-3-continued

| | | | | |
|---|---|---|---|---|
| 8 | 0.000021 | −0.00008 | −0.000023 | −0.000027 |
| 9 | 0.000065 | 0.00001 | 0.000004 | 0.000034 |
| 10 | 0.000015 | −0.000103 | −0.000027 | 0.000018 |
| 11 | 0.0000.31 | −0.000108 | 0.000007 | 0.000011 |
| 12 | −0.00003 | −0.00005 | −0.000053 | −0.000051 |
| 13 | 0.000029 | −0.000054 | −0.00001 | 0.000006 |
| 14 | −0.000003 | −0.000058 | −0.000044 | −0.000064 |
| 15 | 0.00005 | 0.000007 | −0.000087 | −0.00015 |
| 16 | 0.000087 | −0.000022 | 0.000057 | 0.000082 |
| 17 | 0.00005 | −0.000033 | −0.000038 | −0.000118 |
| 18 | −0.000015 | −0.000069 | −0.000071 | −0.000076 |
| 19 | 0.000069 | −0.00007 | −0.000004 | −0.000024 |
| 20 | 0.000085 | −0.000035 | −0.000018 | −0.000039 |
| 21 | 0.000028 | −0.000086 | −0.000044 | −0.000038 |
| 22 | 0.000009 | −0.00009 | −0.000135 | −0.00013 |
| 23 | 0.000027 | −0.000112 | 0.000032 | 0.000071 |
| 24 | 0.00002 | −0.000142 | 0.000018 | 0.000025 |
| 25 | 0.000061 | −0.000093 | −0.000007 | −0.00002 |
| 26 | 0.000051 | −0.000063 | −0.000074 | −0.00006 |
| 77 | 0.000053 | −0.000048 | −0.000023 | 0.000023 |
| 28 | 0.000054 | −0.00009 | 0.000006 | −0.000006 |
| 29 | 0.000044 | −0.000008 | −0.000037 | −0.00002 |
| 30 | 0.00004 | −0.000069 | 0.000007 | 0.000006 |
| 31 | 0.000024 | −0.000072 | −0.000003 | 0.000026 |
| 32 | 0.000048 | −0.000077 | 0.000006 | 0.000026 |
| 33 | 0.000024 | −0.000072 | −0.000026 | −0.000065 |
| 34 | 0.000027 | −0.000025 | −0.000077 | −0.00013 |
| 35 | 0.000101 | −0.000029 | 0.000046 | 0.000055 |
| 36 | 0.000075 | −0.000057 | −0.000081 | −0.000084 |
| 37 | 0.00016 | 0.000038 | 0.000068 | 0.000046 |
| 38 | 0.000144 | 0.000091 | 0.000073 | 0.000032 |
| 39 | 0.00013 | 0.000015 | 0.000085 | 0.000075 |
| 40 | 0.000147 | 0.000073 | 0.000074 | 0.000016 |
| 41 | 0.000159 | 0.000082 | 0.000119 | 0.000109 |
| 42 | 0.00014 | 0.000143 | 0.000053 | 0.000018 |
| 43 | 0.00015 | 0.000099 | 0.000086 | 0.000016 |

2. Obtaining the Pharmacodynamics Data of Spina *Gleditsiae* and Counterfeits Thereof (1) Determination of Nirtric Oxide (NO)—Griess Method When macrophages are stimulated by lipopolysaccharide (LPS), cell surface receptors will be activated to initiate various signal cascade amplification effects, resulting in the generation of pro-inflammatory factors such as Nirtric Oxide (NO), TNF-α, IL-6 and the like, which then leads to damages. The level of inflammation can be determined by measuring the level of NO in the supernatant of cells.

NO in the supernatant of cell cultures is particularly unstable and can be quickly metabolized to generate relatively stable nitrite, which can react with p-Aminobenzene-sulfonic acid and α-naphthylamine in the Griess reagent under acidic conditions to generate red azo compounds which have a maximum absorption peak at 540 nm, and the concentration of the product is linear to the NO concentration, therefore the content of NO in the supernatant of the cell cultures can be determined according to this principle. Specific steps are as follows:

I. Preparing a sodium nitrite standard, and preparing sodium nitrite solutions accurately of 10, 20, 40, 60, 80 and 100 μM respectively for the determination of the standard curve;

II. Placing Griess reagent (50 μL per well) into a 96-well plate, adding the supernatant from step I or sodium nitrite standard solutions of different concentrations (50 μL per well), reacting for 30 min at room temperature, removing bubbles in wells, and measuring the OD value at 540 nm; and III. Plotting a standard curve according to the OD value of the sodium nitrite standard solution, and substituting the absorbance values of samples into the standard curve to obtain the NO content in the supernatant of various experiment groups.

(2) Determination of Antioxidant Activities-ORAC Method

In the ORAC method, sodium flourescein (FL) is used as a fluorescent probe to observe the decrescence of fluorescence intensity after the reaction between the sodium fluorescein and hydrogen peroxide radicals produced by thermal decomposition of an azo compound, 2,2'-azo-bis(2-amidinopropane) dihydrochloride (AAPH) (the decrescence of fluorescence intensity will slow down in presence of antioxidants), and the equivalents of the antioxidant standard substance-water-soluble vitamin E analogue (6-hydro-2,5,7, 8-tetramethylchroman-2-carboxylic acid (Trolox)) were used to evaluate the ability of various antioxidants in the system to delay the decrescence of fluorescence intensity of the probe, so as to evaluate the antioxidant capacity of the antioxidants.

The NO inhibitory activities and ORAC antioxidant activities of samples are shown in Table 22.

TABLE 22

Anti-inflammatory and antioxidant activities of samples

| No. | NO | ORAC antioxidant activity |
|---|---|---|
| 1 | 15.85 | 267.91 |
| 2 | 17.81 | 833.23 |
| 3 | 18.68 | 301.81 |
| 4 | — | 320.41 |
| 5 | 17.85 | 448.42 |
| 6 | 14.97 | 310.38 |
| 7 | 19.33 | 438.44 |

TABLE 22-continued

Anti-inflammatory and antioxidant activities of samples

| No. | NO | ORAC antioxidant activity |
|---|---|---|
| 8 | 16.01 | 340.66 |
| 9 | 18.05 | 321.57 |
| 10 | 15.98 | 148.11 |
| 11 | 17.41 | 111.51 |
| 12 | — | 332.41 |
| 13 | — | 411.32 |
| 14 | — | 269.4 |
| 15 | 14.77 | 961.13 |
| 16 | 15.95 | 271.59 |
| 17 | 13.19 | 338.89 |
| 18 | 14.64 | 162.49 |
| 19 | 12.83 | 348.11 |
| 20 | 13.44 | 405.03 |
| 21 | 13.93 | 306.25 |
| 22 | 17.83 | 66.8 |
| 23 | 15.06 | 263.52 |
| 24 | — | 128.36 |
| 33 | 14.22 | 382.43 |
| 34 | 0 | 248.08 |
| 35 | 13.61 | 563.05 |
| 36 | — | 458.65 |
| 37 | 13.42 | 371.42 |
| 38 | 14.52 | 565.31 |
| 39 | 12.31 | 789.59 |
| 40 | 14.73 | 404.05 |
| 41 | 13.66 | 304.38 |
| 42 | 13.47 | 418.25 |
| 43 | 17.52 | 838.19 |

—: not detected

3. Correlation Analysis of Medicinal Effects and Near-Infrared Spectra for Exploring Characteristic Spectra Capable of Representing Medicinal Effects Anti-inflammatory and antioxidant efficacy and SPA characteristic near-infrared spectra were used for Pearson two-tailed correlation analysis. It can be seen from analysis results in Table 23 that peaks No. $X_1$, $X_7$, $X_8$, $X_9$, $X_{10}$, $X_{12}$, $X_{13}$, $X_{14}$, $X_{20}$, $X_{21}$, $X_{22}$, $X_{23}$, $X_{24}$, $X_{25}$, $X_{26}$, $X_{27}$ and $X_{28}$ are significantly correlated with the medicinal effect of Spina gleditsiae.

TABLE 23

Results of correlation analysis between anti-inflammatory and antioxidant activities of Spina gleditsiae and SPA characteristic near-infrared spectra

| Peak No. | Pearson correlation (two-tailed test) NO | ORAC |
|---|---|---|
| $X_1$ | −0.400* | −0.020 |
| $X_2$ | −0.247 | −0.073 |
| $X_3$ | −0.232 | −0.133 |
| $X_4$ | −0.305 | −0.204 |
| $X_5$ | −0.312 | −0.166 |
| $X_6$ | −0.286 | −0.100 |
| $X_7$ | 0.440* | −0.302 |
| $X_8$ | 0.511** | 0.210 |
| $X_9$ | 0.494** | 0.048 |
| $X_{10}$ | −0.067 | 0.515** |
| $X_{11}$ | 0.096 | 0.036 |
| $X_{12}$ | −0.226 | 0.648** |
| $X_{13}$ | −0.354 | 0.607** |
| $X_{14}$ | −0.316 | 0.573** |
| $X_{15}$ | −0.305 | 0.301 |
| $X_{16}$ | −0.329 | 0.275 |
| $X_{17}$ | −0.306 | −0.022 |
| $X_{18}$ | −0.117 | 0.216 |
| $X_{19}$ | 0.214 | −0.193 |
| $X_{20}$ | 0.328 | −0.386* |
| $X_{21}$ | −0.371* | 0.227 |
| $X_{22}$ | −0.250 | 0.420* |
| $X_{23}$ | 0.362 | 0.336* |
| $X_{24}$ | 0.573** | 0.175 |
| $X_{25}$ | 0.361 | −0.452** |
| $X_{26}$ | −0.259 | 0.631** |
| $X_{27}$ | −0.009 | 0.430** |
| $X_{28}$ | −0.172 | 0.429** |
| $X_{29}$ | 0.085 | 0.238 |
| $X_{30}$ | 0.253 | −0.004 |

*significantly correlated below the level of 0.05,
**significantly correlated below the level of 0.01

4. Training Set and Testing Set Classification

Kennard-Stone algorithm. The training set included 32 batches of samples, including 24 batches of Spina gleditsiae., 3 batches of Gleditsia japonica Miq., 2 batches of Gleditsia microphylla Gordon ex Y. T. Lee and 3 batches of Rubus cochinchinensis Tratt., and the testing set thereof included 11 batches of samples, including 8 batches of Spina gleditsiae., 1 batch of Gleditsia japonica Miq., 1 batch of Gleditsia microphylla Gordon ex YT Lee and 1 batch of Rubus cochinchinensis Tratt.

Samples of the training set were No. 2, 5, 6, 7, 8, 9, 10, 12, 13, 14, 15, 16, 17, 18, 19, 20, 21, 22, 23, 24, 25, 26, 28, 30, 34, 35, 36, 38, 39, 41, 42, and 43.

Samples of the testing set were No. 1, 3, 4, 11, 27, 29, 31, 32, 33, 37, and 40.

5. Characteristic Extraction Under the Guide Of the Pharmacodynamics Information Variables significantly correlated with the medicinal effect in the results of spectrum-effect correlation analysis (that is, variables No. $X_1$, $X_7$, $X_8$, $X_9$, $X_{10}$, $X_{12}$, $X_{13}$, $X_{14}$, $X_{20}$, $X_{21}$, $X_{22}$, $X_{23}$, $X_{24}$, $X_{25}$, $X_{26}$, $X_{27}$, and $X_{28}$), were screened by stepwise discriminant analysis to perform characteristic extraction. The screening was performed stepwise through F-test. In each step, the most significant variables that meet a specified level were selected, and originally introduced variables were removed which are insignificant due to the introduction of new variables, until no variable could be introduced or removed. Spina gleditsiae, Gleditsia japonica Miq., Gleditsia microphylla Gordon ex YT., and Rubus cochincinensis Tratt were simultaneously compared by stepwise discriminant analysis, and representative peak variables of the characteristics were screened. The dimension reduction results are shown in Table 24.

TABLE 24

Groups and characteristic peaks of samples

| Group | Peak |
|---|---|
| Spina gleditsiae. vs. Gleditsia japonica Miq. vs. Gleditsia microphylla Gordon ex YT vs. Rubus cochinchinensis Tratt. | $X_8$, $X_{10}$, $X_{14}$, $X_{21}$ |

6. Establishment of Discriminant Functions of A Pattern Recognition Model

The characteristic variables selected by stepwise discrimination and discriminant coefficients are shown in Table 25, and two established discriminant functions are shown below.

TABLE 25

Typical discriminant function coefficient

| | Function | |
|---|---|---|
| | 1 | 2 |
| $X_8$ | 49050.801 | −27730.331 |
| $X_{10}$ | 8875.62 | 34288.661 |
| $X_{14}$ | −2798.314 | −29368.865 |
| $X_{21}$ | 21876.983 | 10924.346 |
| Constant | 2.356 | 4.075 |

$F_1 = 49050.801X_8 + 8875.62X_{10} − 2798.314X_{14} + 21876.983X_{21} + 2.356$
$F_2 = −27730.331X_8 + 34288.661X_{10} − 29368.865X_{14} + 10924.346X_{21} + 4.075$

7. Model Validation (1) Internal validation of the model. The model was validated by Leave-one-out internal cross-validation. Results demonstrate that in the model established as above, the accuracy of the discrimination with the leave-one-out internal cross-validation is 100%.

(2) The testing set is used for the external validation of the model, and the characteristic peaks of the samples in the testing set were substituted into the discriminant function, to obtain discriminant scores and discriminant classification results of the samples. The results are shown in Table 26. The discriminant results of the model are consistent with the results of the character identification, and the accuracy of the discrimination is 100%.

TABLE 26

The discriminant results of the samples in the testing set

| Sample No. | F1 | F2 | Results | Whether the classification is correct |
|---|---|---|---|---|
| 1 | −0.69018 | −1.66603 | Spina gleditsiae. | Correct |
| 3 | −0.86818 | 0.26397 | Spina gleditsiae. | Correct |
| 4 | −1.52508 | 0.08616 | Spina gleditsiae. | Correct |
| 11 | −1.6957 | 0.11647 | Spina gleditsiae. | Correct |
| 27 | −0.87166 | −1.02215 | Spina gleditsiae. | Correct |
| 29 | −0.16512 | −0.0745 | Spina gleditsiae. | Correct |
| 31 | −2.77895 | −0.25969 | Spina gleditsiae. | Correct |
| 32 | −2.26259 | −0.19393 | Spina gleditsiae. | Correct |
| 33 | 0.50977 | 4.80926 | Gleditsia japonica Miq. | Correct |
| 37 | 8.62617 | 2.37344 | Gleditsia microphylla Gordon ex YT | Correct |
| 40 | 10.04078 | 0.58742 | Rubus cochinchinensis Tratt. | Correct |

8. Visualization of the Results

Figure 11:
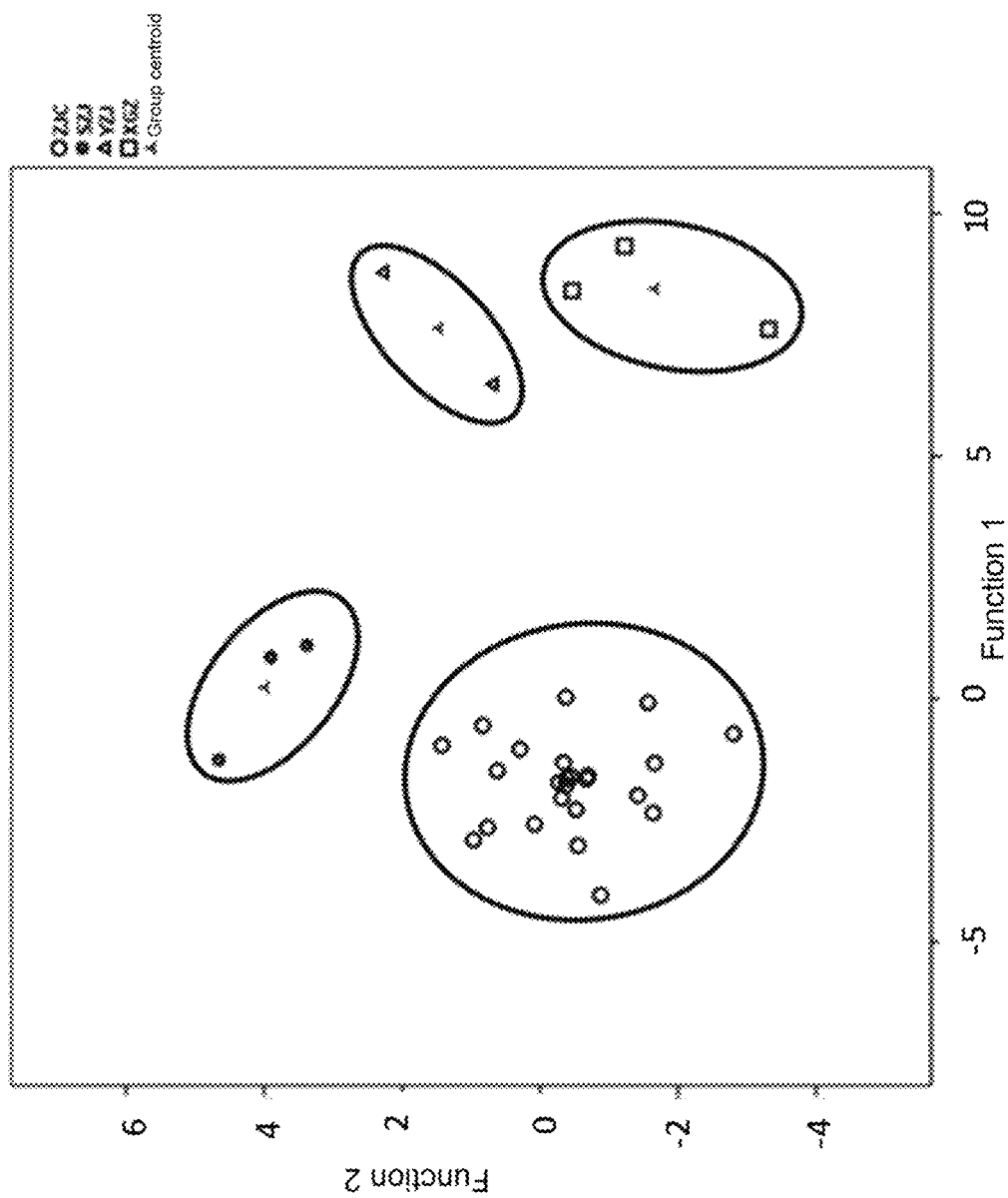
FIG. 11 is a diagram showing the distribution of samples in the training set of Spina gleditsiae. and counterfeits thereof, with values of discriminant functions (values of $F_1$ and $F_2$, namely, Function 1 and Function 2) as horizontal and vertical coordinates.
Figure 12:
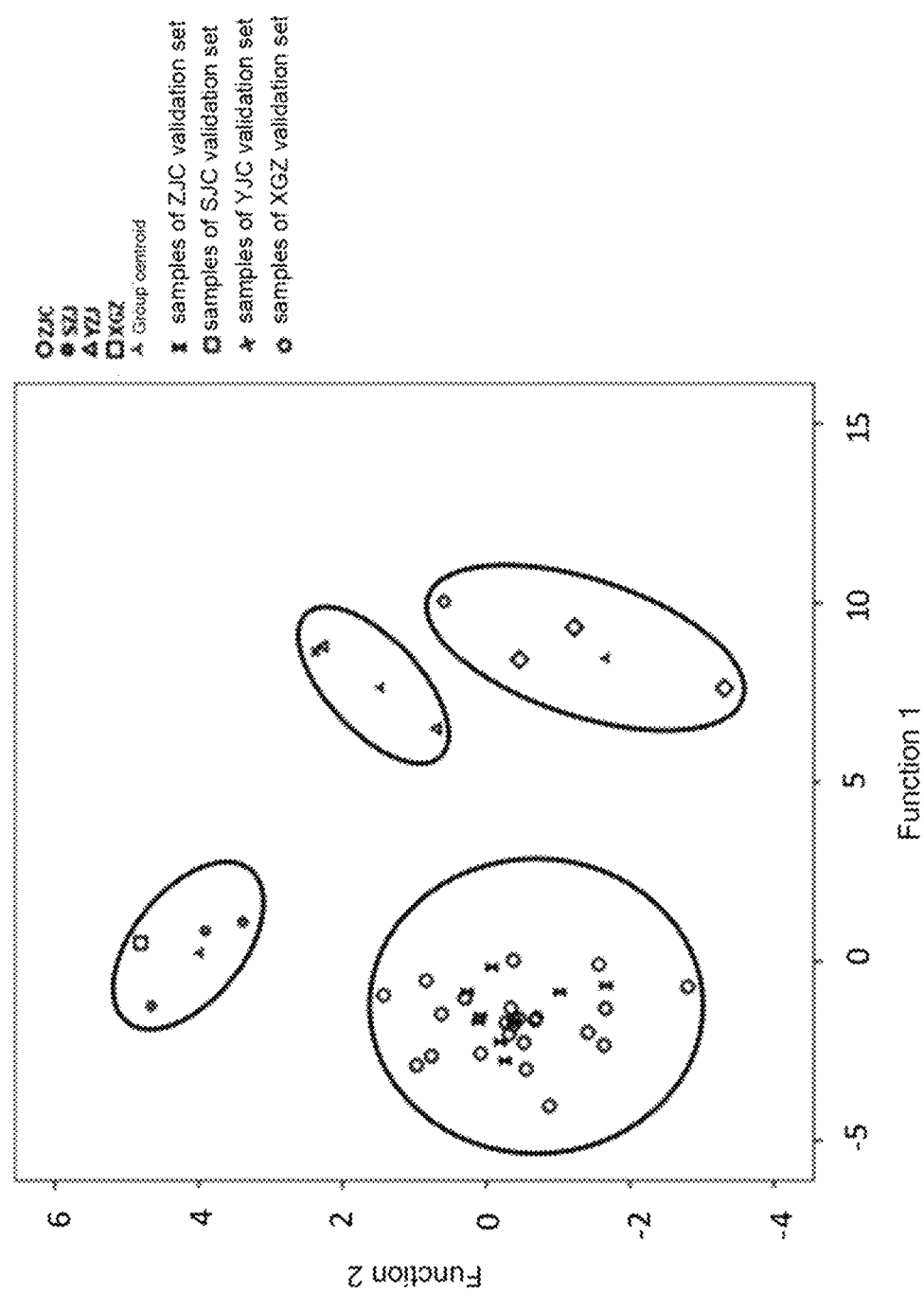
FIG. 12 is a diagram showing the distribution of samples of the training set and the testing set of Spina gleditsiae. and counterfeits thereof, with values of discriminant functions (values of $F_1$ and $F_2$, namely, Function 1 and Function 2) as horizontal and vertical coordinates.

Based on discriminant function values, distribution diagrams of samples of the training set and the testing set were obtained. F1 and F2 are the horizontal and vertical coordinates of the samples in the distribution diagram, respectively. The results of the distribution diagrams are shown in FIG. 11 (training set) and FIG. 12 (training set and testing set). In FIG. 11 and FIG. 12, Spina gleditsiae. (ZJC), Gleditsia japonica Miq.(SZJ). Gleditsia microphylla Gordon ex YT (YZC) and Rubus cochinchinensis Tratt. (XGZ) in the samples of the training set and the testing set can be effectively discriminated.

Therefore, according to the method described above, the characteristic extraction was carried out with stepwise discriminant analysis under the guide of the pharmacodynamics information, so that four characteristic values were obtained and two discriminant functions were established, through which Spina gleditsiae, Gleditsia japonica Miq.(SZJ), Gleditsia microphylla Gordon ex YT (YZC) and Rubus cochinchinensis Tratt. can be effectively discriminated.

The applicant has stated that although the methods of the present invention are described through the examples described above, the present invention is not limited to the processes and steps described above, which means that implementation of the present invention does not necessarily depend on the processes and steps described above. It should be apparent to those skilled in the art that any improvements made to the present invention, equivalent replacements of raw materials selected in the present invention and addition of adjuvant ingredients thereof, and selections of specific methods, etc., all fall within the protection scope and the disclosed scope of the present invention.

The invention claimed is:

1. A method for establishing chemical pattern recognition for evaluating traditional Chinese medicine quality based on pharmacodynamics information, comprising the following steps:

(1) collecting overall chemical information capable of representing internal quality of traditional Chinese medicine samples, obtaining pharmacodynamics information representing clinical efficacy of the traditional Chinese medicine samples, analyzing a spectrum-effect relationship between the chemical information and the pharmacodynamics information, obtaining indexes significantly correlated with the pharmacodynamics information as characteristic chemical indexes;

(2) classifying the traditional Chinese medicine samples into a training set and a testing set, and extracting characteristic variables from the samples in the training set by adopting a supervised pattern recognition method which uses the characteristic chemical indexes obtained in step (1) as input variables;

(3) establishing a pattern recognition model by using the characteristic variables extracted in step (2); and (4) bringing characteristic variable values of the samples in the testing set into the pattern recognition model, and completing chemical pattern recognition evaluation of the traditional Chinese medicine quality;

wherein the method for establishing chemical pattern recognition for evaluating traditional Chinese medicine quality based on pharmacodynamics information further comprises chemical pattern recognition on authenticity of a traditional Chinese medicine, *Salviae* miltiorrhizae radix et rhizoma, chemical pattern recognition on *Citrus grandis* 'Tomentosa' and *Citrus grandis* (L.) Osbeck from Exocarpium *citri grandis*;

wherein the chemical pattern recognition on *Citrus grandis* 'Tomentosa' and *Citrus grandis* (L.) Osbeck from Exocarpium *citri grandis*, comprises:

A. Collecting overall chemical information capable of representing internal quality of *Salviae* miltiorrhizae radix et rhizoma and counterfeits thereof or representing internal quality of samples of Exocarpium *citri grandis* comprising *Citrus grandis* 'Tomentosa' and *Citrus grandis* (L.) Osbeck by high performance liquid chromatography (HPLC), and obtaining pharmacodynamics information representing clinical efficacy of the traditional Chinese medicine; performing data normalization for specific absorption peaks selected from the HPLC chromatograms by a Z-normalization method and performing bivariate spectrum-effect correlation analysis on the normalized data, to obtain HPLC fingerprint data significantly correlated with pharmacodynamic activity of *Salviae* miltiorrhizae radix et rhizoma and counterfeits thereof or HPLC fingerprint data significantly correlated with pharmacodynamic activity of *Citrus grandis* 'Tomentosa' and *Citrus grandis* (L.) Osbeck from Exocarpium *citri grandis*, and using the HPLC fingerprint data as characteristic chemical indexes representing the medicinal effects;

B. Randomly classifying *Salviae* miltiorrhizae radix et rhizoma and counterfeits thereof or the samples of Exocarpium *citri grandis* into a training set and a testing set, using the characteristic chemical indexes obtained in step A as input variables to screen characteristic chemical indexes of the samples in the training set with stepwise discriminant analysis, thereby removing uncorrelated variables and screening out characteristic variables;

C. Establishing a pattern recognition model for *Salviae* miltiorrhizae radix et rhizoma and counterfeits thereof or a pattern recognition model for the samples of Exocarpium *citri grandis* by using the characteristic variables obtained in step B; and D. Bringing characteristic variable values of the samples in the testing set into the pattern recognition model to determine the accuracy of discriminating *Salviae* miltiorrhizae radix et rhizoma and counterfeits thereof or the accuracy of discrimination *Citrus grandis* 'Tomentosa' from *Citrus grandis* (L.) Osbeck in Exocarpium *citri grandis* wherein a selection principle of the specific absorption peaks of *Salviae* miltiorrhizae radix et rhizoma and counterfeits thereof in step A is peaks satisfying at least one of following conditions: (I) peaks common to *Salviae* miltiorrhizae radix et rhizoma, *Salvia przewalskii* Maxim. and *Salvia yunnanensis* C. H. Wright; (II) peaks respectively specific to *Salviae* miltiorrhizae radix et rhizoma, *Salvia przewalskii* Maxim. and *Salvia yunnanensis* C. H. Wright; and (III) peaks with high content of components;

a selection principle of the specific absorption peaks of *Citrus grandis* 'Tomentosa' and *Citrus grandis* (L.) Osbeck in Exocarpium *citri grandis* in the step A is that peaks are common to *Citrus grandis* 'Tomentosa' and *Citrus grandis* (L.) Osbeck;

the method for the randomly classifying into the training set and the testing set in step B is random classification by using a random algorithm;

the training set of *Salviae* miltiorrhizae radix et rhizoma and counterfeits thereof in step B comprises 20 batches of samples, comprising 12 batches of *Salviae* miltiorrhizae radix et rhizoma, 4 batches of *Salvia przewalskii* Maxim. and 4 batches of *Salvia yunnanensis* C. H. Wright, and the testing set comprises 29 batches of samples, comprising 26 batches of *Salviae* miltiorrhizae radix et rhizoma, 2 batches of *Salvia przewalskii* Maxim. and 1 batch of *Salvia yunnanensis* C. H. Wright;

the training set of samples of Exocarpium *citri grandis* in step B comprises 22 batches of samples, which are 10 batches of *Citrus grandis* 'Tomentosa' and 12 batches of *Citrus grandis* (L.) Osbeck. The testing set comprises 9 batches of samples, which are 5 batches of *Citrus grandis* 'Tomentosa' and 4 batches of *Citrus grandis* (L.) Osbeck;

the screened characteristic variables of *Salviae* miltiorrhizae radix et rhizoma and counterfeits thereof in step B are $X_6$, $X_7$ and $X_{13}$;

the screened characteristic variables of the samples of Exocarpium *citri grandis* in step B are $X_7$, $X_8$ and $X_{20}$;

functions of the pattern recognition model established for *Salviae* miltiorrhizae radix et rhizoma and counterfeits thereof in step C are:

$$F_1 = 0.492X_6 + 8.762X_7 - 1.249X_{13} - 1.869, \text{ and}$$

$$F_2 = -2.571X_6 + 4.521X_7 + 3.277X_{13} + 1.288;$$

a function of the pattern recognition model established for the samples of Exocarpium *citri grandis* in step C is:

$$F_1 = 0.828X_7 + 0.767X_8 - 1.303X_{20} - 0.099.$$

2. A method for establishing chemical pattern recognition for evaluating traditional Chinese medicine quality based on pharmacodynamics information, comprising the following steps:

(1) collecting overall chemical information capable of representing internal quality of traditional Chinese medicine samples, obtaining pharmacodynamics information representing clinical efficacy of the traditional Chinese medicine samples, analyzing a spectrum-effect relationship between the chemical information and the pharmacodynamics information, obtaining indexes significantly correlated with the pharmacodynamics information as characteristic chemical indexes;

(2) classifying the traditional Chinese medicine samples into a training set and a testing set, and extracting characteristic variables from the samples in the training set by adopting a supervised pattern recognition method which uses the characteristic chemical indexes obtained in step (1) as input variables;

(3) establishing a pattern recognition model by using the characteristic variables extracted in step (2); and (4) bringing characteristic variable values of the samples in the testing set into the pattern recognition model, and completing chemical pattern recognition evaluation of the traditional Chinese medicine quality;

wherein the method for establishing chemical pattern recognition for evaluating traditional Chinese medicine quality based on pharmacodynamics information comprises chemical pattern recognition on authenticity of Spina *gleditsiae*;

wherein the method for chemical pattern recognition on authenticity of Spina gleditsiae comprises the following steps:
I. Collecting overall chemical information capable of representing internal quality of samples of Spina gleditsiae and counterfeits thereof by near-infrared spectrometry, obtaining pharmacodynamics information representing clinical efficacy of the traditional Chinese medicine, analyzing the spectrum-effect relationship between the chemical information and the pharmacodynamics information, obtaining characteristic peaks significantly correlated with the pharmacodynamics as characteristic chemical indexes;
II. Randomly classifying the samples of Spina gleditsiae and counterfeits thereof into a training set and a testing set, screening characteristic chemical indexes of the samples in the training set by stepwise discriminant analysis which uses the characteristic chemical indexes obtained in step I as input variables, thereby removing uncorrelated variables and screening out characteristic variables;
III. Establishing a pattern recognition model by using the characteristic variables obtained in step II; and
IV. Bringing characteristic variable values of the samples in the testing set into the pattern recognition model to discriminate a discriminant accuracy of Spina gleditsiae and counterfeits thereof
wherein, after collecting the chemical information of Spina gleditsiae and counterfeits thereof by the near-infrared spectrometry in step I, the method further comprising: performing a pre-treatment of spectral data on the chemical information: removing interference peaks and water peaks in original spectra to obtain peaks within spectral bands of 11800-7500 $cm^{-1}$, 6500-5500 $cm^{-1}$, and 5000-4200 $cm^{-1}$, selecting the peaks within the spectral band of 5000-4200 $cm^{-1}$ as model analysis peaks, pre-treating the peaks within the spectral band of 5000-4200 $cm^{-1}$ by using a first derivative pre-treatment method, and extracting characteristic peaks by using a successive projections algorithm;
the interference peaks are peaks within spectral bands of 12000-11800 $cm^{-1}$, 4200-4000 $cm^{-1}$, 7500-6500 $cm^{-1}$, and 5500-5000 $cm^{-1}$, and the water peaks are peaks within spectral bands of 7500-6500 $cm^{-1}$ and 5500-5000 $cm^{-1}$;
the training set in step II comprises 32 batches of samples, which are 24 batches of Spina gleditsiae, 3 batches of Gleditsia japonica Miq., 2 batches of Gleditsia microphylla Gordon ex Y. T. Lee and 3 batches of Rubus cochinchinensis Tratt, while the testing set comprises 11 batches of samples, which are 8 batches of Spina gleditsiae, 1 batch of Gleditsia japonica Miq, 1 batch of Gleditsia microphylla Gordon ex YT Lee and 1 batch of Rubus cochinchinensis Tratt;
wherein the screened characteristic variables in step II are $X_8$, $X_{10}$, $X_{14}$, and $X_{21}$; functions of the pattern recognition model in step III are:

$F_1 = 49050.801 X_8 + 8875.62 X_{10} - 2798.314 X_{14} + 21876.983 X_{21} + 2.356$, and $F_2 = -27730.331 X_8 + 34288.661 X_{10} - 29368.865 X_{14} + 10924.346 X_{21} + 4.075$.

* * * * *